US008088757B2

(12) United States Patent
Saxena et al.

(10) Patent No.: US 8,088,757 B2
(45) Date of Patent: Jan. 3, 2012

(54) BETULINOL DERIVATIVES AS ANTI-CANCER AGENTS

(75) Inventors: Brij B. Saxena, Englewood, NJ (US); Premila Rathnam, Englewood Cliffs, NJ (US)

(73) Assignee: BioRings LLC, New York, NY (US)

( * ) Notice: Subject to any disclaimer, the term of this patent is extended or adjusted under 35 U.S.C. 154(b) by 662 days.

(21) Appl. No.: 11/665,556

(22) PCT Filed: Sep. 12, 2005

(86) PCT No.: PCT/US2005/032460
§ 371 (c)(1),
(2), (4) Date: Mar. 9, 2009

(87) PCT Pub. No.: WO2006/031756
PCT Pub. Date: Mar. 23, 2006

(65) Prior Publication Data
US 2009/0176753 A1 Jul. 9, 2009

Related U.S. Application Data

(60) Provisional application No. 60/630,150, filed on Nov. 11, 2004, provisional application No. 60/630,103, filed on Nov. 11, 2004, provisional application No. 60/609,080, filed on Sep. 10, 2004.

(51) Int. Cl.
*A61K 31/56* (2006.01)
*C07J 53/00* (2006.01)
(52) U.S. Cl. ........................ 514/169; 552/510
(58) Field of Classification Search .................. 552/510; 514/169
See application file for complete search history.

(56) References Cited

U.S. PATENT DOCUMENTS

| 4,127,124 | A | 11/1978 | Clagett et al. |
| 4,350,683 | A | 9/1982 | Galfre et al. |
| 4,363,799 | A | 12/1982 | Kung et al. |
| 4,381,292 | A | 4/1983 | Bieber et al. |
| 4,423,147 | A | 12/1983 | Secher et al. |
| 5,869,535 | A | 2/1999 | Pezzuto et al. |
| 6,890,533 | B2 | 5/2005 | Bomshteyn et al. |
| 2003/0153538 | A1* | 8/2003 | Kuno et al. ............ 514/169 |

FOREIGN PATENT DOCUMENTS
KR 2001026950 * 4/2001

OTHER PUBLICATIONS

KIm et al., "Developmetn of C-20 Modified Betulinic Acid Derivatives as Antitumor Agents." Bioorganic & Medicinal Chemistry Letters, vol. 11, pp. 2405-2408, 2001.*
Agnihotri et al., "Constituents from the Seeds of *Cordia obliqua* as Potential Anti-Inflammatory Agents", Indian J. Pharm. Sci., 2:66-69 (1987).
Chun et al., "Stereoselective Synthesis of Photoreactive Peptidomimetic γ-Secretase Inhibitors", J. Org. Chem., 69:7344-7347 (2004).
Fulda et al., "Sensitization for Anticancer Drug-Induced Apoptosis by Betulinic Acid", Neoplasia, 7:162-170 (2005).
Hess, "Untersuchung über die Zusammenselzung der Harze; von H. Hefs", Poggendorff's Annalen, 46:319-326 (1839).
Hiroya et al., "Synthesis of Betulin Derivatives and their Protective Effects Against the Cytotoxicity of Cadmium", Bioorg. Med. Chem., 10:3229-3236 (2002).
Hunefeld, "Mittheilungen vermischten Inhalts", J. Prakt. Chem., 7:53-57 (1836).
International Preliminary Report on Patentability for International Application No. PCT/US2005/032460 (issued Mar. 13, 2007).
International Search Report for International Application No. PCT/US05/32460 (mailed Nov. 13, 2006).
Ito et al., "Anti-AIDS Agents. 48. Anti-HIV activity of moronic acid derivatives and the new melliferone-related triterpenoid isolated from Brazilian propolis", J. Nat. Prod., 64:1278-1281 (2001).
Kahlos et al., "Antitumor activity of some compounds and fractions from an n-hexane extract of *Inonotus obliquus*", Acta. Pharm. Feun., 96:33-40 (1987).
Karam et al., "Human CYP2C19 is a major omeprazole 5-hydroxylase, as demonstrated with recombinant cytochrome P450 enzymes", Drug Metab. Discov., 24:1081-1087 (1996).
Katdare et al., "Prevention of mammary preneoplastic transformation by naturally-occurring tumor inhibitors", Cancer Lett., 111:141-147 (1997).
Kerr et al., "Human liver carbamazepine metabolism; Role of CYP3A4 and CYP2C8 in 10,11-epoxide formation", Biochem. Pharmacol., 47:1969-1979 (1994).
Kim et al., "Synthesis of betulinic acid derivatives with activity against human melanoma", Bioorg. Med. Chem. Lett., 8:1707-1712 (1998).

(Continued)

*Primary Examiner* — Barbara P Badio
(74) *Attorney, Agent, or Firm* — Stroock & Stroock & Lavan LLP

(57) ABSTRACT

The present invention relates to a method of treating cancer selected from the group of cancers consisting of prostate cancer, renal cancer, breast cancer, ovarian cancer, CNS cancer, melanoma, lung cancer, and bladder cancer. This method involves administering to a patient in need of such treatment a therapeutically effective amount of a betulinol derivative compound of Formula (I). Also disclosed are conjugated and immunoconjugated derivatives of the compound of Formula (I) as well as methods of making and using them.

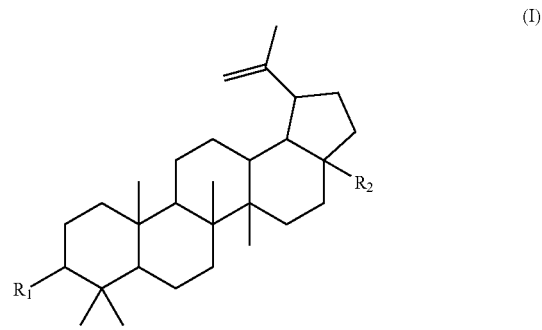

(I)

8 Claims, 14 Drawing Sheets

OTHER PUBLICATIONS

Kim et al., "A concise semi-synthetic approach to betulinic acid from betulin", Synthetic Comm., 27:1607-1612 (1997).

Komissarova et al., "Selective oxidation of betulin by Cr(VI) reagents", Chem. Nat. Comp., 38:58-61 (2002).

Konoshima et al., "Studies on inhibitors of skin-tumor promotion, I. inhibitory effects of triterpenes from *Euptelea polyandra* on Epstein-barr virus activation", *J. Nat. Prod.*, 50:1166-1170 (1987).

Leach et al., "Mutual interaction between remacemide hydrochloride and carbamazepine: two drugs with active metabolites", Epilepsia, 37:1100-1106 (1996).

Liu et al., "Studies on the chemical constituents of *Pyrus communis*", Acta. Bot. Sin., 29:84-87 (1987).

Liu et al., "Monoclonal antibodies to the extracellular domain of prostate-specific membrane atigen also react with tumor vascular endothelium", Cancer Res., 57:3629-3634 (1997).

Lowitz, *Crell's Annalen*, 1:312-316 (1788).

Mason, "Art. VIII.—Chemical Examination of the Bark of the White Birch", Silliman's Am. J., 20:282-285 (1831).

Maurya et al., "Content of betulin and betulinic acid, antitumor agents of *Zizyphus* species", *Fitoterapia*, 60:468-469 (1989).

Miles et al., "Tumor Inhibitors I: Preliminary Investigation of Antitumor Activity of *Sarracenia flava*", J. Pharm. Sci. 63:613-615 (1974).

Nyberg et al., "A PET study of $D_2$ and $5-HT_2$ receptor occupancy induced by risperidone in poor metabolizers of debrisoquin and risperidone", Psychopharmacology, 119:345-348 (1995).

Pisha et al., "Discovery of betulinic acid as a selective inhibitor of human melanoma that functions by induction of apoptosis," *Nat. Med.*, 1:1046-1051 (1995).

Sheth et al., "Tumor-inhibitory agent from *Hyptis emoryi* (labiatae)", J. Pharm. Sci. 61:1819 (1972).

Sheth et al., "Antitumor agents from *Alnus oregona* (betulaceae)", J. Pharm. Sci., 62:139-140 (1973).

Sun et al., "Anti-AIDS agents 49. Synthesis, anti-HIV, and anti-fusion activities of IC9564 analogues based on betulinic acid", *J. Med. Chem.*, 45:4271-4275 (2002).

Tomas-Barberan et al., "A cytotoxic triterpenoid and flavonoids from *Crossopteryx febrifuga*," *Planta Med.*, 54:266-267 (1988).

Turner et al., "The interaction between carbamazepine and erythromycin", Can. J. Physio. Pharmacol., 67:582-586 (1989).

Ukkonen et al., Birch Bark Extractive Kemia Kemi, 6:217-220 (1979).

Written Opinion of the International Searching Authority for International Application No. PCT/US05/32460 (mailed Nov. 13, 2006).

Zhao et al., "Zipper-featured δ-peptide foldamers driven by donor-acceptor interaction. Design, synthesis, and characterization", J. Org. Chem., 69:270-279 (2004).

\* cited by examiner

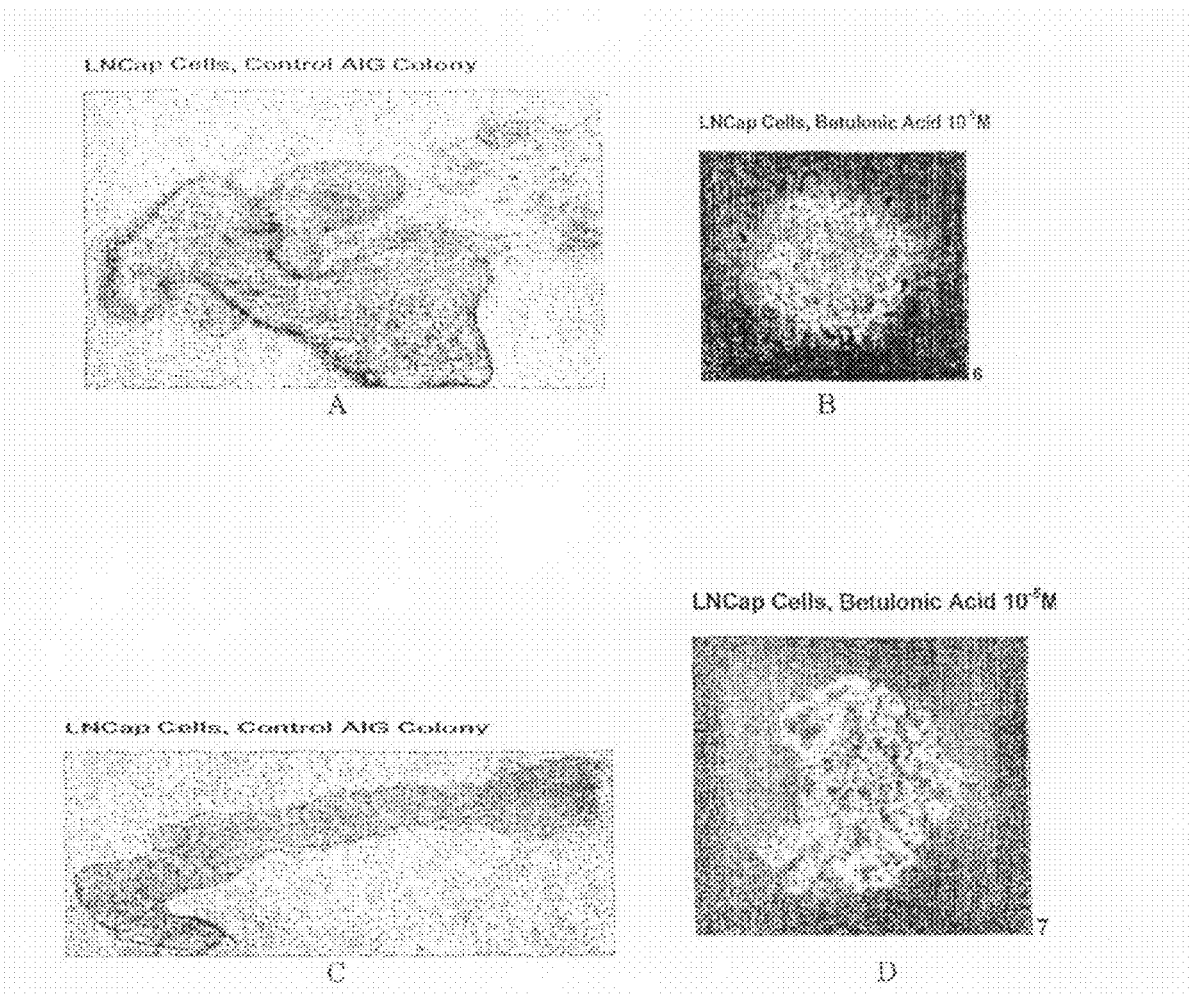
Figures 6A-D

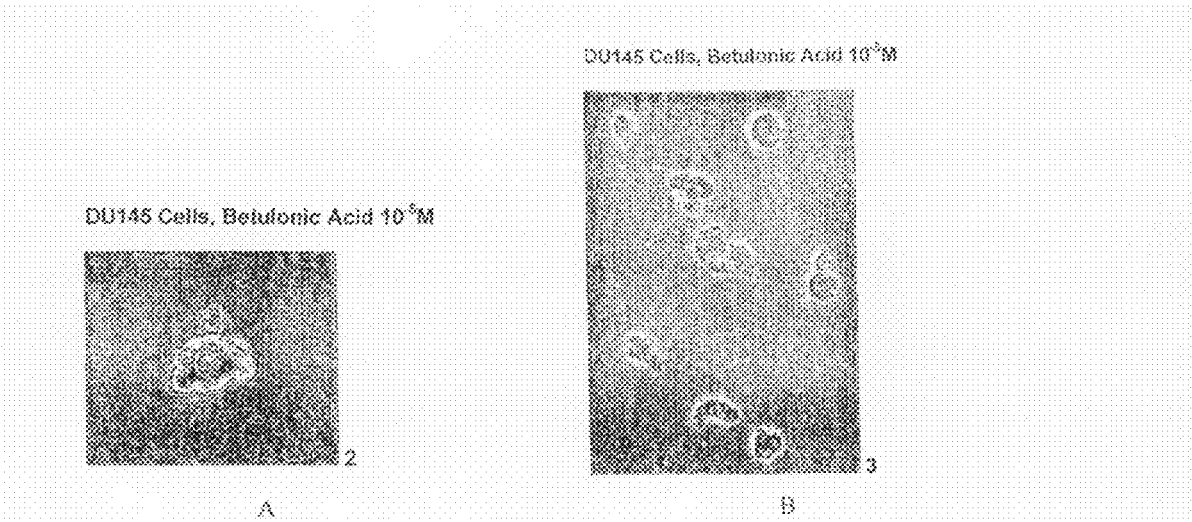
Figures 7A-B
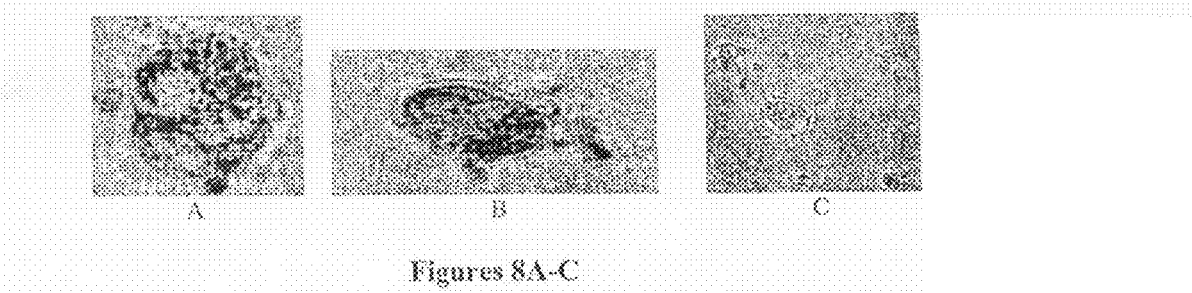
Figures 8A-C
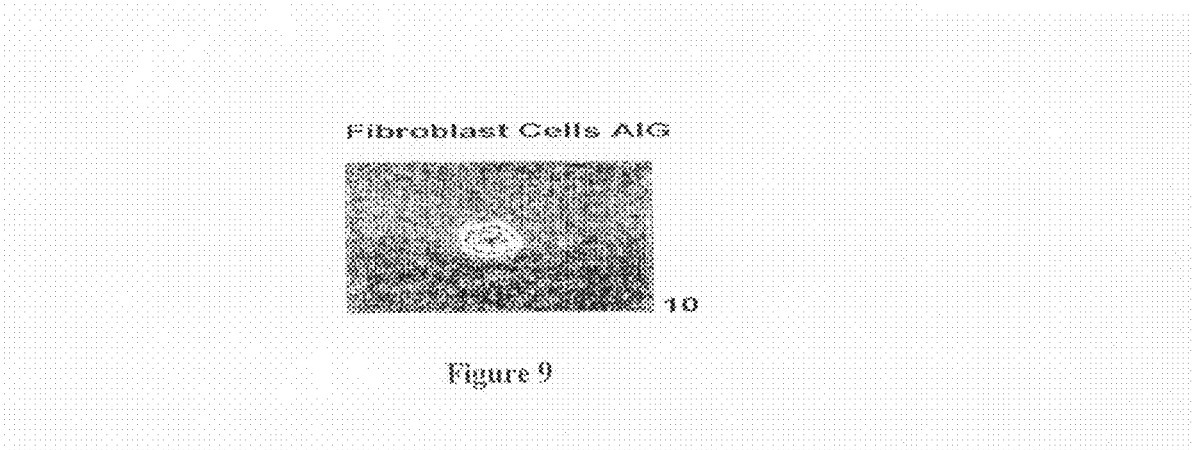
Figure 9

Figures 13A-D

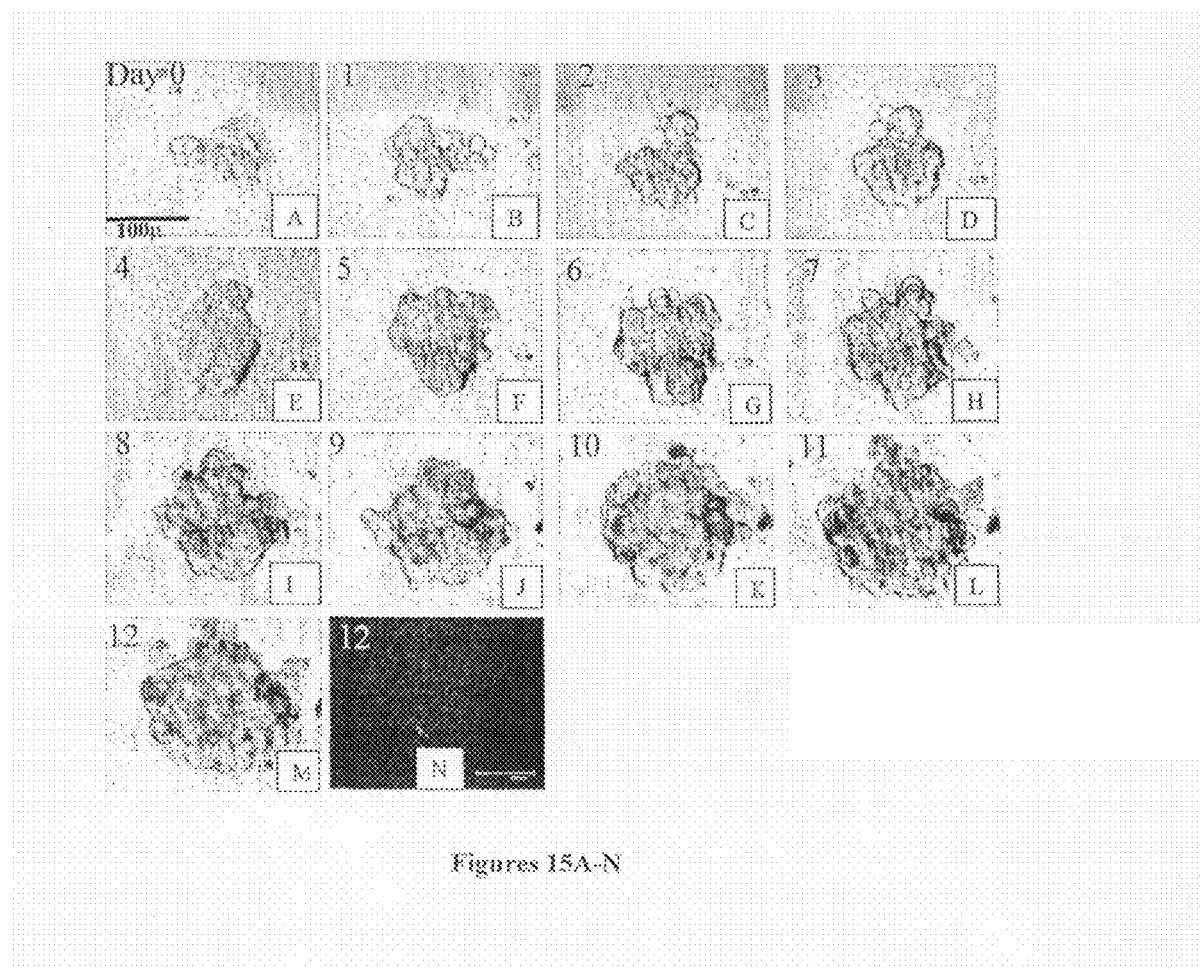
Figures 15A-N

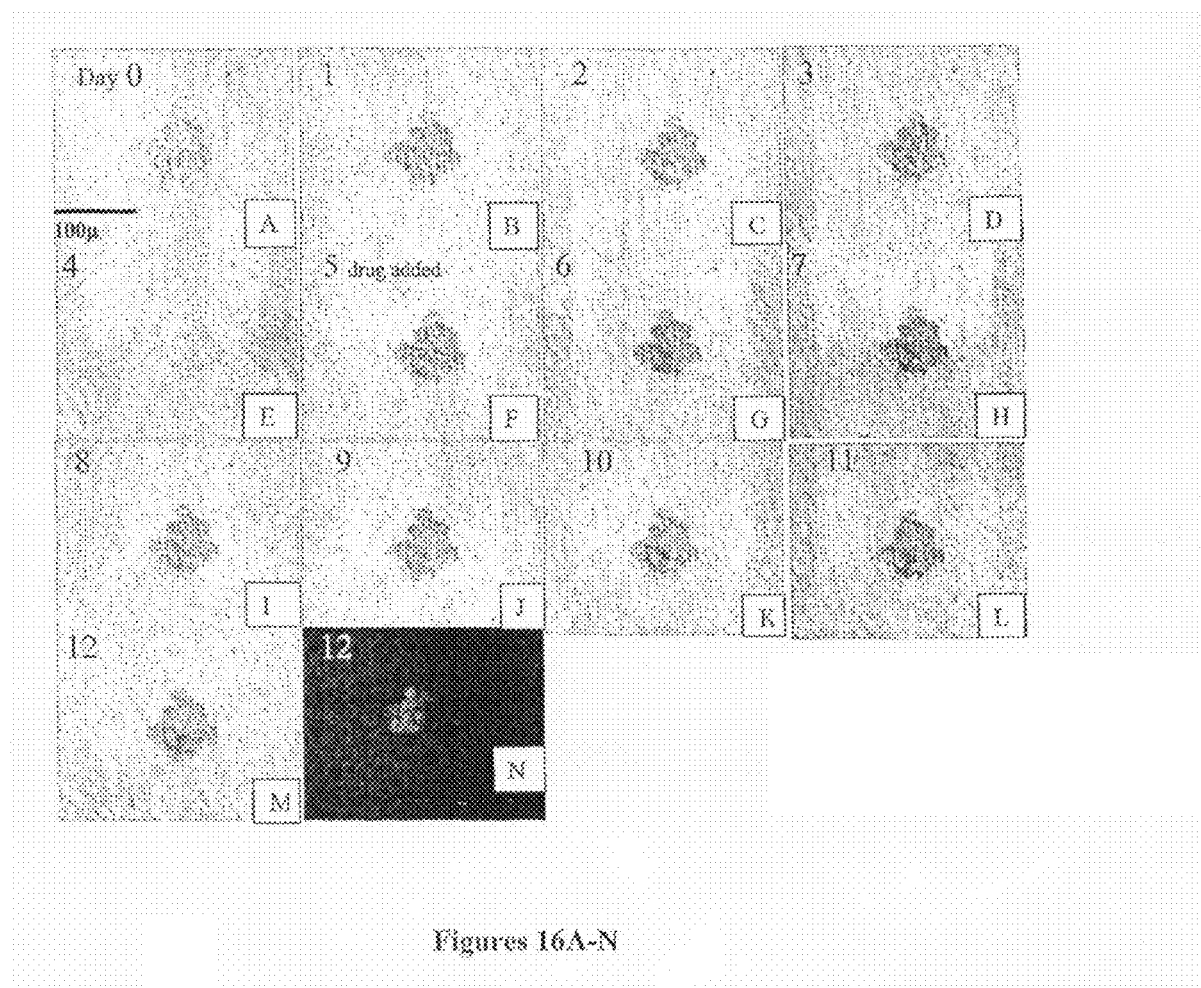
Figures 16A-N

BETULINOL DERIVATIVES AS ANTI-CANCER AGENTS

This application is a 371 of PCT/US05/32460 filed Sep. 12, 2005 which claims the priority benefit of U.S. Provisional patent application Ser. No. 60/609,080, filed Sep. 10, 2004, U.S. Provisional patent application Ser. No. 60/630,103, filed Nov. 11, 2004, and U.S. Provisional patent application Ser. No. 60/630,150, filed Nov. 11, 2004, which are hereby incorporated by reference in their entirety.

FIELD OF THE INVENTION

The present invention relates generally to methods of treating cancer as well as conjugated and immunoconjugated betulinol derivative compounds and methods of making them.

BACKGROUND OF THE INVENTION

Development of early diagnostic methods as well as drugs to treat cancer remains one of the most challenging demands on medical research. There is also an increasing interest in tumor-associated antigens as potential targets for the diagnosis and as targets for site directed drug delivery of cancer chemotherapeutic agents. Use of immunoconjugates of drugs with antibodies directed to tumor associated antigens would achieve higher bioavailability and therapeutic index of the drug, as well as diminished adverse side affects usually associated with chemotherapy.

Anti-tumor affect of pentacyclical styrene (terpenoids) has already been mentioned in the literature (Agnihotri et al., Indian J. Pharm. Sci. 2:42 (1987); Maurua et al., Fitotherapia 60:468-469 (1989); Pisha et al., Nature Medicine 1:1046 (1995); and ULkkonen et al., Birch Bark Extractive Kemia Kemi 6:217 (1979). Other lupan-row derivatives of betulinol, namely, betulinic acid, betulonic acid, betulin aldehyde, and betulon aldehyde are emerging as a new class of anticancer agents. Pentacyclic styrenes show anti-tumor activity against carcinosarcoma growth (Sheth et al., J. Pharm. Sci. 61:1819 (1972)), Epstein-Barr virus in lymphoblastoid Raji cells (Liu et al., Acta Bot. Sin. 29:84-87 (1987); Konoshima et al., J. Nat. Prod. 50:1166-1170 (1987)), and nasopharynx carcinosarcoma in vitro (Miles et al., J. Pharm. Sci. 63:613 (1974)). Pentacyclic styrenes also show anti-tumor activity against MCF-7 breast adenoma and P-333 leukemia in vitro (Kahlos Acta Pharm. Feun. 96:33 (1987)). Betulinic acid showed cytotoxic activity against carcinoma cell line CO-115 of the large intestine (LD 50=0.375 mg/ml) (Ukkonen et al., Birch Bark Extractive Kemia Kemi 6:217 (1979)). The anti-cancer activity of the terpenoids was also confirmed in vivo against Walker-256 carcinosarcoma, as tested on mice and rats. It has been suggested that betulinic acid may be the main anti-tumor agent in the mixture of terpenoids (Tomas et al., Planta Medicina 54:266-267 (1988); Jumal et al., India Chem. Soc. 61:92-93 (1964)). Betulinol and its derivatives have shown minimal adverse effect on normally proliferating cells and non-target tissues (Fulda et al., Neoplasia 7:162-170 (2005)).

Betulinol derivatives in general, and betulonic acid in particular, are soluble in a number or organic solvents such as ethanol and DMSO. However, betulonic acid and the known betulinol derivatives are generally insoluble in aqueous environment or other pharmaceutically acceptable solvents. Good solubility in an aqueous environment is an important property for a pharmaceutical agent. Absent this property, administration of the pharmaceutical agent to mammals can be difficult and biologically activity in such mammals (including humans) may be impeded or entirely absent. Due to their limited solubility in aqueous solutions, the use of terpenoids such as betulinol and it derivatives as pharmaceuticals has been limited. To be effective as a pharmaceutical agent, especially for oral ingestion, water soluble betulinol derivatives would be desirable.

The present invention is directed to overcoming these and other limitations in the art.

SUMMARY OF THE INVENTION

One aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound of Formula I

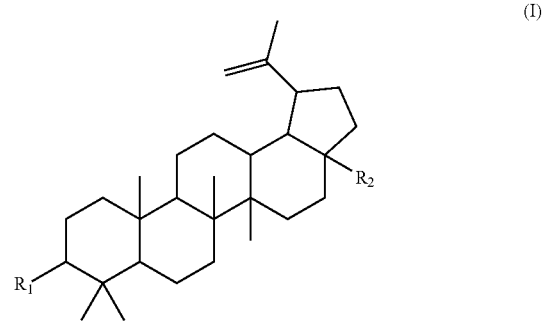

(I)

where
$R^1$ is selected from the group consisting of —$CH_3$, =O, —OH, —$OCH_3$, —OC(O)$CH_3$, —NNH-2,4-Dinitrophenyl Hydrazine ("DNP"), and =S and
$R^2$ is selected from the group consisting of —H, —$CH_3$, —CHO, —$CH_2OH$, —$CH_2OCH_3$, —$CH_2OC(O)CH_3$, —$COCH_3$, —COOH, and —CH=NNH-2,4-DNP,
or a pharmaceutically acceptable salt or derivative thereof under conditions effective to treat the cancer.

Another aspect of the present invention relates to a conjugated betulinol derivative monomer compound having the formula:

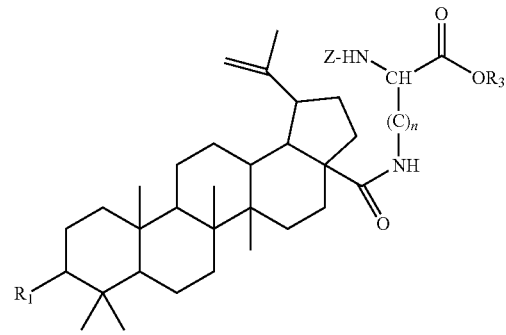

where
$R^1$ is selected from the group consisting of —$CH_3$, =O, —OH, —$OCH_3$, —OC(O)$CH_3$, —NNH-2,4-DNP, and =S;
$R_3$ is selected from the group consisting of H and $C_1$-$C_5$ alkyl;

n is an integer from 1-12; and

Z is H or a protective group or a pharmaceutically acceptable salt thereof.

As used herein in the formulas, —$(C)_n$— and —$(CH_2)_n$— both represent a saturated hydrocarbon chain of the formula —$(CH_2)_n$—.

A further aspect of the present invention relates to a method of making a conjugated betulinol derivative monomer compound as described above. This method involves reacting a reactant compound of the formula

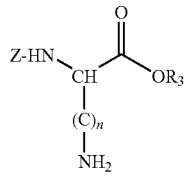

with a betulinol derivative compound of the formula

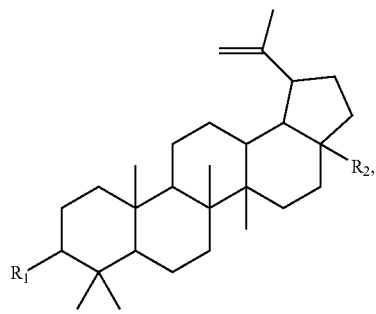

where $R_2$ is a carbonyl containing group, under conditions effective to make the conjugated betulinol derivative monomer compound.

Yet another aspect of the present invention relates to a conjugated betulinol derivative dimer compound having the formula where $Y_1$ and $Y_2$ are independently selected from the group consisting of —$CH_3$, =O, OH, —$OCH_3$, —$OC(O)CH_3$, —NNH-2,4-DNP, and =S;

$R_3$ is selected from the group consisting of H and $C_1$-$C_5$ alkyl;

Z is H or a protective group; and n is an integer from 1 to 12 or a pharmaceutically acceptable salt thereof.

Yet a further aspect of the present invention relates to a method of making a conjugated betulinol derivative dimer compound as described above. This method involves reacting reactant compounds of the formula

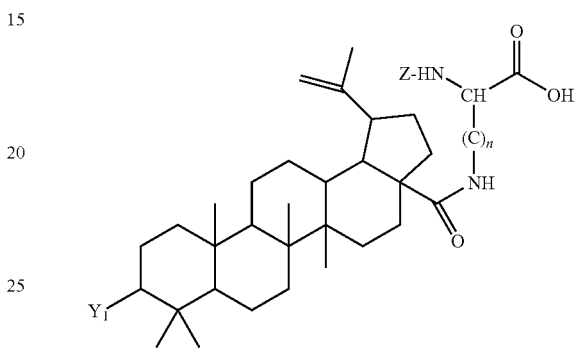

with a compound of the formula

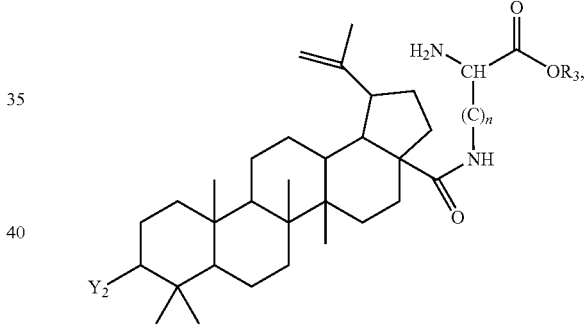

under conditions effective to make the conjugated betulinol derivative dimer compound.

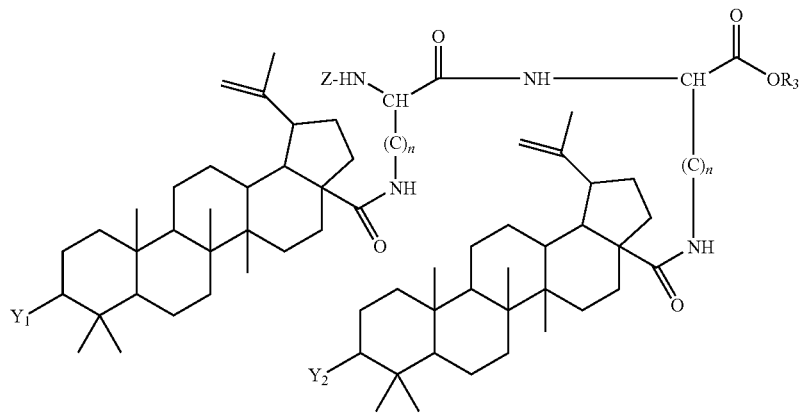

Still another aspect of the present invention relates to a conjugated betulinol derivative tetramer compound having the formula

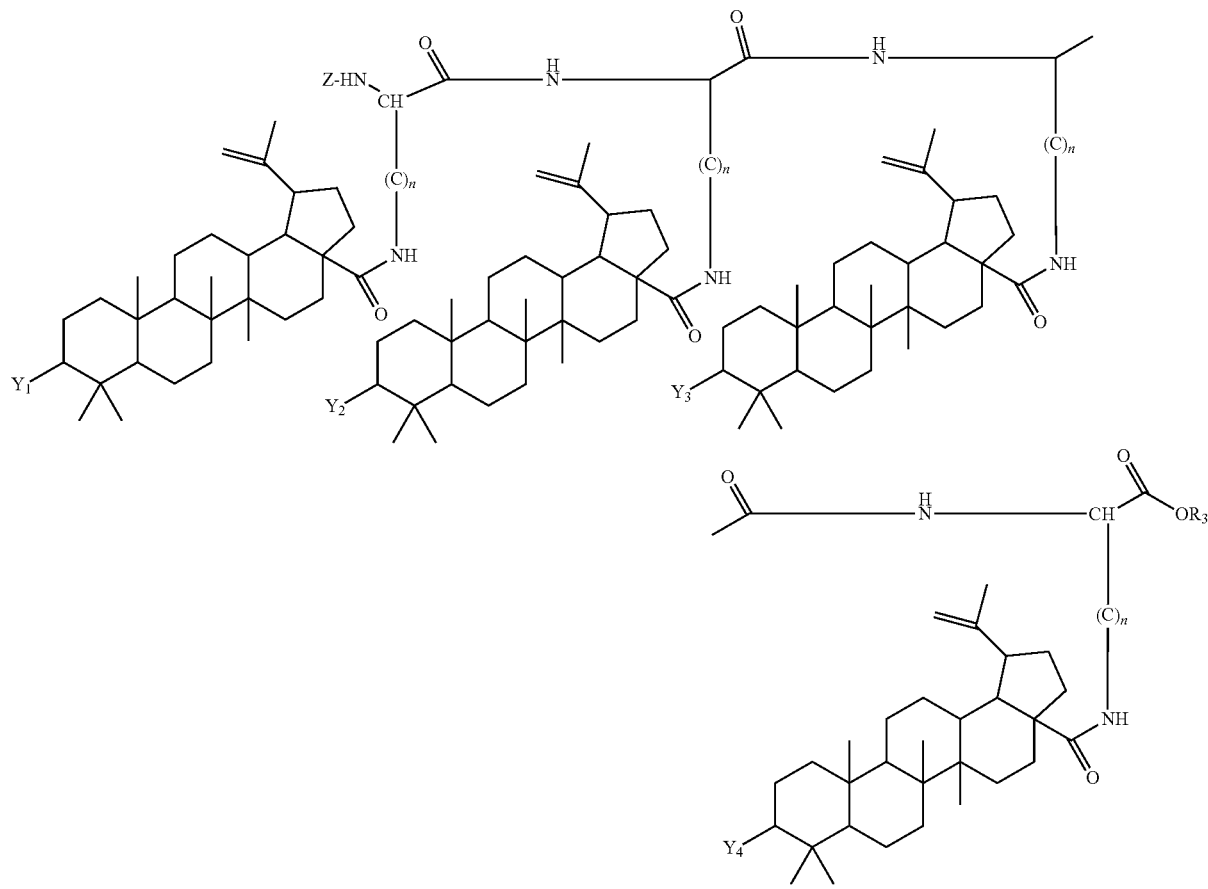

where

Y$_1$, Y$_2$, Y$_3$, and Y$_4$ are independently selected from the group consisting of —CH$_3$, =O, —OH, —OCH$_3$, —OC(O)CH$_3$, —NNH-2,4-DNP, and =S;

R$_3$ is selected from the group consisting of H and C$_1$-C$_5$ alkyl;

n is an integer from 1 to 12; and

Z is H or a protective group or a pharmaceutically acceptable salt thereof.

Still a further aspect of the present invention relates to a method of making a conjugated betulinol derivative tetramer compound as described above. This method involves reacting reactant compounds of the formula

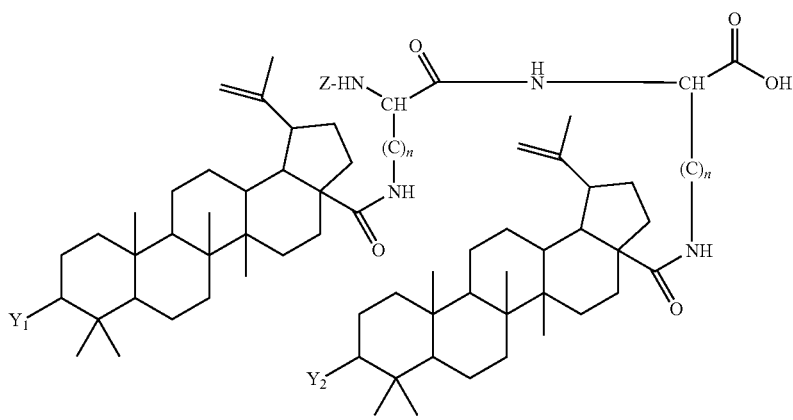

with a compound of the formula

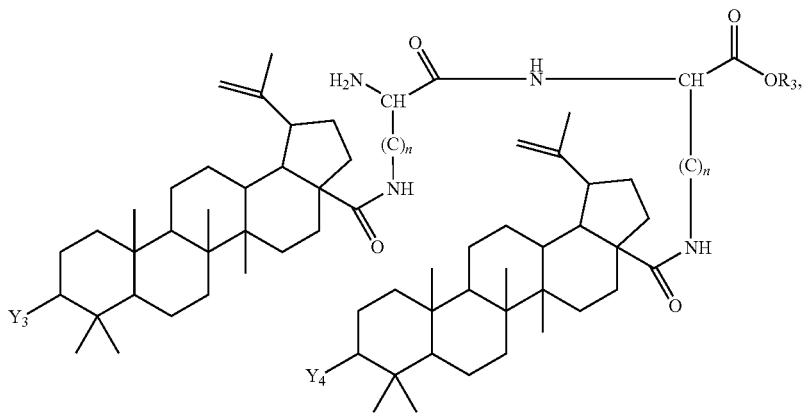

under conditions effective to make the conjugated betulinol derivative tetramer.

Another aspect of the present invention relates to a conjugated betulinol derivative polymer compound having the formula

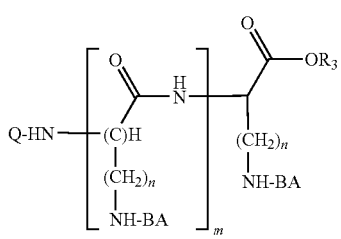

where BA is a compound having the formula

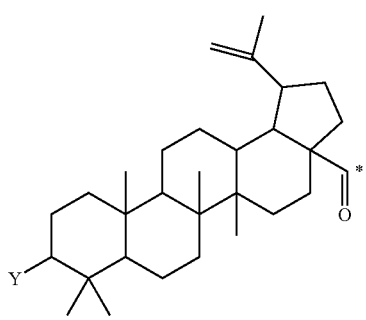

where
Y is selected from the group consisting of —$CH_3$, =O, —OH, —$OCH_3$, —OC(O)$CH_3$, —NNH-2,4-DNP, and =S;
* is a binding site;
Q is BA, a leaving group, or H;
$R_3$ is H or $C_1$-$C_5$ alkyl;
n is an integer from 1 to 12; and
m is an integer from 1 to 6
or a pharmaceutically acceptable salt thereof A further aspect of the present invention relates to a method of making a conjugated betulinol derivative polymer compound as described above. This method involves polymerizing a monomer of the formula

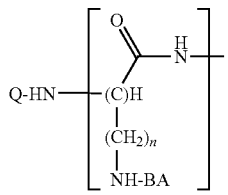

under conditions effective to make the conjugated betulinol derivative polymer compound.

Yet another aspect of the present invention relates to an immunoconjugate compound having the formula where
$R_1$ is selected from the group consisting of —$CH_3$, =O, —OH, —$OCH_3$, —OC(O)$CH_3$, —NNH-2,4-DNP, and =S;
n is an integer from 1-12; and
Z is H or a protective group
or a pharmaceutically acceptable salt thereof.

Yet a further aspect of the present invention relates to an immunoconjugate compound having the formula

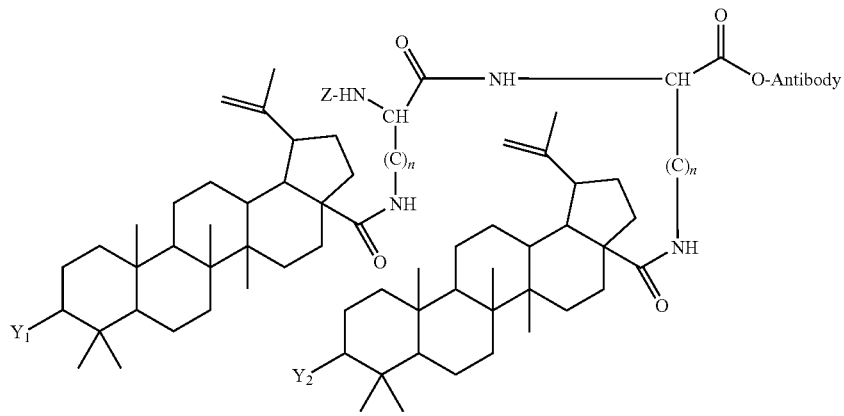

where
Y$_1$ and Y$_2$ are independently selected from the group consisting of —CH$_3$, =O, —OH, —OCH$_3$, —OC(O)CH$_3$, —NNH-2,4-DNP, and =S;
n is an integer from 1 to 12; and
Z is H or a protective group
or a pharmaceutically acceptable salt thereof.

Still another aspect of the present invention relates to an immunoconjugate compound having the formula where
Y$_1$, Y$_2$, Y$_3$, and Y$_4$ are independently selected from the group consisting of —CH$_3$, =O, —OH, —OCH$_3$, —OC(O)CH$_3$, —NNH-2,4-DNP, and =S;
n is an integer from 1 to 12; and
Z is H or a protective group
or a pharmaceutically acceptable salt thereof.

Still a further aspect of the present invention relates to an immunoconjugate compound having the formula

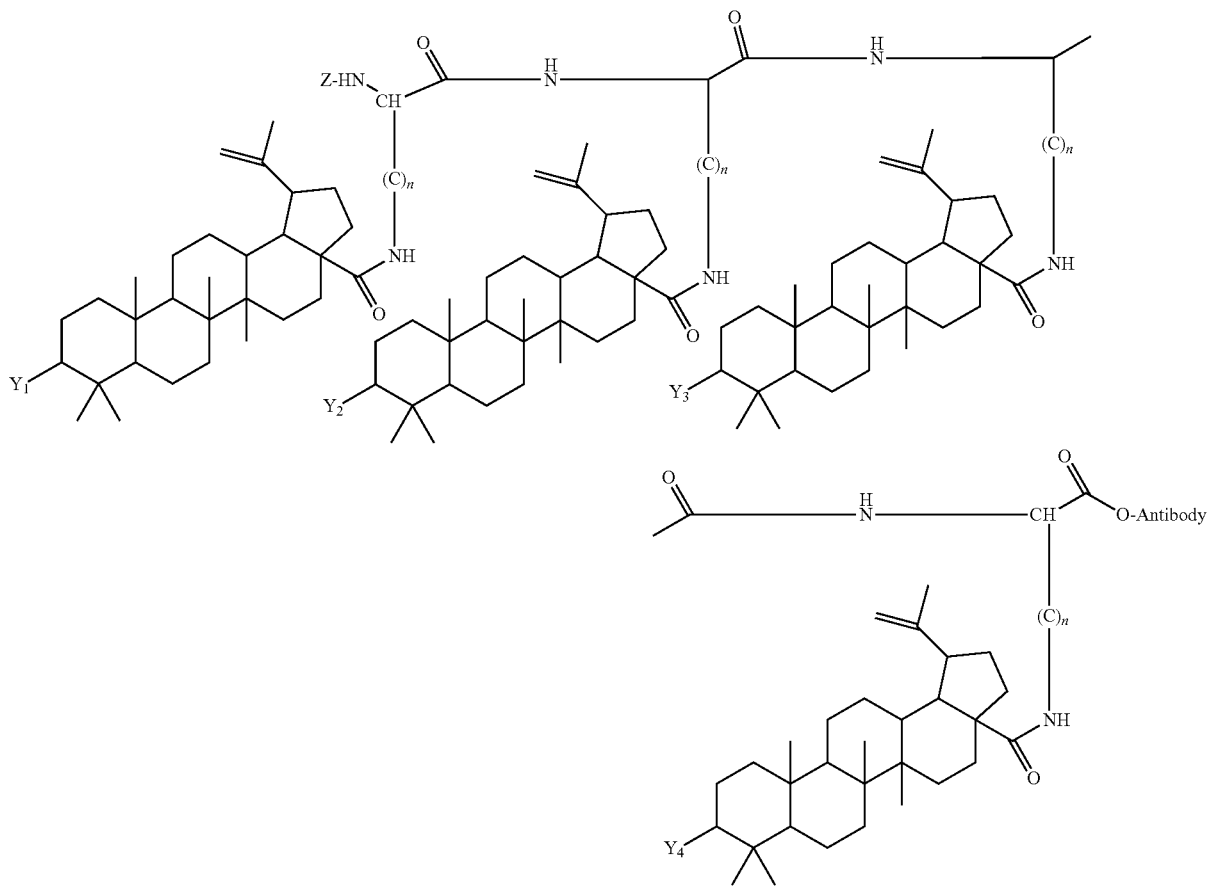

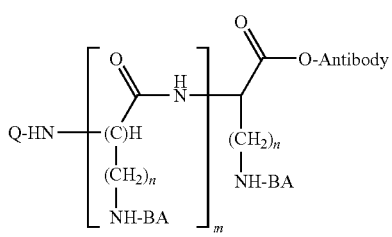

where

BA is a compound having the formula:

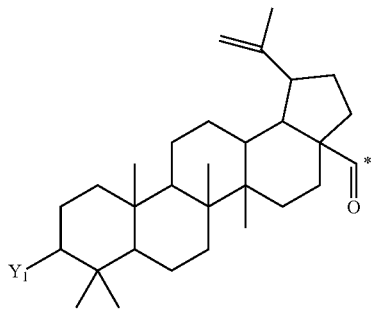

where

Y is selected from the group consisting of —CH$_3$, =O, —OH, —OCH$_3$, —OC(O)CH$_3$, —NNH-2,4-DNP, and =S;

* is a binding site;

Q is BA, a leaving group, or H;

n is an integer from 1 to 12; and m is an integer from 1 to 6 or a pharmaceutically acceptable salt thereof.

Another aspect of the present invention relates to a method of treating cancer selected from the group consisting of prostate cancer, renal cancer, breast cancer, ovarian cancer, CNS cancer, melanoma, lung cancer, and bladder cancer. This method involves administering to a subject having the cancer a monomer, dimer, tetramer, or polymer conjugated or immunoconjugated betulinol derivative compound as described above.

A further aspect of the present invention relates to a conjugated betulinol derivative having the formula:

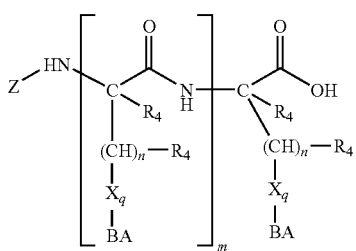

where

BA is a compound having the formula:

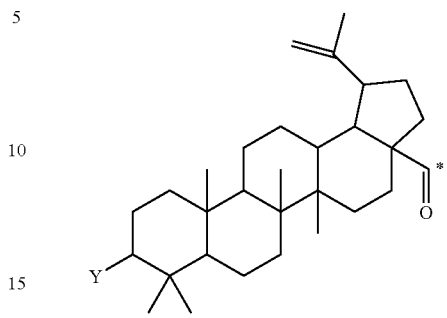

where

Y is selected from the group consisting of —CH$_3$, =O, —OH, —OCH$_3$, —OC(O)CH$_3$, —NNH-2,4-dinitrophenyl hydrazine, and =S;

* is a binding site;

X is selected from the group consisting of

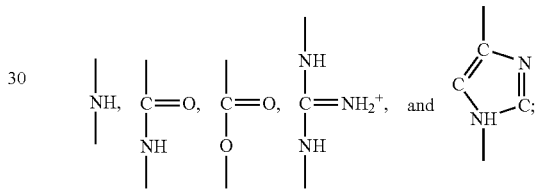

each R$_4$ is independently selected from the group consisting of H, CH$_3$, CH$_2$—CH$_3$, NH$_2$ and OH;

Z is H, a protective group, or BA;

n is an integer from 1 to 12;

m is an integer from 1 to 6; and q is 0 or 1, or a pharmaceutically acceptable salt thereof.

Yet another aspect of the present invention relates to a conjugated betulinol derivative having the formula:

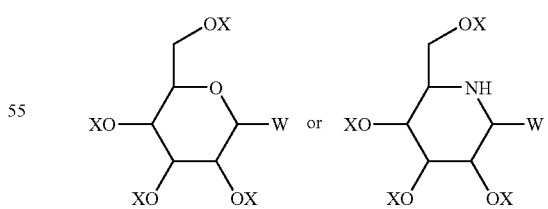

where

W is H, OX, or CH$_2$—OX; and each X is independently H, a sugar, or BA, and wherein at least 1× is BA; and BA is a compound having the formula:

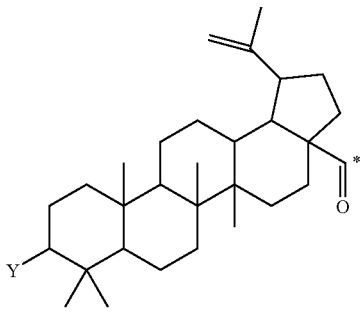

where
Y is selected from the group consisting of —CH₃, =O, —OH, —OCH₃, —OC(O)CH₃, —NNH-2,4-dinitrophenyl hydrazine, and =S; and
* is a binding site,
or a pharmaceutically acceptable salt thereof.

Yet a further aspect of the present invention relates to a conjugated betulinol derivative having the formula:

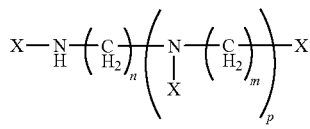

where
each X is H or a compound of the formula:

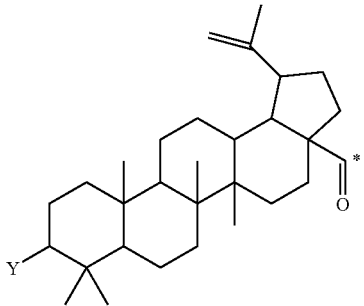

where
Y is selected from the group consisting of CH₃, =O, —OH, —OCH₃, —OC(O)CH₃, —NNH-2,4-dinitrophenyl hydrazine, and =S;
* is a binding site,
n is an integer from 1 to 8;
p is 0 or 1; and
m is an integer from 1 to 8;
where at least one X is not H,
or a pharmaceutically acceptable salt thereof.

Still another aspect of the present invention relates to a conjugated betulinol derivative of the formula:

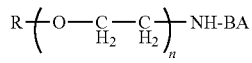

where
R is a $C_1$ to $C_5$ alkyl;
n is an integer between 5 and 1000; and
BA is a compound having the formula:

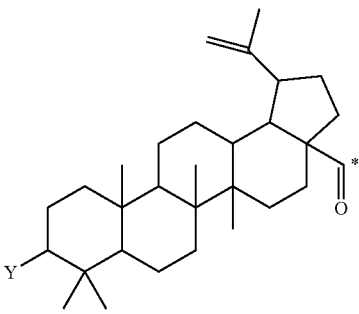

where
Y is selected from the group consisting of —CH₃, =O, —OH, —OCH₃, —OC(O)CH₃, —NNH-2,4-dinitrophenyl hydrazine, and =S; and
* is a binding site,
or a pharmaceutically acceptable salt thereof.

Still a further aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound having the formula:

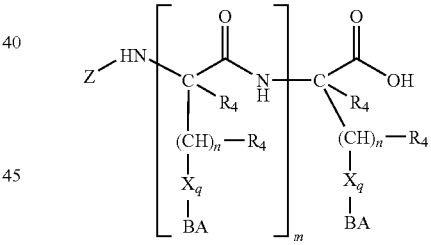

where
BA is a compound having the formula:

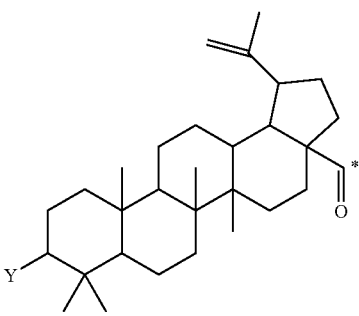

where

Y is selected from the group consisting of —CH₃, ═O, —OH, —OCH₃, —OC(O)CH₃, —NNH-2,4-dinitrophenyl hydrazine, and ═S;

\* is a binding site;

X is selected from the group consisting of

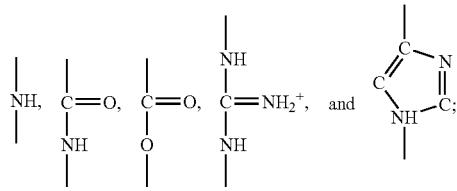

each $R_4$ is independently selected from the group consisting of H, CH₃, CH₂, CH₃, NH₂ and OH;

Z is H, a protective group, or BA;

n is an integer from 1 to 12;

m is an integer from 1 to 6; and q is 0 or 1, or a pharmaceutically acceptable salt thereof.

Another aspect of the present invention relates to a method of treating prostate cancer. This method involves administering to a human in need of such treatment a therapeutically effective amount of a compound having the formula:

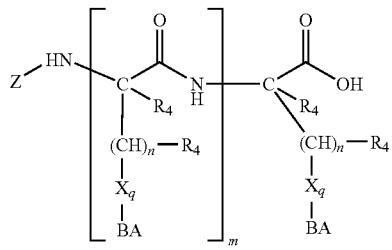

where

BA is a compound having the formula:

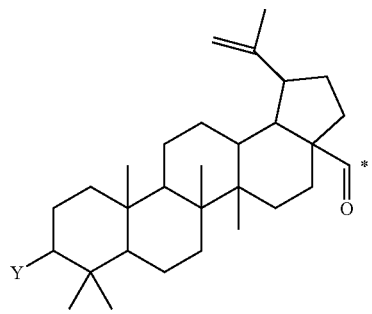

where

Y is selected from the group consisting of —CH₃, ═O, —OH, —OCH₃, —OC(O)CH₃, —NNH-2,4-dinitrophenyl hydrazine, and ═S;

\* is a binding site;

X is selected from the group consisting of

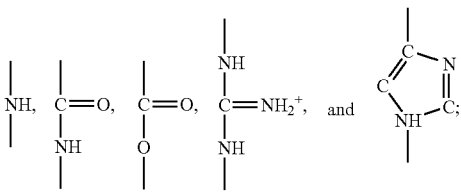

each $R_4$ is independently selected from the group consisting of H, CH₃, CH₂—CH₃, NH₂ and OH;

Z is H, a protective group, or BA;

n is an integer from 1 to 12;

m is an integer from 1 to 6; and q is 0 or 1, or a pharmaceutically acceptable salt thereof under conditions effective to treat the human for prostate cancer.

A further aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound having the formula:

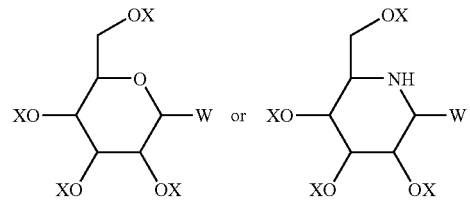

where

W is H, OX, or CH₂—OX; and each X is independently H, a sugar, or BA, and wherein at least 1× is BA;

and

BA is a compound having the formula:

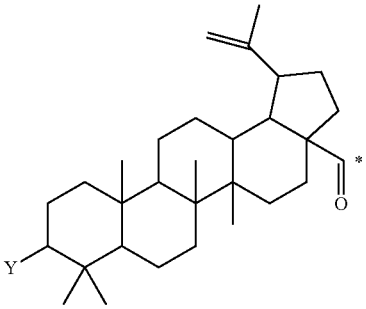

where

Y is selected from the group consisting of —CH₃, ═O, —OH, —OCH₃, —OC(O)CH₃, —NNH-2,4-dinitrophenyl hydrazine, and ═S; and \* is a binding site, or a pharmaceutically acceptable salt thereof.

Yet another aspect of the present invention relates to a method of treating prostate cancer. This method involves administering to a human in need of such treatment a therapeutically effective amount of a compound having the formula:

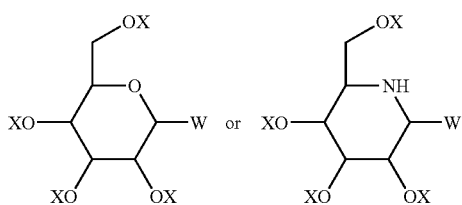

where
W is H, OX, or CH$_2$—OX; and
each X is independently H, a sugar, or BA, and wherein at least 1× is BA;
and
BA is a compound having the formula:

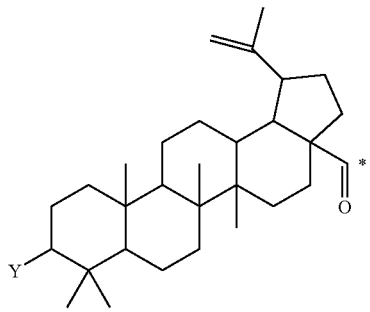

where
Y is selected from the group consisting of —CH$_3$, =O, —OH, —OCH$_3$, —OC(O)CH$_3$, —NNH-2,4-dinitrophenyl hydrazine, and =S; and
* is a binding site,
or a pharmaceutically acceptable salt thereof under conditions effective to treat the human for prostate cancer.

Yet a further aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound having the formula:

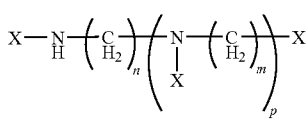

where
each X is H or a compound of the formula:

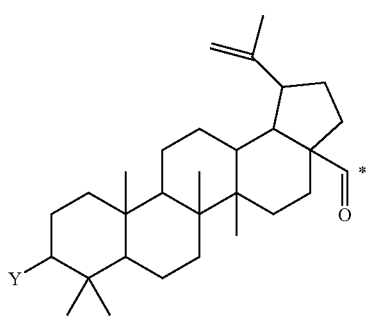

where
Y is selected from the group consisting of —CH$_3$, =O, —OH, —OCH$_3$, —OC(O)CH$_3$, —NNH-2,4-dinitrophenyl hydrazine, and =S;
* is a binding site,
n is an integer from 1 to 8;
p is 0 or 1; and
m is an integer from 1 to 8;
wherein at least one X is not H,
or a pharmaceutically acceptable salt thereof.

Still another aspect of the present invention relates to a method of treating prostate cancer. This method involves administering to a human in need of such treatment a therapeutically effective amount of a compound having the formula:

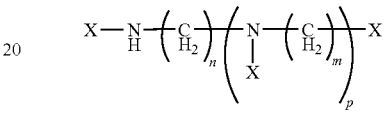

where
each X is H or a compound of the formula:

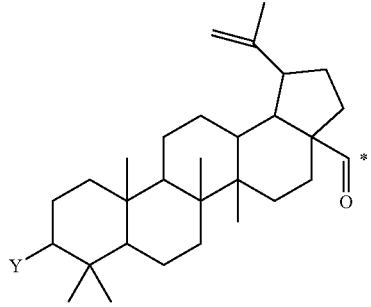

where
Y is selected from the group consisting of —CH$_3$, =O, —OH, —OCH$_3$, —OC(O)CH$_3$, —NNH-2,4-dinitrophenyl hydrazine, and =S;
* is a binding site,
n is an integer from 1 to 8;
p is 0 or 1; and
m is an integer from 1 to 8;
wherein at least one X is not H,
or a pharmaceutically acceptable salt thereof under conditions effective to treat the human for prostate cancer.

Still a further aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound having the formula:

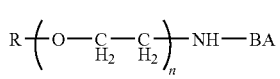

where
R is a C$_1$ to C$_5$ alkyl;
n is an integer between 5 and 1000; and

BA is a compound having the formula:

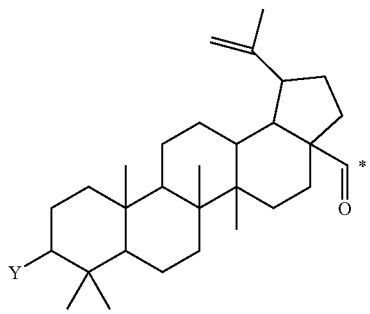

where
Y is selected from the group consisting of —CH$_3$, =O, —OH, —OCH$_3$, —OC(O)CH$_3$, —NNH-2,4-dinitrophenyl hydrazine, and =S; and
* is a binding site,
or a pharmaceutically acceptable salt thereof.

Another aspect of the present invention relates to a method of treating prostate cancer. This method involves administering to a human in need of such treatment a therapeutically effective amount of a compound having the formula:

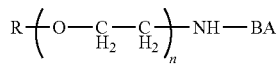

where
R is a C$_1$ to C$_5$ alkyl;
n is an integer between 5 and 1000; and
BA is a compound having the formula:

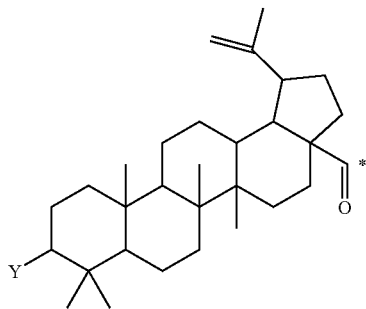

where
Y is selected from the group consisting of —CH$_3$, =O, —OH, —OCH$_3$, —OC(O)CH$_3$, —NNH-2,4-dinitrophenyl hydrazine, and =S; and
*is a binding site,
or a pharmaceutically acceptable salt thereof under conditions effective to treat the human for prostate cancer.

An advantage of betulinol derivative compounds of the present invention is that they are soluble in biocompatible solvent. This advantage allows the compounds of the present invention to be used as injectables to yield higher bioavailability as drug compounds and therefore makes them more effective in the treatment of cancerous conditions than compounds that have been previously described. The compounds of the present invention are also suitable for forming desirable ratios of drug to immunoconjugates to allow optimum dose-response.

BRIEF DESCRIPTION OF THE DRAWINGS

In FIG. 4A, the most intense peak in the ESI mass spectrum is the singly protonated ion at m/z 1261. The low level impurities with ion at m/z 581, 627, 639, and 683 are present. Since the sensitivity for the structure is low, 40 µM concentration solution was used to observe a strong m/z 1261 peak. In FIG. 4B, the predominant fragmentation process, as it was in monomer ester, is the loss of a 100 Da neutral, presumably in the form of isobutylene+CO$_2$. Among the additional, very weak, product ions those at m/z 1204 and 734 are significant, because they can be interpreted as a loss of C$_4$H$_8$ and a loss of a betulonic acid residue, respectively.

FIGS. 6A-D are photographs of LNCap cells. FIG. 6A is a photograph of a control tumor and FIG. 6B is a photograph of a tumor after treatment with betulonic acid. FIG. 6C is a photograph of a control tumor and FIG. 6D is a photograph of a tumor after treatment with betulonic acid.

FIGS. 7A-B are photographs of DU145 cells after treatment with betulonic acid.

FIGS. 8A-C are photographs of PC3 cells after treatment with betulonic acid.

FIG. 9 is a photograph of a non-transformed normal fibroblast cell line that did not form any colony, either in the control group or the treated group.

FIG. 10 shows percent increase of tumor volume from day 1 to day 10.

FIGS. 15A-N are a series of photographs showing the ex vivo growth of tumors stained with Yo-Pro-1, an immunohistochemical fluorescent indicator for apoptosis. Blue color indicates no apoptotic cells.

FIGS. 16A-N are a series of photographs showing the ex vivo growth of tumors stained with Yo-Pro-1, an immunohistochemical fluorescent indicator for apoptosis. Green color indicates apoptotic cells.

DETAILED DESCRIPTION OF THE INVENTION

Figure 1A:
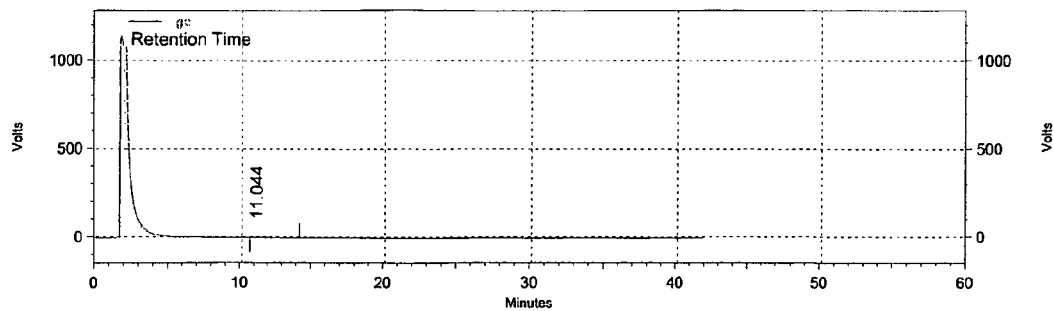
FIGS. 1A-C show chromatograms of betulonic acid and its derivatives with their corresponding retention time. Close examination of these chromatograms reveals that the betulonic acid monomer and dimer gave neat chromatograms.

One aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound of Formula I

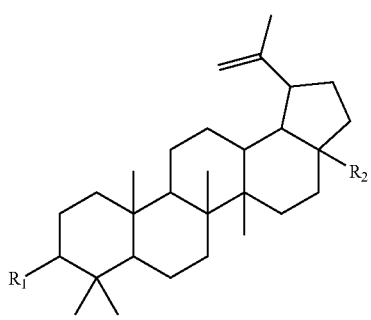

(I)

where $R^1$ is selected from the group consisting of —$CH_3$, =O, —OH, —$OCH_3$, —$OC(O)CH_3$, —NNH-2,4-Dinitrophenyl Hydrazine, and =S and $R^2$ is selected from the group consisting of —H, —$CH_3$, —CHO, —$CH_2OH$, —$CH_2OCH_3$, —$CH_2OC(O)CH_3$, —$COCH_3$, —COOH, and —CH=NNH-2,4-Dinitrophenyl Hydrazine, or a pharmaceutically acceptable salt or derivative thereof under conditions effective to treat the cancer.

According to the present invention, the compound of Formula I may, for example, have the configurations of $R_1$ and $R_2$ as shown in Table 1.

TABLE 1

Betulinol and Its Derivatives

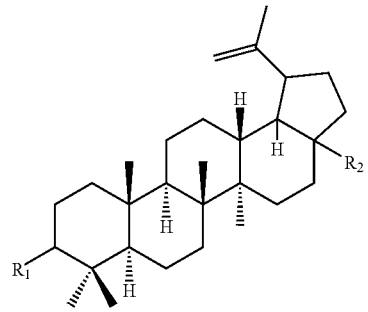

| Betulinol Derivative | $R_1$ = $R_2$ = | Formula/ Molecular Weight |
|---|---|---|
| 1. Betulinol | $R_1$—OH $R_2$—$CH_2OH$ | $C_{30}H_{50}O_2$ 442 g/mol |
| 2. Betulinic Acid | $R_1$—OH $R_2$—COOH | $C_{30}H_{48}O_3$ 456 |
| 3. Betulin Aldehyde | $R_1$—OH $R_2$—CHO | $C_{30}H_{48}O_2$ 440 |
| 4. Betulonic Acid | $R_1$=O $R_2$—COOH | $C_{30}H_{47}O_3$ 455 |
| 5. Betulon Aldehyde | $R_1$=O $R_2$—CHO | $C_{30}H_{47}O_2$ 439 |
| 6. Betulin Diacetate | $R_1$—$OCOCH_3$ $R_2$—$CH_2OCOCH_3$ | $C_{34}H_{54}O_4$ 526 |
| 7. Betulin Dimethyl ether (Cornelon) | $R_1$—$OCH_3$ $R_2$—$CH_2OCH_3$ | $C_{32}H_{54}O_2$ 470 |
| 8. 3-Acetoxy Betulin | $R_1$—$OCOCH_3$ $R_2$—OH | C32H5403 484 |
| 9. 28-Acetoxy Betulin | $R_1$—OH $R_2$—$CH_2OCOCH_3$ | $C_{32}H_{54}O_3$ 484 |
| 10. 3,28-2,4-DNP Betulin Hydrazone | $R_1$—NNH-2,4-DNP $R_2$—CH=NNH-2,4-DNP | $C_{42}H_{55}O_8N_6$ 800 |
| 11. Betulin 3-Thione | $R_1$=S $R_2$—COOH | $C_{30}H_{46}O_2S$ 470 |

According to one preferred embodiment, the compound of Formula I is betulonic acid, of the formula:

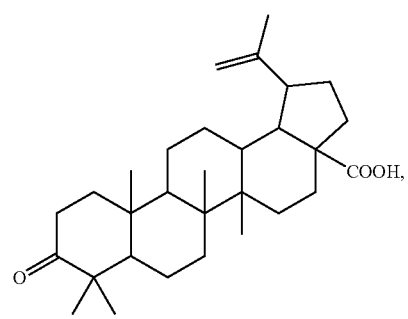

or a pharmaceutically acceptable salt or derivative thereof. Betulonic acid is a preferred compound of Formula I for treating prostate cancer, breast cancer, and/or bladder cancer.

According to another preferred embodiment, the compound of Formula I is betulin diacetate of the formula

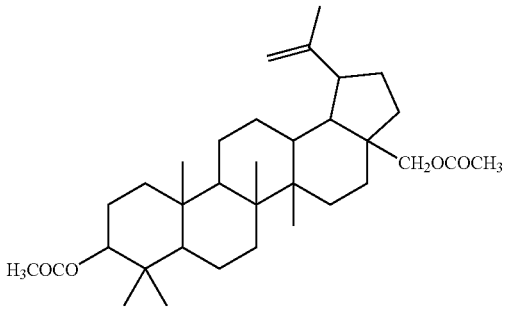

or a pharmaceutically acceptable salt or derivative thereof. Betulon diacetate is a preferred compound of Formula I for treating prostate cancer, renal cancer, breast cancer, ovarian cancer, CNS cancer, melanoma, and/or lung cancer.

According to another preferred embodiment, the compound of Formula I is betulon aldehyde of the formula

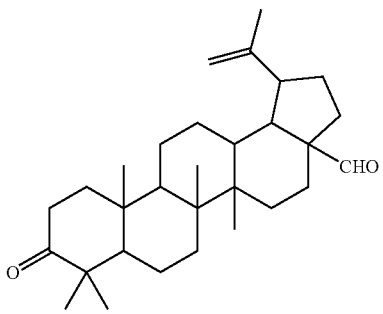

or a pharmaceutically acceptable salt or derivative thereof. Betulon aldehyde is a preferred compound of Formula I for treating breast cancer, CNS cancer, lung cancer, and/or bladder cancer.

According to another preferred embodiment, the compound of Formula I is betulinol dimethyl ether of the formula

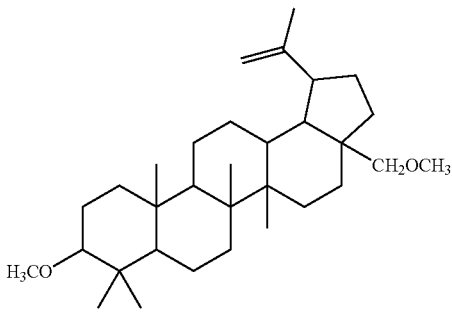

or a pharmaceutically acceptable salt or derivative thereof. Betulinol dimethyl ether is a preferred compound of Formula I for treating breast cancer, bladder cancer, CNS cancer, and/or lung cancer.

Betulinol can be isolated from the outer layer of the bark of the white birch tree *Betula alba* by sublimation (Lowitz, *Crell's Annalen* 1:312 (1788) and Mason, *Silliman's Am. J.*, 20:282 (1831), which are hereby incorporated by reference in their entirety) or by extraction with an alcohol, such as ethanol (Hunefeld, *J. Prakt. Chem.* 7:53 (1836) and Hess, *Poggendorff's Annalen* 46:319 (1839), which are hereby incorporated by reference in their entirety). Other sources of betulinol and methods for its isolation and purification have been described in, for example, Sheth et al., *J. Pharm. Sci.* 61:1819 (1972) (raw vegetables and extracts of *Hyptis emory*) and Sheth et al., *J. Pharm. Sci.* 62:139-140 (1973) (*Alnus oregonu*), which are hereby incorporated by reference in their entirety.

In a preferred method, betulinol is isolated from the non-saponifiable substance of floral soap. Briefly, the crushed initial leaf wood and components of a sulfate boiling procedure (NaOH, $Na_2SO_4$, $Na_2S_2O_3$, $Na_2SO_3$) are lodged to a boiling pot in a batch or continuous process. Under the temperature of 110° C. to 120° C. and, optionally, at increased pressure, lignin (the component of wood) dissolves. Crude cellulose is derived from the pulping liquor which is composed of lignin, cellulose, and black buck. Black buck is a composition of black buck with salts of tall acid and non-saponifiable substances. The crude cellulose is used in paper production, whereas the sulfate soap is separated from the black buck by centrifugation or by a settling process. Treatment of the sulfate soap with sulfuric acid produces tall oil. The non-saponifiable substances are separated as crude betulinol. Recrystallization of the crude betulinol, such as from acetone, ethyl acetate, isopropanol, butanol, ethanol, and the like, yields pure betulinol. The black buck residue present after centrifugation or settling can be advantageously recycled.

Betulinol derivative compounds of Formula I are synthesized by standard methods that are well known in the art. For example, detailed instructions on how to synthesize and prepare compounds of Formula I are set forth in U.S. Pat. No. 6,890,533, to Bomshteyn et al., which is hereby incorporated by reference in its entirety. The structure of betulinol is based on a 30-carbon skeleton of four, six-member rings and one five-member E-ring containing an a-isopropyl group. The structural component of betulinol has a primary and a secondary hydroxyl group at C-3 and C-28. Betulinol has three sites, at carbon 3, 20, and 28, where chemical modification can occur to yield derivatives. Synthetic schemes for the preparation of betulinol derivative compounds are described in the Examples below.

Immunoconjugates of the compounds of Formula I are also suitable in carrying out the methods of the present invention. In one embodiment, immunoconjugates are prepared by attaching an antibody directly to either $R_1$ or $R_2$ of the compound of Formula I. Alternatively, antibodies may be attached to a compound of Formula I via a spacer molecule. A detailed description of methods of attaching antibodies to betulinol and betulin-related compounds, as well as preferred immunoconjugates for carrying out the methods of the present invention, are set forth in U.S. Pat. No. 6,890,533, to Bomshteyn et al., which is hereby incorporated by reference in its entirety. For instance, one of $R_1$ or $R_2$ of the compound of Formula I may be a -peptide-Q moiety and the other of $R_1$ or $R_2$ is a hydroxy group, an alkoxy group, an alkanoyloxy group, or a -peptide-Q moiety, where Q is an -antibody-OH moiety or an —NHNH—C(O)-antibody-OH moiety. As used herein, -antibody-OH is a radical form of an antibody having the formula H-antibody-OH, where the H—denotes the amino terminus and the —OH denotes the carboxy terminus of the antibody. Thus, the antibody is bound to the -peptide moiety or to the -peptide-NHNHC(O)— moiety through its amino terminus.

A preferred type of antibody for use in the invention is an immunoglobulin which is a gammaglobulin. IgG, IgA, IgE, and IgM subclasses are particularly preferred. Some representative immunoglobulins are monoclonal or polyclonal antibodies to human or animal tumor associated antigens; human B- and T-cell antigens; human Ia antigens; viral, fungal and bacterial antigens; and cells involved in human inflammatory or allergic reactions.

Methods for preparing antibodies and monoclonal antibodies to particular haptenic or antigenic target substrates are described in Goding, *Monoclonal Antibodies: Principles and Practice,* 2nd. ed., New York:Academic Press, (1986), Kennett et al., *Monoclonal Antibodies,* New York: Plenum Press (1980); U.S. Pat. No. 4,423,147 to Secher et al.; U.S. Pat. No. 4,381,292 to Bieber et al.; U.S. Pat. No. 4,363,799 to Kung et al.; U.S. Pat. No. 4,350,683 to Galfre et al.; U.S. Pat. No. 4,127,124 to Clagett et al., which are hereby incorporated by reference.

"Treating cancer" as used herein, specifically refers to administering therapeutic agents to a subject diagnosed with cancer, i.e., having established cancer in the subject, to inhibit the further growth or spread of the malignant cells in the cancerous tissue, and/or to cause the death of the malignant cells. In particular, prostate cancer, renal cancer, breast cancer, ovarian cancer, CNS cancer, melanoma, lung cancer, and bladder cancer are amenable to the treatment in accordance with the method of the present invention. Treating cancer also encompasses treating a subject having premalignant conditions to stop the progression of, or cause regression of, the premalignant conditions. Examples of premalignant conditions include hyperplasia, dysplasia, and metaplasia.

In practicing the method of treating a cancer in a subject of the present invention, the administering step is carried out by administering an agent (i.e., a compound of Formula I) orally, intradermally, intramuscularly, intraperitoneally, intravenously, subcutaneously, or intranasally. The agent of the present invention may be administered alone or with suitable pharmaceutical carriers, and can be in solid or liquid form, such as tablets, capsules, powders, solutions, suspensions, or emulsions.

The relative activity, potency, and specificity of the compound of Formula I may be determined by a pharmacological study in animals, for example, according to the method of Nyberg et al., *Psychopharmacology* 119:345-348 (1995), which is hereby incorporated by reference in its entirety. Although the differential metabolism among patient populations can be determined by a clinical study in humans, less expensive and time-consuming substitutes are provided by the methods of Kerr et al., *Biochem. Pharmacol.* 47:1969-1979 (1994) and Karam et al., *Drub Metab. Discov.* 24:1081-1087 (1996), which are hereby incorporated by reference in their entirety. The potential for drug-drug interactions may be assessed clinically according to the methods of Leach et al., *Epilepsia* 37:1100-1106 (1996), which is hereby incorporated by reference in its entirety, or in vitro according to the methods of Kerr et al., *Biochem. Pharmacol.* 47:1969-1979 (1994) and Turner et al., *Can. J. Physio. Pharmacol.* 67:582-586 (1989), which are hereby incorporated by reference in their entirety.

The magnitude of the agent, or a pharmaceutically acceptable salt or derivative thereof, will vary with the nature and severity of the condition to be treated and the route of administration. The dose, and perhaps the dose frequency, will also vary according to the age, body weight, and response of the individual subject. The total daily dose of compounds of agents may be administered in single or divided doses.

The compound of the present invention should be administered in an effective amount. Exemplary doses of betulinol derivatives for oral administration that provide an effective amount of the betulinol derivative typically range from about 1 mg per unit dose to 2,000 mg per unit dose and more typically from about 10 mg per unit dose to 500 mg per unit dose. Preferably, the dosage is in the range of 1.0 to 200 mg/kg/day and the preferred dosage range is 1.0 to 50 mg/kg/day.

It is further recommended that children, subjects over 65 years old, and those with impaired renal or hepatic function, initially receive low doses and that the dosage be titrated based on individual responses and blood levels. It may be necessary to use dosages outside these ranges in some cases, as will be apparent to those of ordinary skill in the art. Further, it is noted that the clinician or treating physician knows how and when to interrupt, adjust, or terminate therapy in conjunction with and individual subject's response.

Pharmaceutical compositions of the present invention may include a pharmaceutically acceptable carrier, and optionally, other therapeutic ingredients or excipients.

The term "pharmaceutically acceptable salt thereof" refers to salts prepared from pharmaceutically acceptable, non-toxic acids including inorganic acids and organic acids, such as, for example, acetic acid, benzenesulfonic (besylate) acid, benzoic acids camphorsulfonic acid; citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, and p-toluenesulfonic acid.

The pharmaceutical compositions may be conveniently presented in unit dosage form, and may be prepared by any of the methods well known in the art of pharmacy. Preferred unit dosage formulations are those containing an effective dose, or an appropriate fraction thereof, of the active ingredients.

The compositions of the present invention may include a pharmaceutically acceptable carrier. The carrier may take a wide variety of forms, depending on its desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by a standard aqueous or nonaqueous technique. Oral and parenteral sustained release dosage forms may also be used.

Oral syrups, as well as other oral liquid formulations, are well known to those skilled in the art, and general methods for preparing them are found in any standard pharmacy school textbook. For example, chapter 86, of the 19th Edition of *Remington: The Science and Practice of Pharmacy*, entitled "Solutions, Emulsions, Suspensions and Extracts," describes in complete detail the preparation of syrups (pages 1503-1505, which are hereby incorporated by reference in their entirety) and other oral liquids.

Similarly, sustained release formulations are well known in the art, and Chapter 94 of the same reference, entitled "Sustained-Release Drug-Delivery Systems," describes the more common types of oral and parenteral sustained-release dosage forms (pages 1660-1675, which are hereby incorporated by reference in their entirety). Because they reduce peak plasma concentrations, as compared to conventional oral dosage forms, controlled release dosage forms are particularly useful for providing therapeutic plasma concentrations while avoiding the side effects associated with high peak plasma concentrations that occur with conventional dosage forms.

The solid unit dosage forms can be of the conventional type. The solid form can be a capsule, such as an ordinary gelatin type containing the betulinol derivative and a carrier, for example, lubricants and inert fillers, such as lactose, sucrose, or cornstarch. In another embodiment, agents can be tableted with conventional tablet bases, such as lactose, sucrose, or cornstarch, in combination with binders, like acacia, cornstarch, or gelatin, disintegrating agents, such as cornstarch, potato starch, or alginic acid, and lubricants, like stearic acid or magnesium stearate.

The pharmaceutical compositions may also be administered in injectable dosages by solution or suspension of these materials in a physiologically acceptable diluent with a pharmaceutical carrier. Such carriers include sterile liquids, such as water and oils, with or without the addition of a surfactants, adjuvants, excipients, or stabilizers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

For use as aerosols, the pharmaceutical compositions in solution or suspension may be packaged in a pressurized aerosol container together with suitable propellants, for example, hydrocarbon propellants like propane, butane, or isobutane, and with conventional adjuvants. The pharmaceutical compositions may also be administered in a non-pressurized form, such as in a nebulizer or atomizer.

Preferred subjects for treating cancer in accordance with the methods of the present invention include, without limitation, any mammal, preferably a human.

Another aspect of the present invention relates to a conjugated betulinol derivative monomer compound having the formula:

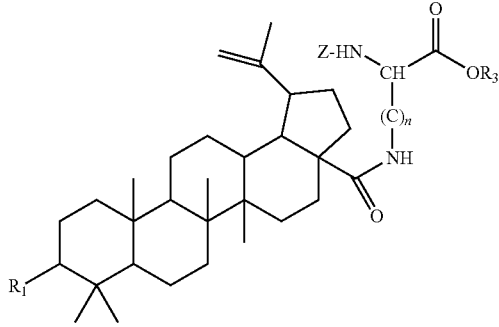

where
$R_1$ is selected from the group consisting of —$CH_3$, =O, —OH, —$OCH_3$, —$OC(O)CH_3$, —NNH-2,4-DNP, and =S;
$R_3$ is selected from the group consisting of H and $C_1$-$C_5$ alkyl;
n is an integer from 1-12; and
Z is H or a protective group
or a pharmaceutically acceptable salt thereof.

Suitable protective groups (Z) include, without limitation, a compound selected from butyloxycarbonyl and carbobenzoxy.

In a preferred embodiment, n is an integer from 2 to 8.

Preferably, the betulinol derivative monomer compound has a structure
where:
$R_1$ is =O, $R_3$ is methyl, and n is 4;
$R_1$ is =O, $R_3$ is H, Z is —C(=O)—O-t-buty 1, and n is 4; or
$R_1$ is —OH, $R_3$ is H, Z is —C(=O)—O-t-buty 1, and n is 4.
$R_1$ is =O, $R_3$ is methyl, and n=4.

A further aspect of the present invention relates to a method of making a conjugated betulinol derivative monomer compound as described above. This method involves reacting a reactant compound of the formula

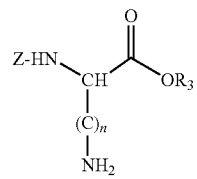

with a betulinol derivative compound of the formula

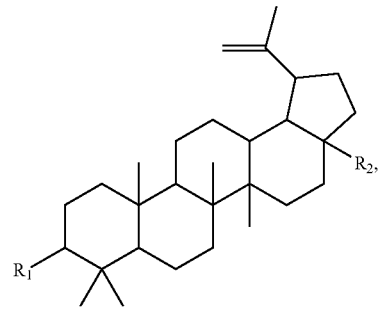

where
$R_2$ is a carbonyl containing group,
under conditions effective to make the conjugated betulinol derivative monomer compound.

In a preferred embodiment, $R_2$ is —COOH, $R_1$ is =O, $R_3$ is methyl, and n=4.

Another aspect of the present invention relates to a conjugated betulinol derivative dimer compound having the formula

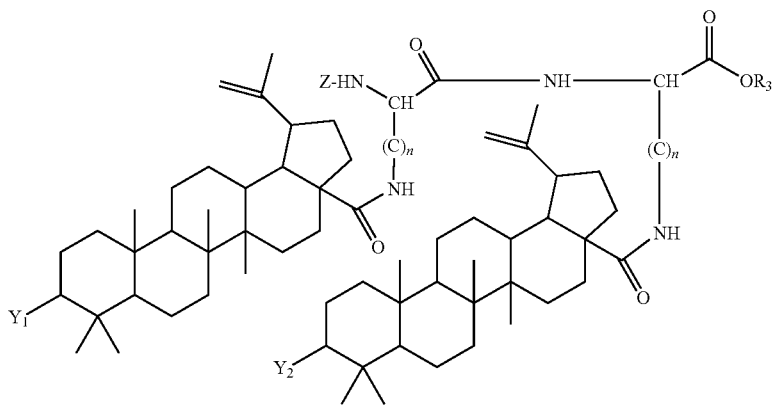

where $Y_1$ and $Y_2$ are independently selected from the group consisting of —$CH_3$, —O, —H, —$OCH_3$, —$OC(O)CH_3$, —NNH-2,4-DNP, and =S;

$R_3$ is selected from the group consisting of H and $C_1$-$C_5$ alkyl;

Z is H or a protective group; and n is an integer from 1 to 12 or a pharmaceutically acceptable salt thereof.

In a preferred embodiment, n is an integer from 2 to 8.

Preferably, the above compound has a structure where:

$Y_1$ and $Y_2$ are =O, $R_3$ is methyl, and n is 4;

$Y_1$ and $Y_2$ are =O, $R_3$ is H, Z is —C(=O)—O-t-butyl, and n is 4; or $Y_1$ and $Y_2$ are —OH, $R_3$ is H, Z is —C(=O)—O-t-butyl, and n is 4.

A further aspect of the present invention relates to a method of making a conjugated betulinol derivative dimer compound as described above. This method involves reacting reactant compounds of the formula

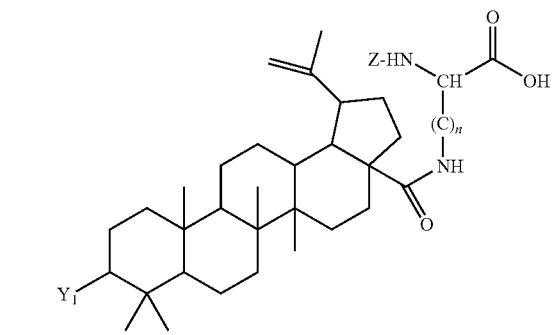

with a compound of the formula

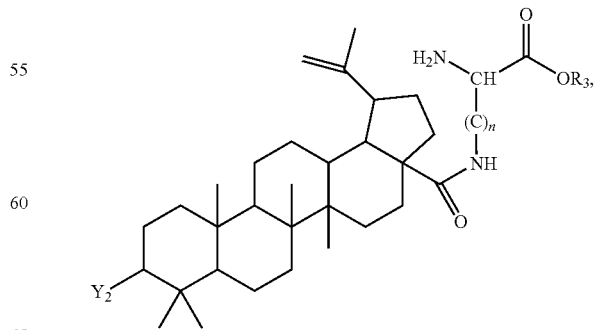

under conditions effective to make the conjugated betulinol derivative dimer compound.

Another aspect of the present invention relates to a conjugated betulinol derivative tetramer compound having the formula

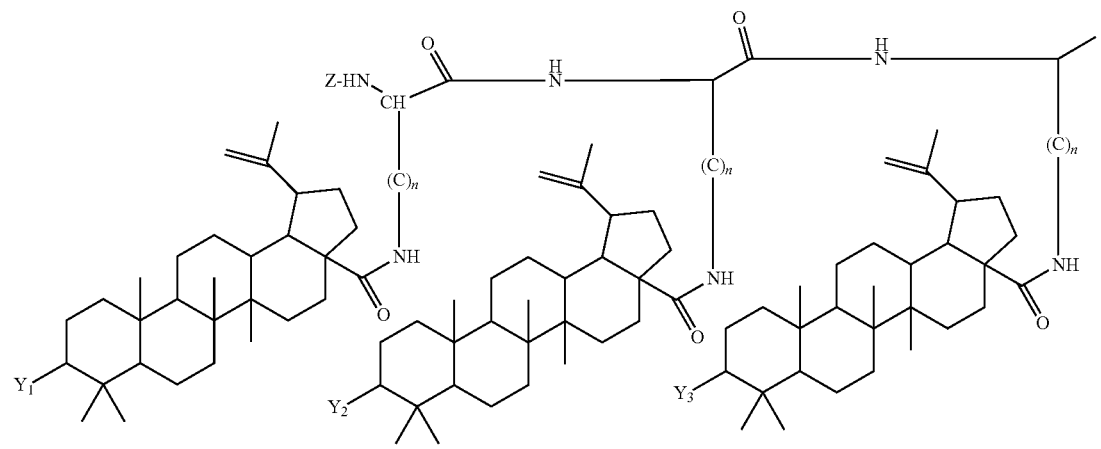

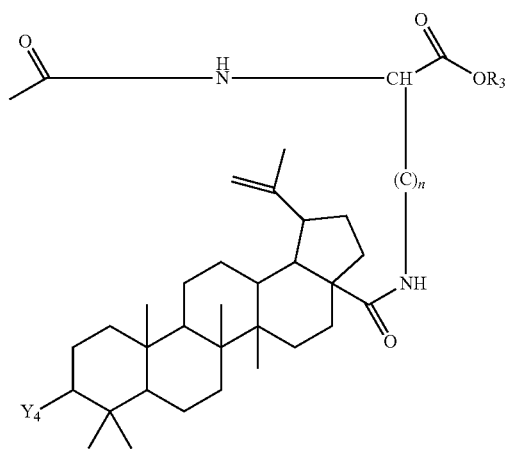

where $Y_1$, $Y_2$, $Y_3$, and $Y_4$ are independently selected from the group consisting of —$CH_3$, =O, —OH, —$OCH_3$, —OC(O)$CH_3$, —NNH-2,4-DNP, and =S;

$R_3$ is selected from the group consisting of H and $C_1$-$C_5$ allyl;

n is an integer from 1 to 12; and

Z is H or a protective group or a pharmaceutically acceptable salt thereof.

In a preferred embodiment, n is an integer from 2 to 8.

Preferably, the above compound has a structure where:

$Y_1$, $Y_2$, $Y_3$, and $Y_4$ are =O, $R_3$ is methyl, and n is 4;

$Y_1$, $Y_2$, $Y_3$, and $Y_4$ are =O, $R_3$ is H, Z is —C(=O)—O-t-buty 1, and n is 4; or $Y_1$, $Y_2$, $Y_3$, and $Y_4$ are —OH, $R_3$ is H, Z is —C(=O)—O-t-buty 1, and n is 4.

A further aspect of the present invention relates to a method of making a conjugated betulinol derivative tetramer compound as described above. This method involves reacting reactant compounds of the formula

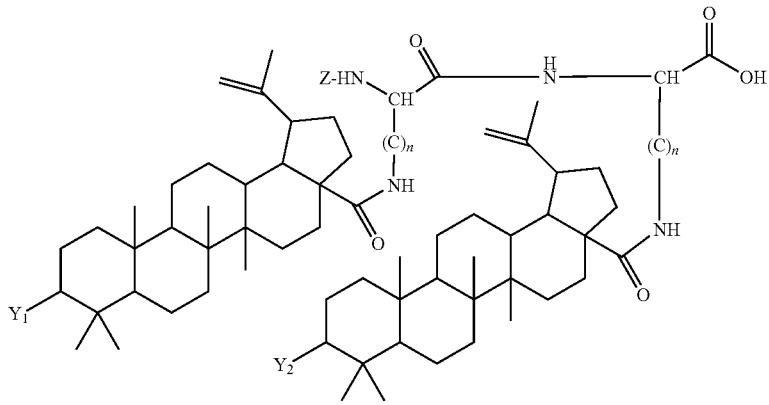

with a compound of the formula

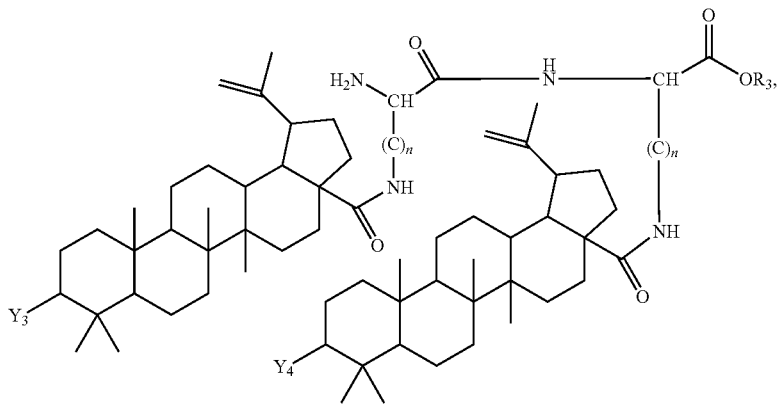

under conditions effective to make the conjugated betulinol derivative tetramer.

Another aspect of the present invention relates to a conjugated betulinol derivative polymer compound having the formula

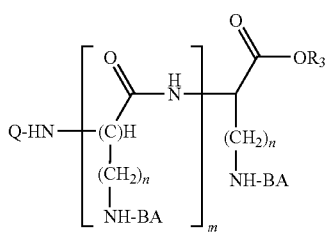

where BA is a compound having the formula

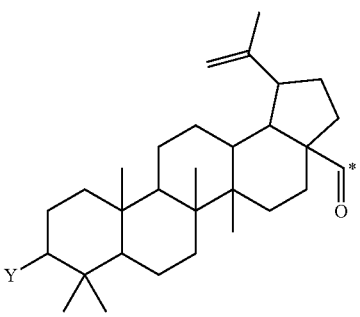

where

Y is selected from the group consisting of —$CH_3$, =O, —OH, —$OCH_3$, —$OC(O)CH_3$, —NNH-2,4-DNP, and =S;

* is a binding site;

Q is BA, a leaving group, or H;

$R_3$ is H or $C_1$-$C_5$ alkyl;

n is an integer from 1 to 12; and m is an integer from 1 to 6 or a pharmaceutically acceptable salt thereof.

In a preferred embodiment, n is an integer from 2 to 8.

Preferably, the above compound has a structure where:

Y is =O and n is 4; or

Y is —OH, Z is —C(=O)—O-t-buty 1, and n is 4.

A further aspect of the present invention relates to a method of making a conjugated betulinol derivative polymer compound as described above. This method involves polymerizing a monomer of the formula $$\left[ Q-HN - \begin{array}{c} O \\ \parallel \\ (C)H \\ | \\ (CH_2)_n \\ | \\ NH-BA \end{array} \begin{array}{c} H \\ N \end{array} \right]$$

under conditions effective to make the conjugated betulinol derivative polymer compound.

It has now been discovered that betulinol derivatives can be made more water soluble by conjugation to one or more members of a group of solubility enhancing compounds. The conjugate has a significantly greater solubility in aqueous solutions but retains a high level of biological activity including, for example, inhibitory activity against prostate cancer cells. This is particularly important since the chemistry required for making therapeutic agents more soluble often causes the biological activity of the therapeutic agent to be reduced or, in some cases, entirely lost.

Increased solubility of betulinol derivative compounds of the present invention may be achieved by a variety of other methods besides preparation of the above-described conjugates. In one preferred embodiment, increased solubility of a betulinol derivative compound is achieved by attaching a solubilizing agent at C28 or C3 of the betulin derivative. Preferred solubilizing agents include, without limitation, polyethylene glycol (PEG) or miniPEGs. PEG chemistry is well known and can be used to attach the PEG to the betulin derivative.

By another preferred embodiment, increased solubility of betulinol derivative compounds is achieved by employing hydrophilic amino acids. Specifically, the hydrophilic basic amino acids (Lys, Arg, or His) can attach to the betulin derivatives. The other highly hydrophilic amino acids (Glu, Asp, Gln, or Asn) may also be used. Di-peptides, for example, Lys-Lys, Lys-His, Lys-Arg, Arg-His, Lys-Glu, Arg-Gln, Lys-Gln, and tri-peptides may be used to enhance the solubility of the betulin derivative. Additionally, the di-peptides and tri-peptides may include amino acids that are mildly hydrophilic in character (Tyr, Trp, Ser, Thr, and Gly). The coupling of these peptides may occur in a hindered position, allow hydrophilic portion of the peptides to remain available for solvation.

The coupling of peptides, including a lysine residue, can be carried out in a manner similar to that disclosed herein for coupling lysine to a betulinol derivative with the addition of, for example, a reaction step that serves to protect the active group on the other residue(s). Similarly, amino acids or peptides containing amino acid residues having a primary or secondary amine (i.e., Arg and His) can be attached to the betulinol derivative in a manner similar to that disclosed herein for the lysine conjugation. The chemistry for forming other amino acid or peptide conjugates is well known to those skilled in the art.

In yet another preferred embodiment, polyamines such as spermidine, putrescine, and spermine may be attached to the betulin derivative to increase solubility. These compounds are attached through a primary or secondary amine group.

Carbohydrate moieties including (1) monosaccharides (e.g. glucose, galactose, fucose, and fructose), (2) disaccharides (e.g., sucrose and maltose), and (3) aminosugars (e.g., glucosamine, galactosamine, 2-amino-2-deoxy-glucuronic acid, 2-amino-2-deoxy-glucose, 2-amino-2-deoxy-3-O-α-D-glucopyranurosyl-D-galactose, galactonojirimycin, gluconojirimycin, and derivatives thereof) may also be attached to betulinol derivatives to increase solubility. Cyclodextrins, including, for example, 2-amino-2-deoxy-3-O-β-D-glucopyranurosyl-D-galactose, α-cyclodextrin (six glucose residues); β-cyclodextrin (seven glucose residues); and γ-cyclodextrin (eight glucose residues) may be attached to the betulin derivative to increase solubility.

The coupling of a carbohydrate to the betulinol derivative can be done by the methods known in the art of carbohydrate chemistry.

Increased solubility of betulinol derivative compounds may also be achieved by attaching a betulinol derivative to each of 4 glycine chains having around 2-3 glycine molecules of a sugar molecule (or 2 betulonic acid groups in the case of lysine), leaving one OH group open to attach to an antibody. In a preferred embodiment, glycine chains are used due to increased solubility in organic solution and to avoid hinderance. An exemplary structure is as follows:

where

BA〰O is BA-amino acid-O;

BA is a compound having the formula where

Y is selected from the group consisting of —CH₃, =O, —OH, —OCH₃, —OC(O)CH₃, —NNH-2,4-DNP, and =S and

* is a binding site to facilitate attachment of BA to the exemplary structure.

Alternatively, instead of leaving an OH group to bond to an antibody, it may be attached to a lipid. An exemplary structure is as follows:

where

BA〜O is BA-amino acid-O;

BA is a compound having the formula where

Y is selected from the group consisting of —CH$_3$, =O, —OH, —OCH$_3$, —OC(O)CH$_3$, —NNH-2,4-DNP, and =S;

* a binding site to facilitate attachment of BA to the exemplary structure;

p is an integer from 1 to 10;

n is an integer from 1 to 6; and m is an integer from 1 to 6.

Although there will be no conjugation with an antibody, the whole compound is water-soluble. Also, there will be no toxicity since the entire compound is biocompatible.

In another preferred embodiment, a long chain with NH$_2$ and COOH groups may be employed, alternating with an OH group at the end. These structure are achieved by attaching a betulinol derivative compound to NH$_2$ groups. The OH group can then be used to attach to an antibody. An exemplary structure is as follows:

where BA is a compound having the formula where

Y is selected from the group consisting of —CH$_3$, =O, —OH, —OCH$_3$, —OC(O)CH$_3$, —NNH-2,4-DNP, and =S;

* a binding site to facilitate attachment of BA to the exemplary structure; and n is an integer from 1 to 6.

Different ratios of carboxylic acid to the amine on the chain may be employed.

Another aspect of the present invention relates to an immunoconjugate compound having the formula where R$_1$ is selected from the group consisting of —CH$_3$, =O, —OH, —OCH$_3$, —OC(O)CH$_3$, —NNH-2,4-DNP, and =S;

n is an integer from 1-12; and

Z is H or a protective group or a pharmaceutically acceptable salt thereof.

Here, the antibody is attached to the conjugate in substantially the same manner described previously.

A further aspect of the present invention relates to an immunoconjugate compound having the formula

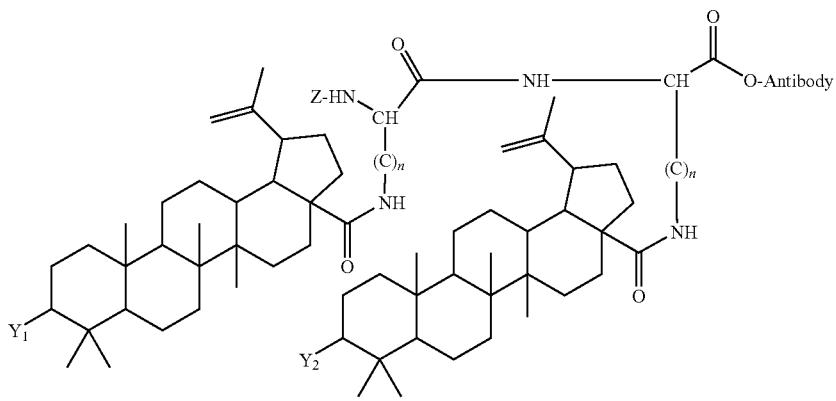

where
Y$_1$ and Y$_2$ are independently selected from the group consisting of —CH$_3$, =O, —OH, —OCH$_3$, —OC(O)CH$_3$, —NNH-2,4-DNP, and =S;
n is an integer from 1 to 12; and
Z is H or a protective group
or a pharmaceutically acceptable salt thereof.
Here, the antibody is attached to the conjugate in substantially the same manner described previously.

Another aspect of the present invention relates to an immunoconjugate compound having the formula

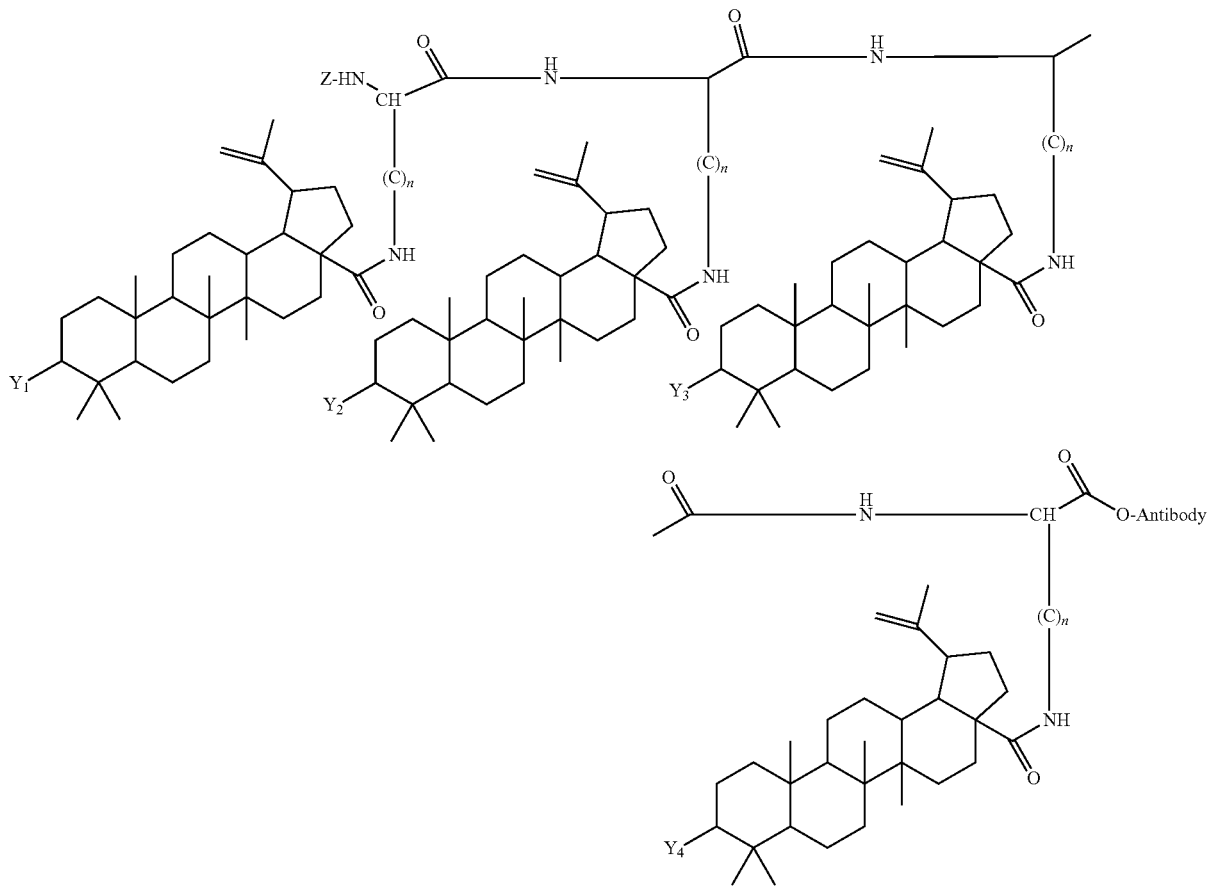

where $Y_1$, $Y_2$, $Y_3$, and $Y_4$ are independently selected from the group consisting of —$CH_3$, =O, —OH, —$OCH_3$, —OC(O)$CH_3$, —NNH-2,4-DNP, and =S;

n is an integer from 1 to 12; and

Z is H or a protective group or a pharmaceutically acceptable salt thereof.

Here, the antibody is attached to the conjugate in substantially the same manner described previously.

A further aspect of the present invention relates to an immunoconjugate compound having the formula

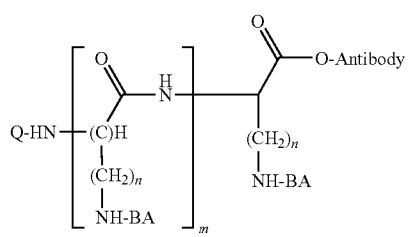

where

BA is a compound having the formula:

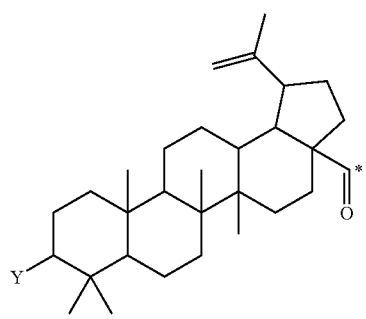

where

Y is selected from the group consisting of —$CH_3$, =O, —OH, —$OCH_3$, —OC(O)$CH_3$, —NNH-2,4-DNP, and =S;

* is a binding site;

Q is BA, a leaving group, or H;

n is an integer from 1 to 12; and m is an integer from 1 to 6 or a pharmaceutically acceptable salt thereof.

Here, the antibody is attached to the conjugate in substantially the same manner described previously.

A further aspect of the present invention relates to a method of treating cancer selected from the group consisting of prostate cancer, renal cancer, breast cancer, ovarian cancer, CNS cancer, melanoma, lung cancer, and bladder cancer. This method involves administering to a subject having the cancer a monomer, dimer, tetramer, or polymer conjugated betulinol derivative compound, or immunoconjugate compound, as described above, or a pharmaceutically acceptable salt or derivative thereof under conditions effective to treat the cancer. In carrying out this aspect of the present invention, the above-described formulations and modes of administration are utilized.

Another aspect of the present invention relates to a conjugated betulinol derivative having the formula:

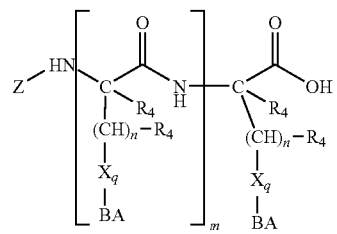

where

BA is a compound having the formula:

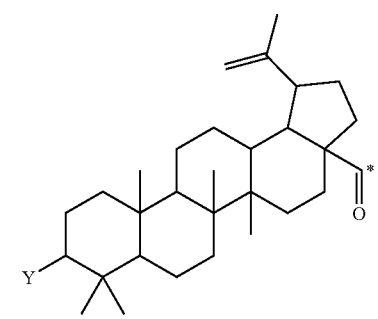

where

Y is selected from the group consisting of —$CH_3$, =O, —OH, —$OCH_3$, —OC(O)$CH_3$, —NNH-2,4-dinitrophenyl hydrazine, and =S;

* is a binding site;

X is selected from the group consisting of

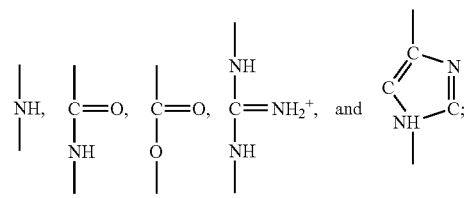

each $R_4$ is independently selected from the group consisting of H, $CH_3$, $CH_2$—$CH_3$, $NH_2$ and OH;

Z is H, a protective group, or BA;

n is an integer from 1 to 12;

m is an integer from 1 to 6; and q is 0 or 1, or a pharmaceutically acceptable salt thereof.

A further aspect of the present invention relates to a conjugated betulinol derivative having the formula:

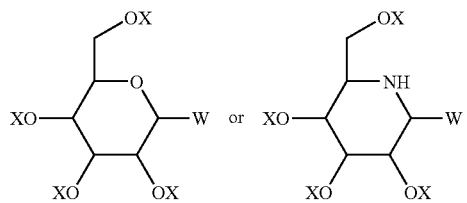

where
W is H, OX, or CH$_2$—OX; and
each X is independently H, a sugar, or BA, and wherein at least 1× is BA; and
BA is a compound having the formula:

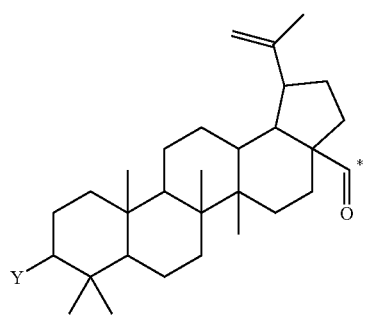

where
Y is selected from the group consisting of —CH$_3$, =O, —OH, —OCH$_3$, —OC(O)CH$_3$, —NNH-2,4-dinitrophenyl hydrazine, and =S; and
* is a binding site,
or a pharmaceutically acceptable salt thereof.

Yet another aspect of the present invention relates to a conjugated betulinol derivative having the formula:

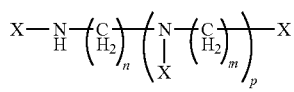

where
each X is H or a compound of the formula:

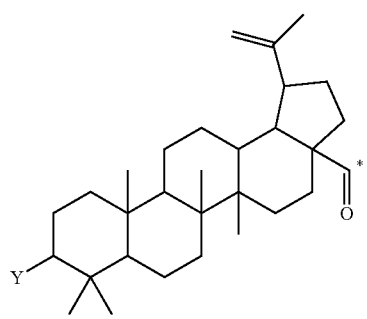

where
Y is selected from the group consisting of —CH$_3$, =O, —OH, —OCH$_3$, —OC(O)CH$_3$, —NNH-2,4-dinitrophenyl hydrazine, and =S;
* is a binding site,
n is an integer from 1 to 8;
p is 0 or 1; and
m is an integer from 1 to 8;
where at least one X is not H,
or a pharmaceutically acceptable salt thereof.

In a preferred embodiment, the above compound has a structure where:
n=4 and p=0 or
n=4, p=1, and m=3.

Yet a further aspect of the present invention relates to a conjugated betulinol derivative of the formula:

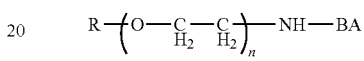

where
R is a C$_1$ to C$_5$ alkyl;
n is an integer between 5 and 1000; and
BA is a compound having the formula:

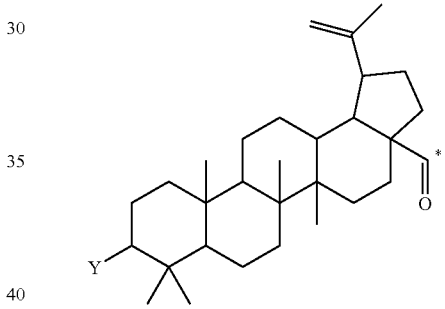

where
Y is selected from the group consisting of —CH$_3$, =O, —OH, —OCH$_3$, —OC(O)CH$_3$, —NNH-2,4-dinitrophenyl hydrazine, and =S; and
* is a binding site,
or a pharmaceutically acceptable salt thereof.

Still another aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound having the formula:

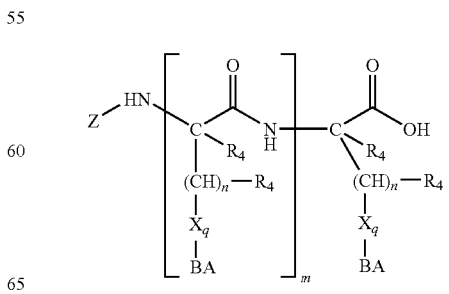

where

BA is a compound having the formula:

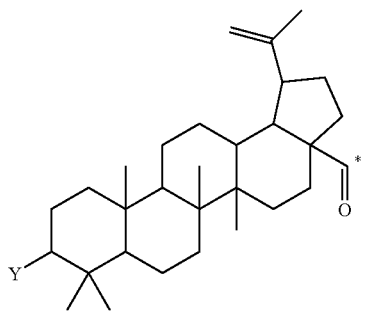

where

Y is selected from the group consisting of —CH$_3$, =O, —OH, —OCH$_3$, OC(O)CH$_3$, —NNH-2,4-dinitrophenyl hydrazine, and =S;

\* is a binding site;

X is selected from the group consisting of

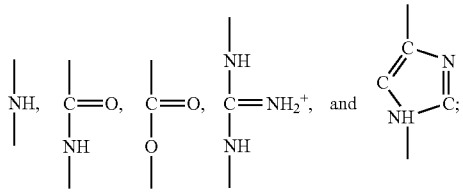

each R$_4$ is independently selected from the group consisting of H, CH$_3$, CH$_2$—CH$_3$, NH$_2$ and OH;

Z is H, a protective group, or BA;

n is an integer from 1 to 12;

m is an integer from 1 to 6; and q is 0 or 1, or a pharmaceutically acceptable salt thereof.

Still a further aspect of the present invention relates to a method of treating prostate cancer. This method involves administering to a human in need of such treatment a therapeutically effective amount of a compound having the formula:

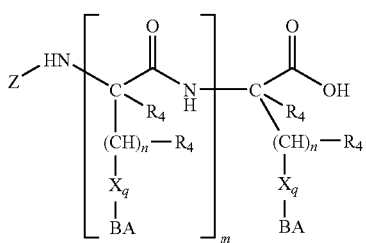

where

BA is a compound having the formula:

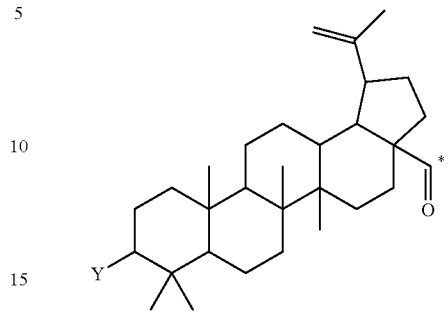

where

Y is selected from the group consisting of —CH$_3$, =O, —OH, —OCH$_3$, —OC(O)CH$_3$, —NNH-2,4-dinitrophenyl hydrazine, and =S;

\* is a binding site;

X is selected from the group consisting of

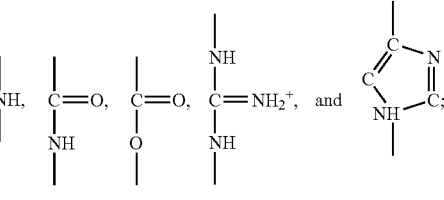

each R$_4$ is independently selected from the group consisting of H, CH$_3$, CH$_2$—CH$_3$, NH$_2$ and OH;

Z is H, a protective group, or BA;

n is an integer from 1 to 12;

m is an integer from 1 to 6; and q is 0 or 1, or a pharmaceutically acceptable salt thereof under conditions effective to treat the human for prostate cancer.

Another aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound having the formula:

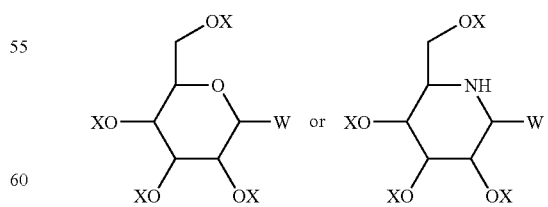

where

W is H, OX, or CH$_2$—OX; and each X is independently H, a sugar, or BA, and wherein at least 1× is BA;

and
BA is a compound having the formula:

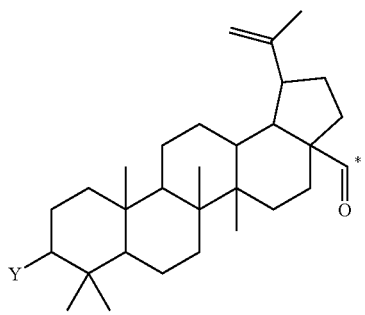

where
Y is selected from the group consisting of CH₃, =O, —OH, —OCH₃, —OC(O)CH₃, —NNH-2,4-dinitrophenyl hydrazine, and =S; and
* is a binding site,
or a pharmaceutically acceptable salt thereof.

A further aspect of the present invention relates to a method of treating prostate cancer. This method involves administering to a human in need of such treatment a therapeutically effective amount of a compound having the formula:

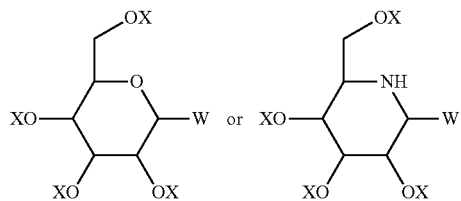

where
W is H, OX, or CH₂—OX; and
each X is independently H, a sugar, or BA, and wherein at least 1× is BA;
and
BA is a compound having the formula:

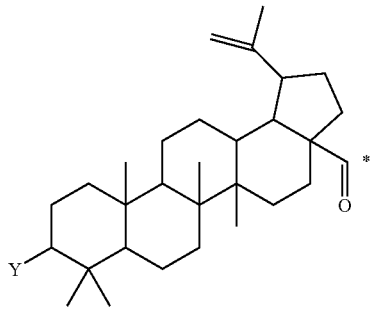

where
Y is selected from the group consisting of —CH₃, =O, —OH, —OCH₃, —OC(O)CH₃, —NNH-2,4-dinitrophenyl hydrazine, and =S; and
* is a binding site,
or a pharmaceutically acceptable salt thereof under conditions effective to treat the human for prostate cancer.

Yet another aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound having the formula:

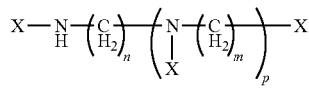

where
each X is H or a compound of the formula:

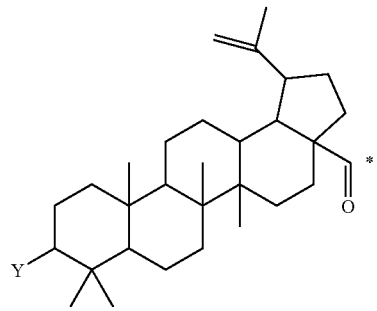

where
Y is selected from the group consisting of —CH₃, =O, —OH, —OCH₃, —OC(O)CH₃, —NNH-2,4-dinitrophenyl hydrazine, and =S;
* is a binding site,
n is an integer from 1 to 8;
p is 0 or 1; and
m is an integer from 1 to 8;
wherein at least one X is not H,
or a pharmaceutically acceptable salt thereof.

Yet a further aspect of the present invention relates to a method of treating prostate cancer. This method involves administering to a human in need of such treatment a therapeutically effective amount of a compound having the formula:

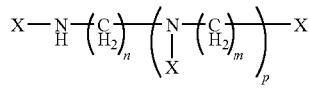

where
each X is H or a compound of the formula:

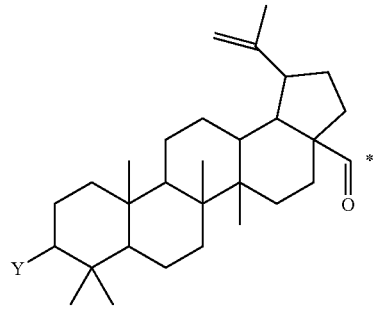

where
Y is selected from the group consisting of —CH$_3$, =O, —OH, —OCH$_3$, —OC(O)CH$_3$, —NNH-2,4-dinitrophenyl hydrazine, and =S;
\* is a binding site,
n is an integer from 1 to 8;
p is 0 or 1; and
m is an integer from 1 to S;
wherein at least one X is not H,
or a pharmaceutically acceptable salt thereof under conditions effective to treat the human for prostate cancer.

Still another aspect of the present invention relates to a method of treating a cancer selected from the group consisting of prostate cancer, renal cancer, breast cancer, ovarian cancer, CNS cancer, melanoma, lung cancer, and bladder cancer. This method involves administering to a subject having the cancer a compound having the formula:

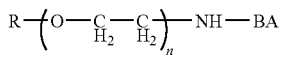

where
R is a C$_1$ to C$_5$ alkyl;
n is an integer between 5 and 1000; and
BA is a compound having the formula:

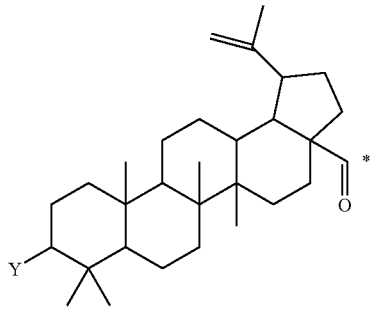

where
Y is selected from the group consisting of —CH$_3$, =O, —OH, —OCH$_3$, —OC(O)CH$_3$, —NNH-2,4-dinitrophenyl hydrazine, and =S; and
\* is a binding site,
or a pharmaceutically acceptable salt thereof.

Still a further aspect of the present invention relates to a method of treating prostate cancer. This method involves administering to a human in need of such treatment a therapeutically effective amount of a compound having the formula:

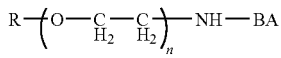

where
R is a C$_1$ to C$_5$ alkyl;
n is an integer between 5 and 1000; and
BA is a compound having the formula:

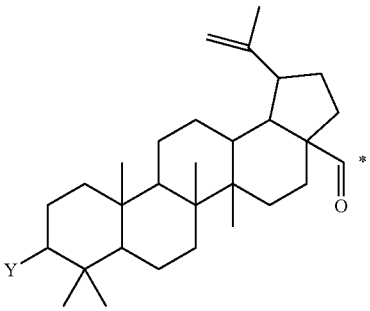

where
Y is selected from the group consisting of —CH$_3$, =O, —OH, —OCH$_3$, —OC(O)CH$_3$, —NNH-2,4-dinitrophenyl hydrazine, and =S; and
\* is a binding site,
or a pharmaceutically acceptable salt thereof under conditions effective to treat the human for prostate cancer.

EXAMPLES

The examples below are intended to exemplify the practice of the present invention but are by no means intended to limit the scope thereof.

Example 1

Isolation and Structure of Betulinol and its Derivatives

Betulinol is isolated from the non-saponoflable fraction of the crude sulfate soap prepared by boiling the outer bark of the white birch tree in NaOH, Na$_2$SO$_4$, Na$_2$SO$_3$, and Na$_2$S$_2$O$_3$ at 110-120° C. Betulinol is then crystallized by using solvents such as acetone, ethyl acetate, isopropanol, butanol, ethanol, etc. The chemical structure of betulinol is:

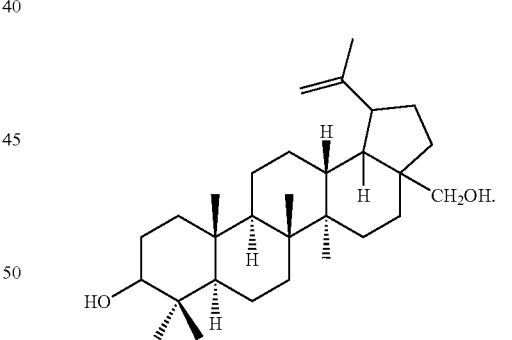

Betulinol is a non-steroidal, lupeol-derived, pentacyclical, lupan-row alcohol of the group of styrenes. Betulinol (also known as betulin) has a chemical formula of C$_{30}$H$_{50}$O$_2$ and a molecular weight of 442.7 g/mol. The structure of betulinol is based on a 30-carbon skeleton of four, six-member rings and one, five-member E-ring containing an a-isopropyl group. The structural component of betulinol has a primary and a secondary hydroxyl group at C-3 and C-28. Betulinol has three sites (C-3, C-20, and C-28) where chemical modification can occur to yield derivatives. With the availability of betulinol and its ability to react with various other organic compounds, eleven derivatives of betulinol were synthesized as shown in Scheme 1.

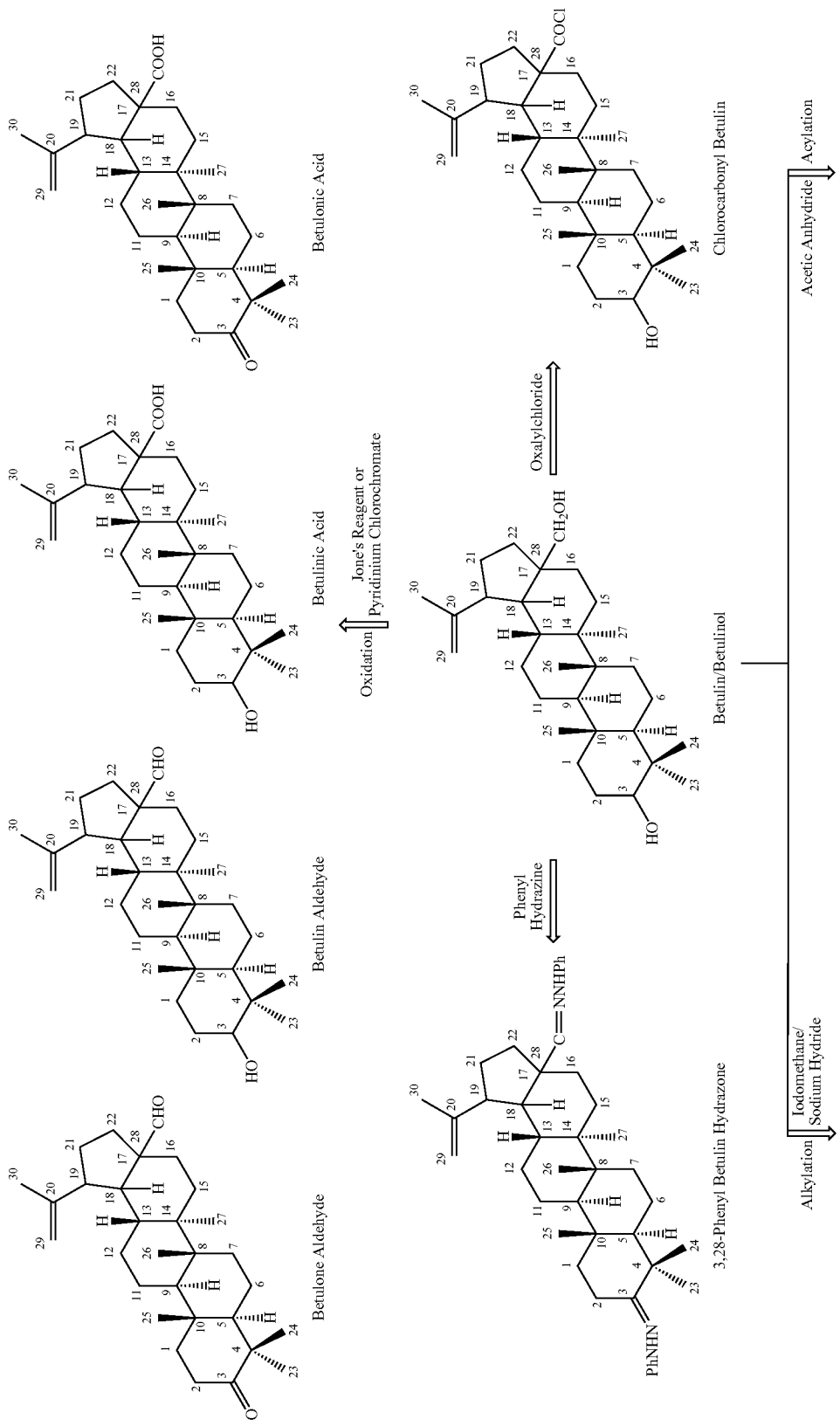

-continued
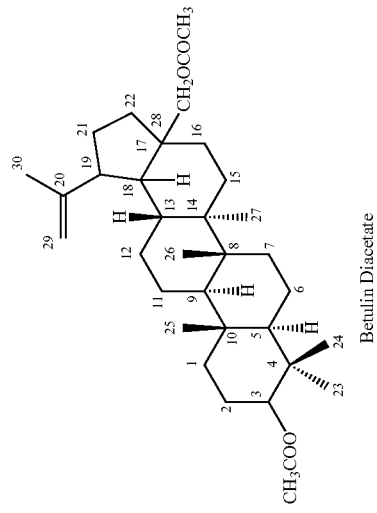
Betulin Diacetate
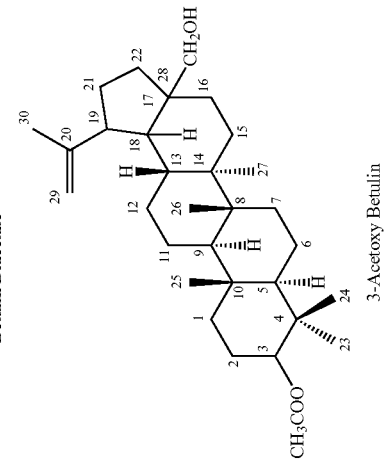
3-Acetoxy Betulin
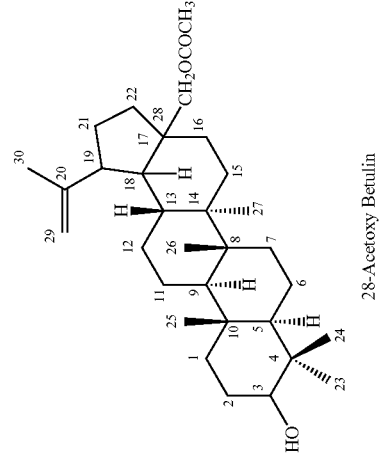
28-Acetoxy Betulin
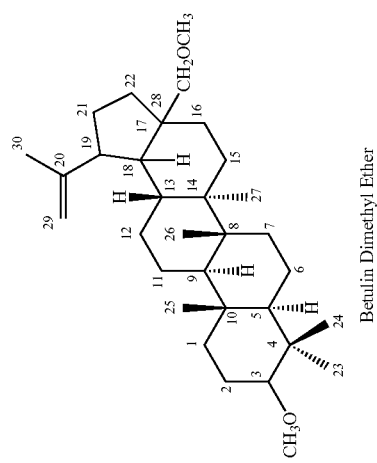
Betulin Dimethyl Ether The alkylated betulinol derivatives can be prepared in a variety of ways. Keto-derivatives can be acquired by treating betulinol with suitable oxidizing reagent, such as Jone's reagent or pyridinium chlorochromate (PCC) (Kim et al., *Synthetic Communications* 27:1607-1612 (1997); Komissarova et al., *Chemistry of National Compounds* 38:58-61 (2002); Ito et al., *J. Nat. Prod.* 64:1278-1281 (2001), which are hereby incorporated by reference in their entirety). In a preferred method, betulinol is first dissolved in acetone, and then oxidized with oxidizing reagent at 0° C. to synthesize carbonyl derivatives of betulinol, such as betulone aldehyde, betulin aldehyde, betulonic acid, and betulonic acid. Betulin acetate derivatives betulin diacetate, 3-acetoxy betulin, and 28-acetoxy betulin were prepared by acylation reaction (Kim et al., *Bioorg. Med. Chem. Lett.*, 8:1707-1712 (1998); Hiroya et al., *Bioorg. Med. Chem.* 10:3229-3236 (2002), which are hereby incorporated by reference in their entirety). In particular, a dry pyridine solution of betulinol was treated with anhydrous acetic anhydride and stirred for 6 hrs. The workup of the resulting mixture was done by diluting with ethyl acetate and washed with 10% HCl and saturated $NaHCO_3$ to yield betulin diacetate, 3-acetoxy betulin, and 28-acetoxy betulin. Betulin dimethyl ether was prepared by alkylation. To a solution of NaOH and betulinol in dry tetrahydrofuran, iodomethane was added and the resulting mixture was refluxed for 40 hrs. Distilled water was added drop wise to stop the reaction. Betulin dimethylether was obtained after column chromatography. Chlorocarbonyl betulin was obtained by treatment with oxalyl chloride (Sun et al., *J. Med. Chem.* 45:4271-4275 (2002), which is hereby incorporated by reference in its entirety). A solution of oxalyl chloride was added to betulinic acid and stirred for 2 hrs. Most of the solvent was removed under vacuo. Additional dry $CH_2Cl_2$ was added and subsequently concentrated to yield chlorocarbonyl betulin.

A summary of in vitro cytotoxicity assays of betulin derivatives to various cancer cells is presented in Table 2.

TABLE 2

In Vitro Cytotoxicity of Betulin Derivatives to various Cancer cells

| Cancer | Drug | Cell Line | Drug Concentration (M)/Percent Killed | | | | |
|---|---|---|---|---|---|---|---|
| | | | $1 \times 10^{-8}$ | $1 \times 10^{-7}$ | $1 \times 10^{-6}$ | $1 \times 10^{-5}$ | $1 \times 10^{-4}$ |
| Prostate (1) | Betulonic Acid | PC-3 | | | | 41 | 54 |
| Prostate (1) | Betulonic Acid | LNCaP | | | | 75 | 81 |
| Prostate (1) | Betulonic Acid | DU-145 | | | | 51 | 54 |
| Prostate (1) | Betulonic Acid | Fibroblasts | | | | No effect | No effect |
| Prostate (2) | Betulinol Diacetate | PC-3 | | | | 15 | 25 |
| Prostate (2) | Betulinol Diacetate | DU-145 | 27 | 100 | 100 | 100 | 100 |
| Renal (2) | Betulinol Diacetate | CAKI-1 | | | 100 | 100 | 100 |
| Renal (2) | Betulinol Diacetate | RXF 393 | 15 | 97 | 100 | 100 | 100 |
| Renal (2) | Betulinol Diacetate | TK-10 | | | | 49 | 100 | 100 |
| Breast (2) | Betulinol Diacetate | MCF7 | | 100 | 100 | 100 | 100 |
| Breast (2) | Betulone Aldehyde | MCF7 | | | | | 68 |
| Breast (2) | Betulinol Dimethyl ether | MCF7 | | | | | 97 |
| Breast (2) | Betulinol Diacetate | T-47d | | | 23 | 100 | 100 |
| Breast (1) | Betulinol Dimethyl ether | 184B5/HER | | | | | Toxic |
| Breast (1) | Betulonic Acid | 184B5/HER | | | | | Toxic |
| Ovarian (2) | Betulinol Diacetate | OVCAR-5 | | | 100 | 100 | 100 |
| Ovarian (2) | Betulinol Diacetate | OVACR-3 | | | 96 | 100 | 100 |
| CNS (2) | Betulinol Diacetate | U251 | | 100 | 100 | 100 | 100 |
| CNS (2) | Betulinol Diacetate | SF-268 | 15 | 75 | 100 | 100 | 100 |
| CNS (2) | Betulone Aldehyde | SF-268 | | | | | 27 |
| CNS (2) | Betulinol Dimethyl ether | SF-268 | | | | | 100 |
| Melanoma (2) | Betulinol Diacetate | MALME-3M | 98 | 100 | 100 | 100 | 100 |
| Lung (2) | Betulinol Diacetate | HOP-92 | | | 100 | 100 | 100 |
| Lung (2) | Betulinol Diacetate | NCI-H460 | | 25 | 100 | 100 | 100 |
| Lung (2) | Betulone Aldehyde | NCI-H460 | | | | | 89 |

TABLE 2-continued

In Vitro Cytotoxicity of Betulin Derivatives to various Cancer cells

| Cancer | Drug | Cell Line | Drug Concentration (M)/Percent Killed | | | | |
|---|---|---|---|---|---|---|---|
| | | | $1 \times 10^{-8}$ | $1 \times 10^{-7}$ | $1 \times 10^{-6}$ | $1 \times 10^{-5}$ | $1 \times 10^{-4}$ |
| Lung (2) | Betulinol Di-methyl ether | NCI-H460 | | | | | 80 |
| Lung (2) | Betulinol Diacetate | NCI-H322M | | | 100 | 100 | 100 |
| Bladder (1) | Betulonic Acid | | | | | | 37 |
| Bladder (1) | Betulone Aldehyde | | | | | | 29 |
| Bladder (1) | Betulinol Di-methyl ether | | | | | | 30 |

Example 2

Synthesis of Betulonic Acid from Betulinol

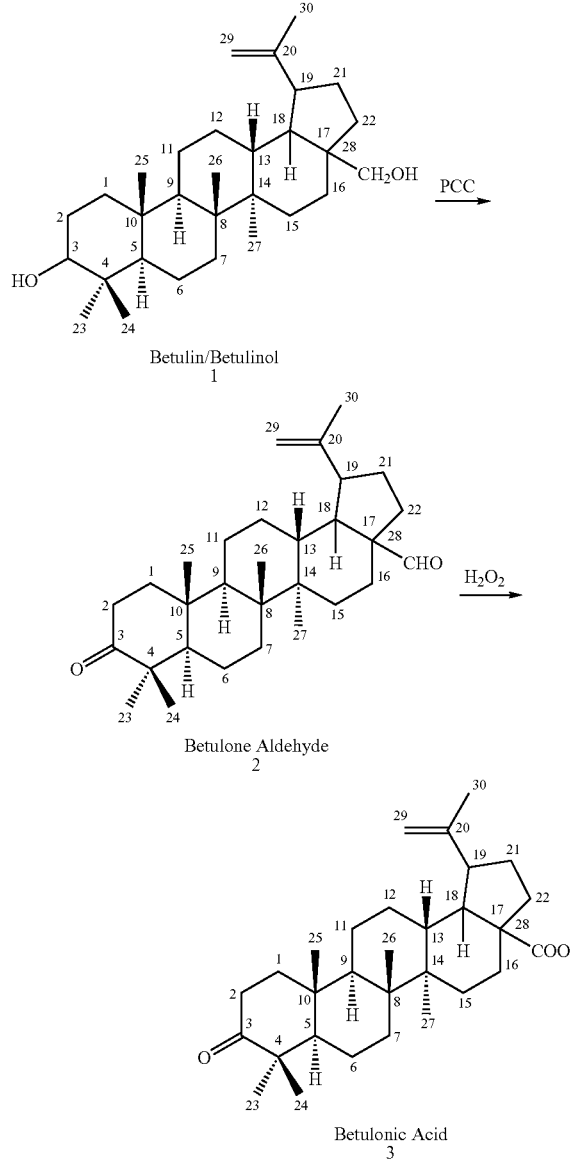

In a typical procedure, 500 mg of betulinol (1) was added to a suspension of 1.2 g of freshly activated 4 Å molecular sieves, 1.2 g of celite, 1.2 g of florisil, 500 mg of sodium acetate, and 1.2 g of pyridinium chlorochromate in 25 mL of $CH_2Cl_2$. The mixture was stirred for 2 hrs, and then filtered through a 2.5×15 cm column silica gel of 230-400 mesh and 60 Å (HF-254, E. Merck). The filtrate was evaporated in vacuum. The residue was subjected to column chromatography of silica gel to recover 370 mg of betulone aldehyde (2) as white solid. This betulone aldehyde was dissolved in 17 mL $CH_3CN$—$H_2O$ containing 877 mg of $NaH_2PO_4 \cdot H_2O$ and cooled to 0-5° C. 220 μL of 30% of aqueous $H_2O_2$ and 200 mg of $NaClO_2$ dissolved in 16 mL water were added in tandem. The mixture was brought up to room temperature and stirred for one hour. The reaction was quenched by the addition of 380 mg of $Na_2S_2O_5$. The betulonic acid was extracted with 300 mL ethyl acetate. The organic extract was washed with water and brine, and dried by 100 mg of $Na_2SO_4$. The organic solution was filtered through filter paper and the filtrate was evaporated. The residue was subjected to silica gel column chromatography to recover 347 mg of betulonic acid (3) as white solid powder. The yield and activities of betulonic acid prepared by the above method were compared with the betulonic acid prepared by the Jones reagent (Kim et al., Synthetic Communications 27:1607-1612 (1997), which is hereby incorporated by reference in its entirety).

Example 3

Results of Chemistry Characterizations: GC

The purity of betulonic acid and its derivatives was studied by taking gas chromatographic profiles. 8 μL of each sample was injected to yield the following retention time ($t_R$):

TABLE 3

Retention Times from Gas Chromatogram Profiles

| Sample | Retention Time ($t_R$) |
|---|---|
| Betulonic Acid | 11.044 |
| Monomer | 10.936 |
| Dimer | 10.793 |

Figure 1B:
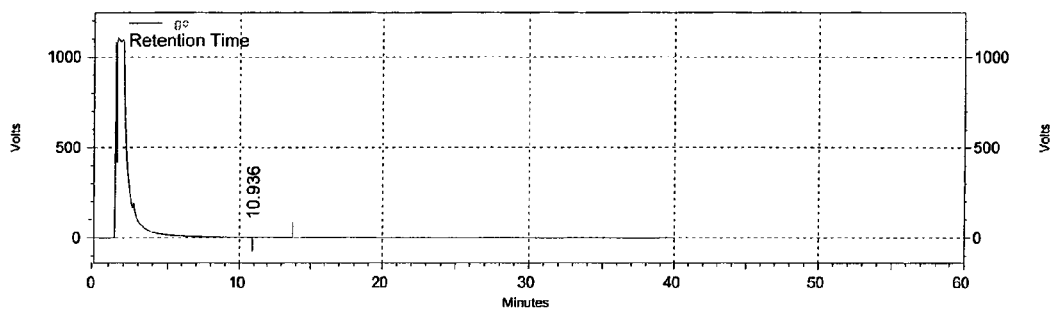
Figure 1C:
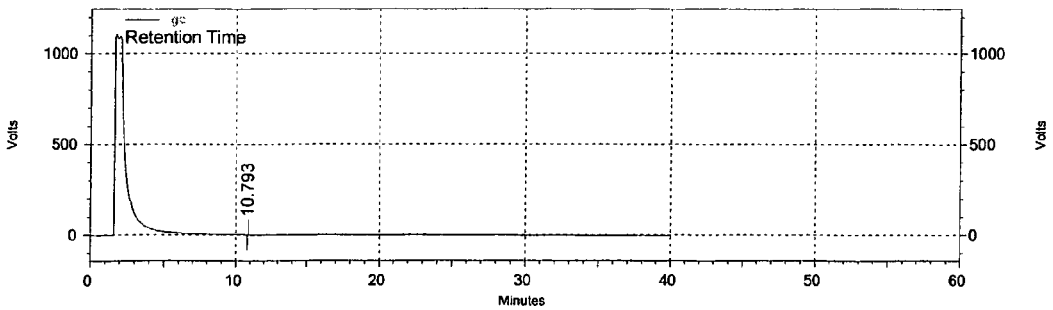

FIGS. 1A-C show a typical chromatogram of betulonic acid and its derivatives with their corresponding retention time. Close examination of these chromatograms reveals that the betulonic acid, monomer and dimer, gave neat chromatograms.

Example 4

Spectroscopic Analysis

Table 4 summarizes the NMR shifts for the synthesized betulonic acid derivatives.

TABLE 4

NMR Chemical Shifts of Betulonic Acid Derivatives

| Betulinol Derivative | $^1$H NMR (500 MHz, CDCl$_3$) | $^{13}$C NMR (500 MHz, CDCl$_3$) |
|---|---|---|
| 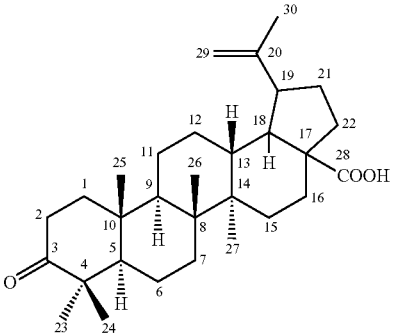 Betulonic Acid | δ 0.93, 0.97, 0.99, 1.01, 1.07 (15H, 3H each, all s, H-23-27), 1.2-1.6 (16H, m, H-1, 5-7, 9, 11, 12, 15, 16, 21, 22), 1.7 3H, s, H-30), 1.8-2.0 (3H, m, H-1, 18, 21), 2.2-2.3 (3H, m, H-2, 16, 22), 2.4-2.5 (2H, m, H-2, 13), 3.0 (1H, dt, J = 5, 11 Hz, H-19), 4.6 (1H, s, H-29), 4.7 (1H, s, H-29) | δ 14.8 (C-27), 16.0 (C-26), 16.2 (C-25), 19.6 (C-30), 19.8 (C-6), 21.2 (C-24), 21.5 (C-11), 26.8 (C-12, 23), 30.7 (C-15, 21), 32.3 (C-16), 33.7 (C-7), 34.3 (C-2), 37.1 (C-10), 37.2 (C-22), 38.7 (C-13), 37.8 (C-1, 8), 42.6 (C-14), 47.5 (C-18), 49.3 (C-4), 50.0 (C-9, 19), 55.0 (C-5), 56.6 (C-17), 110.0 (C-29), 150.5 (C-20), 183.1 (C-28), 218.6 (C-3) |
| 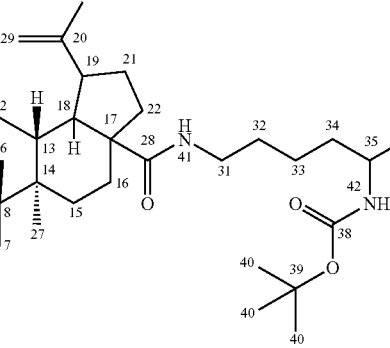 Monomer Ester | δ 0.85, 0.89, 0.94, 0.98 (15H, all s, H-23-27), 1.1-1.5 (18H, m, H-1, 5-7, 9, 11, 12, 15, 16, 18, 21, 22, 33), 1.36 (9H, brs, H-40), 1.60 (3H, s, H-30), 1.6-1.8 (4H, m, H-1, 16, 21, 22), 1.8-2.0 (4H, m, H-32, 34), 2.2-2.3 (1H, m, H-2), 2.3-2.5 (2H, m, H-2, 13), 3.0-3.1 (1H, dt, J = 4, 11 Hz, H-19), 3.10-3.15 (1H, m, H-31), 3.15-3.21 (1H, m, H-31), 3.66 (3H, s, H-37), 4.20 (1H, m, H-35), 4.51 (1H, s, H-29), 4.65 (1H, s, H-29), 5.11 (1H, d, J = 8 Hz, H-42), 5.88 (1H, t, J = 5 Hz, H-41) | δ 14.5 (C-27), 15.9 (C-26), 16.0 (C-25), 19.5, (C-30), 19.6 (C-6), 21.0 (C-24), 21.5 (C-33), 22.8 (C-11), 25.6 (C-12), 26.6 (C-23), 28.3 (C-40), 29.4 (C-15), 30.8 (C-21, 32), 32.4 (C-34), 33.6 (C-7), 33.7 (C-16), 34.1 (C-2), 36.9 (C-10), 37.7 (C-13), 38.4 (C-22), 38.8 (C-1), 39.6 (C-8), 40.7 (C-31), 42.5 (C-14), 46.6 (C-19), 47.3 (C-4), 50.0 (C-9), 50.1 (C-18), 52.2 (C-37), 53.3 (C-35), 54.9 (C-5), 55.5 (C-17), 79.8 (C-39), 109.4 (C-29), 150.9 (C-20), 155.4 (C-38), 73.2 (C-36), 176.1 (C-28), 218.2 (C-3) |
| 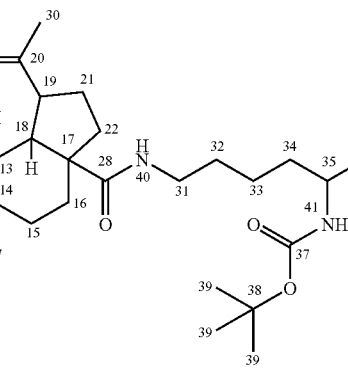 Monomer | δ 0.94, 0.99, 1.00, 1.04, 1.09 (15H, 3H each, all s, H-23-27), 1.3-1.6 (18H, m, H-1, 5-7, 9, 11, 12, 15, 16, 18, 21, 22, 33), 1.47 (9H, brs, C-39), 1.70 (3H, s, H-30), 1.70-1.75 (4H, m, H-1, 16, 21, 22), 1.90-1.98 (4H, m, H-32, 34), 2.39-2.44 (1H, m, H-2), 2.44-2.55 (2H, m, H-2, 13), 3.12 (1H, dt, J = 3.5, 10.8 Hz, H-19), 3.22-3.32 (2H, m, H-31), 4.31 (1H, m, H-35), 4.62 (1H, s, H-29), 4.76 (1H, s, H-29), 5.17 (1H, d, J = 7 Hz, H-41), 5.80 (1H, m, H-40) | δ 14.8 (C-27), 16.1 (C-26), 16.2 (C-25), 19.7 (C-30), 19.8 (C-6), 21.2 (C-24), 21.7 (C-33), 22.8 (C-11), 25.8 (C-12), 26.8 (C-23), 28.5 (C-39), 29.6 (C-15), 31.0 (C-21, 32), 32.2 (C-34), 33.9 (C-7), 34.0 (C-16), 34.4 (C-2), 37.1 (C-10), 38.0 (C-13), 38.7 (C-22), 39.1 (C-1), 39.8 (C-8), 40.9 (C-31), 42.7 (C-14), 46.9 (C-19), 47.6 (C-4), 50.2 (C-9, 18), 53.8 (C-35), 55.2 (C-5), 55.8 (C-17), 80.8 (C-38), 110.0 (C-29), 151.4 (C-20), 156.4 (C-37), 176.1 (C-28), 177.1 (C-36), 218.2 (C-3) |

TABLE 4-continued

NMR Chemical Shifts of Betulonic Acid Derivatives

| Betulinol Derivative | ¹H NMR (500 MHz, CDCl$_3$) | ¹³C NMR (500 MHz, CDCl$_3$) |
|---|---|---|
| Dimer Ester | δ 0.89, 0.91, 0.92, 0.93, 0.97, 0.98, 1.02, 1.03, 1.06, 1.08 (30H, 3H each, all s, H-23-27, 23'-27'), 1.3-1.6 (38H, m, H-1, 1', 5-7, 5'-7', 9, 9', 11, 11', 12, 12',15, 15', 16, 16', 18, 18', 21, 21', 22, 22', 33, 33'), 1.45 (9H, brs, H-40), 1.68 (6H, s, H-30, 30'), 1.70-1.75 (8H, m, H-1, 1', 16, 16', 21, 21', 22, 22'), 1.90-1.98 (8H, m, H-32, 32', 34, 34',), 2.39-2.44 (2H, m, H-2, 2'), 2.44-2.55 (4H, m, H-2, 2', 13, 13',), 3.12 (2H, dt, J = 3.5, 10.8 Hz, H-19, 19'), 3.22-3.32 (4H, m, H-31, 31'), 3.73 (3H, s, H-37), 4.31 (1H, m, H-35), 4.55 (1H, m, H-35'), 4.59 (2H, s, H-29, 29'), 4.73 (2H, s, H-29, 29'), 5.18 (1H, d, J = 7 Hz, H-42'), 5.85 (2H, t, J = 5.6 Hz, H-41, 41'), 6.82 (1H, d, J = 7.6 Hz, H-42) | δ 14.6 (C-27), 15.3 (C-27'), 16.1 (C-26, 26'), 16.4 (C-25, 25'), 19.6 (C-30, 30'), 19.7 (C-6, 6'), 21.1 (C-24), 21.1 (C-24'), 21.2 (C-33'), 21.5 (C-33), 22.7 (C-11, 11'), 25.7 (C-12), 25.8, (C-12'), 26.7 (C-23), 26.8 (C-23'), 28.4 (C-40), 29.4 (C-15), 29.5 (C-15'), 30.1 (C-21', 30'), 31.0 (C-21, 30), 32.2 (C-34'), 32.5 (C-34), 33.7 (C-7), 33.8 (C-7'), 34.0 (C-16), 34.1 (C-16'), 34.2 (C-2), 34.3 (C-2'), 36.6 (C-10)'), 37.0 (C-10), 37.0 (C-13'), 37.8 (C-13), 38.5 (C-22, 22'), 38.7 (C-1, 1'), 39.7 (C-8), 39.9 (C-8'), 40.6 (C-31), 40.8 (C-31'), 42.6 (C-14, 14'), 46.7 (C-19), 46.9 (C-19'), 47.4 (C-4), 47.4 (C-4'), 50.1 (C-9), 50.2 (C-9'), 50.6 (C-18, 18'), 52.4 (C-37), 54.2 (C-35, 35'), 55.0 (C-5), 55.1 (C-5'), 55.6 (C-17, 17'), 80.0 (C-39), 109.4 (C-29, 29'), 151.1 (C-20, 20'), 155.7 (C-38), 171.9 (C-36'), 172.9 (C-36), 176.2 (C-28, 28'), 218.2 (C-3), 218.4 (C-3') |
| Dimer | δ 0.88, 0.91, 0.95, 0.98, 1.01, 1.02, 1.05, 1.06 (30H, all s, H-23-27, 23'-27'), 1.2-1.1.53 (38H, m, H-1, 1', 5-7, 5' 7', 9, 9', 11, 11', 12, 12', 15, 15', 16, 16', 18, 18', 21, 21', 22, 22', 33, 33',), 1.41 (9H, brs, H-39), 1.66 (6H, s, H-30, 30'), 1.70-1.75 (8H, m, H-1, 1', 16, 16', 21, 21', 22, 22'), 1.90-1.98 (8H, m, H-32, 32', 34, 34',), 2.39-2.55 (6H, m, H-2, 2', 13, 13'), 3.10-3.43 (6H, m, H-19, 19', 31, 31'), 4.13 (1H, m, H-35'), 4.31 (1H, m, H-35), 4.57 (2H, s, H-29, 29'), 4.71 (2H, s, H-29, 29'), 5.18 (1H, d, J = 7 Hz, H-41'), 5.85 (2H, t, J = 5.6 Hz, H-40, 40'), 6.82 (1H, d, J = 7.6 Hz, H-41) | δ 14.7 (C-27), 15.4 (C-27'), 16.1 (C-26, 26'), 16.5 (C-25, 25'), 19.6 (C-30, 30'), 19.8 (C-6, 6'), 21.1 (C-24), 21.6 (C-24'), 21.5 (C-33'), 21.6 (C-33), 22.9 (C-11, 11'), 25.8 (C-12, 12'), 26.8 (C-23), 26.9 (C-23'), 28.6 (C-39), 28.9, (C-15), 29.5 (C-15'), 31.1 (C-21, 21', 30, 30'), 32.4 (C-34, 34'), 33.6 (C-7), 33.8 (C-7'), 34.0 (C-16), 34.1 (C-16'), 34.3 (C-2, 2'), 36.0 (C-10'), 37.0 (C-10), 37.1 (C-13'), 37.7 (C-13), 38.6 (C-22, 22'), 39.1 (C-1, 1'), 39.8 (C-8), 39.9 (C-8'), 40.6 (C-31), 40.8 (C-31'), 42.6 (C-14, 14'), 46.7 (C-19), 47.1 (C-19'), 47.4 (C-4), 47.4 (C-4'), 50.1 (C-9), 50.2 (C-9'), 50.5 (C-18, 18'), 54.9 (C-35, 35'), 55.0 (C-5), 55.1 (C-5'), 55.6 (C-17, 17'), 79.7 (C-38), 109.5 (C-29, 29'), 151.2 (C-20, 20'), 155.9 (C-37), 176.4 (C-28, 28', 36, 36'), 218.1 (C-3), 218.4 (C-3') |

Betulonic acid and its derivatives were subsequently subjected to spectroscopic analysis in order to resolve their molecular structure. The Electrospray mass spectrometric analysis confirmed their pentacyclic styrene nature of these compounds. The samples were mass analyzed on a Micromass Quattro II triple quadrupole instrument with electrospray (ES) ionization in the positive mode. Samples were introduced by continuous infusion at a rate of 5 μL/min as a nominal 200 μM concentration solution in a 75:25:2 (v/v) acetonitrile-water-acetic acid. When necessary, product ion spectra were obtained by maintaining argon gas in the collision chamber of the instrument at a pressure of $4\times10^{-3}$ mbar.

Figure 2A:
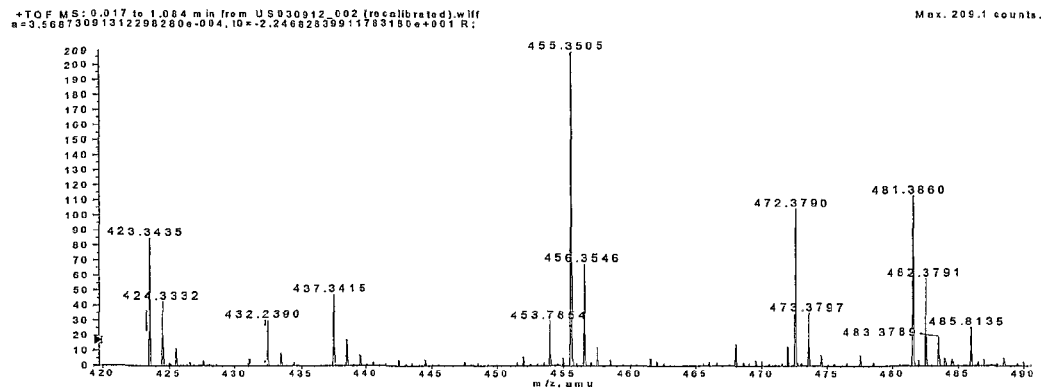
FIG. 2A is a chromatogram that included parts of MS spectra of betulonic acid after internal calibration, and included calibrant signals: m/z 365.3016, 423.3434, 481.3853, 539.4272, and 597.4690 are the calculated masses for polypropylene glycol) bis(2-aminopropyl ether). In the spectra, [M+H]$^+$ and [M+NH$_4$]$^+$ ions (m/z 455 and 472 for betulonic acid) are found, and losses also seen in the MS spectra, deriving from in-source fragmentation (m/z 437 for betulonic acid).
Figure 2B:
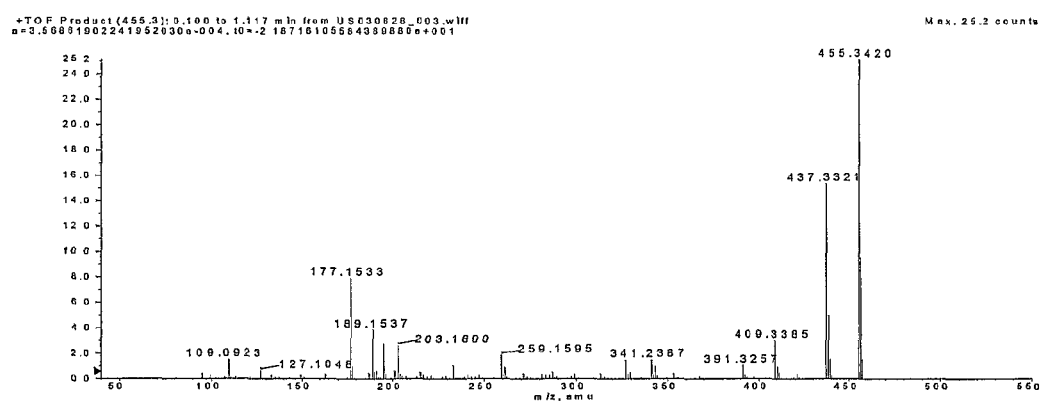
FIG. 2B shows the MS spectra of m/z 544, 471, and 455 for betulonic acid.

FIG. 2A included parts of MS spectra of betulonic acid after internal calibration, and included calibrant signals: m/z 365.3016, 423.3434, 481.3853, 539.4272, and 597.4690 are the calculated masses for poly(propylene glycol) bis(2-aminopropyl ether). In the spectra, $[M+H]^+$ and $[M+NH_4]^+$ ions (m/z 455 and 472 for betulonic acid) are found, and losses also seen in the MSMS spectra, deriving from in-source fragmentation (m/z 437 for betulonic acid). FIG. 2B shows the MSMS spectra of m/z 544, 471, and 455 for betulonic acid.

Figure 3A:
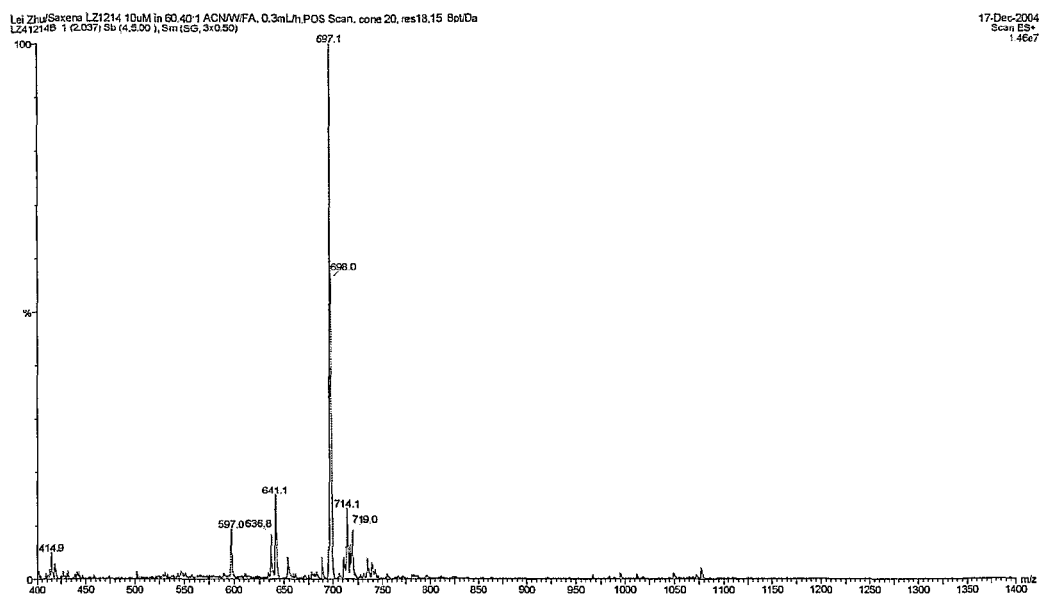
FIG. 3A-C are MS spectra of monomer ester showing that it is essentially a single compound, appearing as the m/z 697 singly protonated ion (FIG. 3A). From a higher resolution, more slowly recorded ESI-MS scan (FIG. 3B), the monoisotopic molecular mass of the neutral compound is computed as 696.5±0.2 Da. The singly protonated positive ion of this compound is rather labile. As shown in the product ion spectrum of FIG. 3C, the collision induced decomposition (CID) of the m/z 697 ion has two efficient pathways, one involving the loss of a 56 Da neutral, the other the loss of a 100 Da neutral. The fragmentation requires relatively low collision energy (10 volts). As a consequence, the m/z 641 and 597 ions also show up in the ordinary mass spectrum of FIG. 3A under source conditions where average stability molecules would not fragment.
Figure 3B:
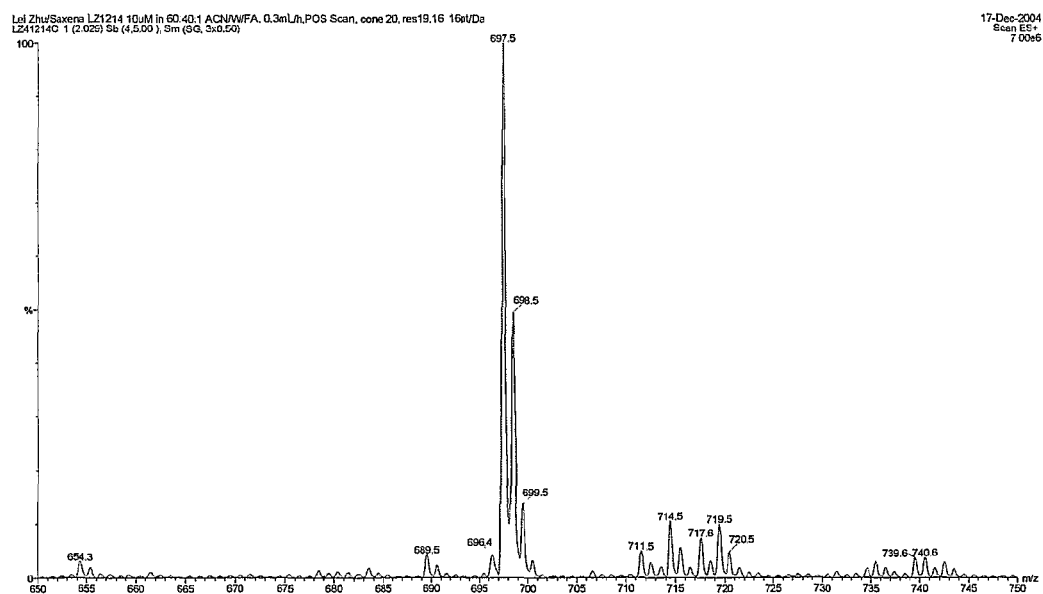
Figure 3C:
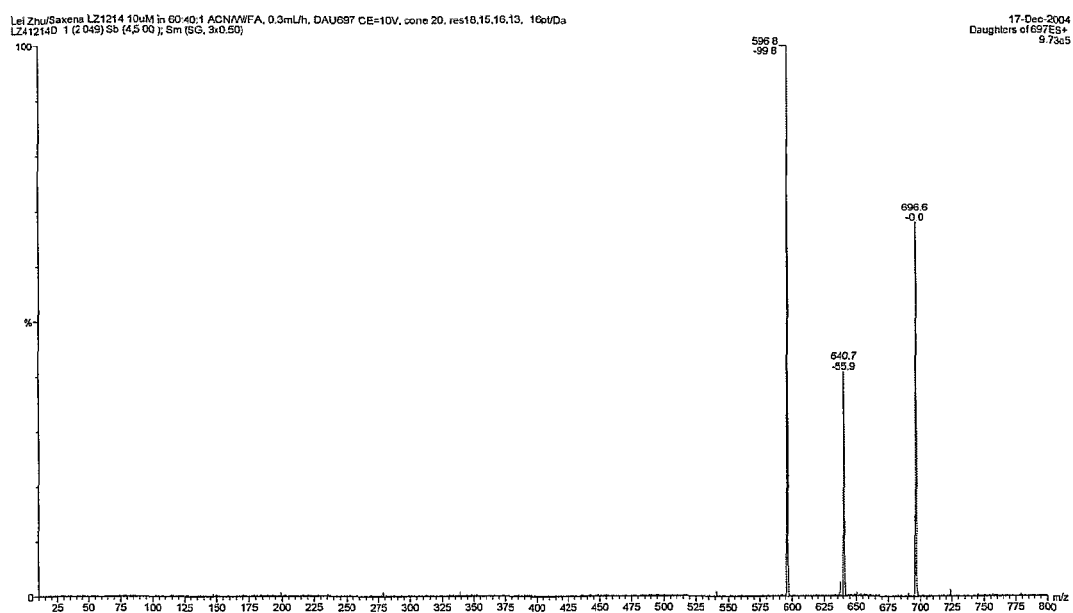

The MS spectra of monomer ester (FIGS. 3A-C show that it is essentially a single compound, appearing as the m/z 697 singly protonated ion (FIG. 3A). From a higher resolution, more slowly recorded ESI-MS scan (FIG. 3B) the monoisotopic molecular mass of the neutral compound is computed as 696.5±0.2 Da. The singly protonated positive ion of this compound is rather labile. As shown in the product ion spectrum (FIG. 3C), the collision induced decomposition (CID) of the m/z 697 ion has two efficient pathways, one involving the loss of a 56 Da neutral, the other the loss of a 100 Da neutral. The fragmentation requires relatively low collision energy, 10 volts. As a consequence, the m/z 641 and 597 ions also show up in the ordinary mass spectrum of FIG. 3A under source conditions where average stability molecules would not fragment.

Figure 4A:
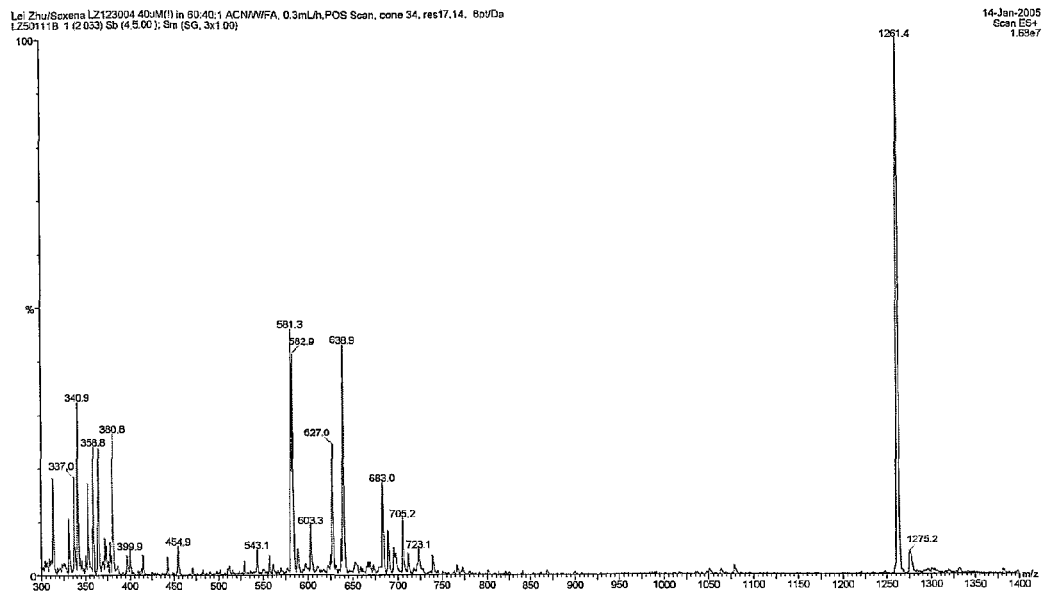
FIGS. 4A-B show the MS spectra of dimer ester.
Figure 4B:
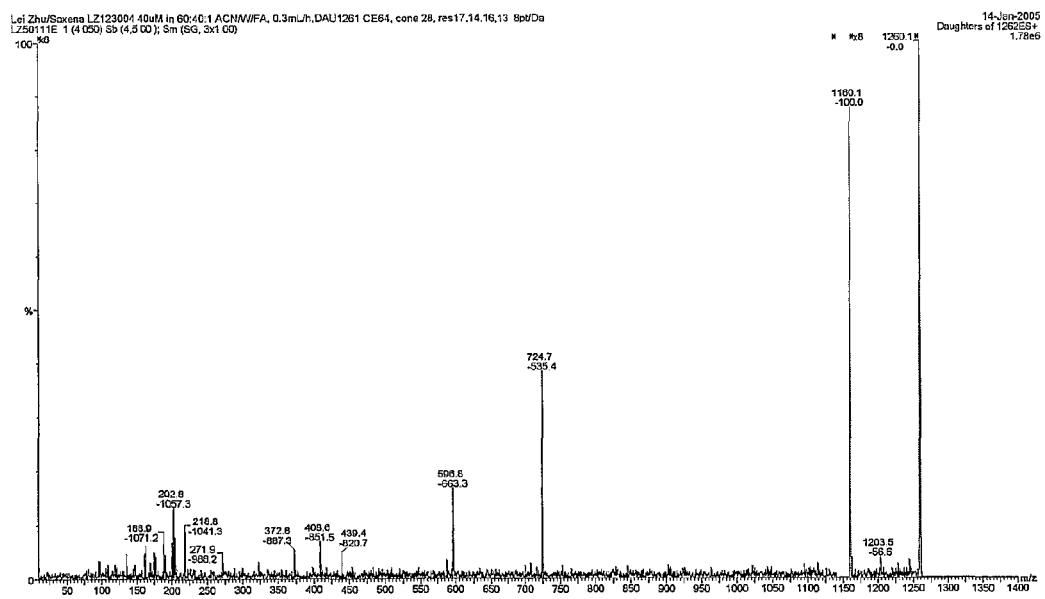

The MS spectra of dimer ester is shown in FIGS. 4A-B. As shown in FIG. 4A, the most intense peak in the ESI mass spectrum is the singly protonated ion at m/z 1261. The low level impurities with ion at m/z 581, 627, 639, and 683 are present. Since the sensitivity for the structure is low, 40 μM concentration solution was used to observe a strong m/z 1261 peak. As shown in FIG. 4B, the predominant fragmentation process, as it was in monomer ester, is the loss of a 100 Da neutral, presumably in the form of isobutylene+$CO_2$. Among the additional, very weak, product ions those at m/z 1204 and 734 are significant, because they can be interpreted as a loss of $C_4H_8$ and a loss of a betulonic acid residue, respectively.

Example 5

Synthesis of Monolysinated Betulonic Acid $N_\alpha$-butyloxycarbonyl-$N_\epsilon$-benzyloxycarbonyl-Lysine (Boc-Lys (Cbz)-OH), having the formula (4)

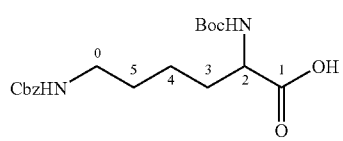

4 was obtained from Sigma-Aldrich. Both amines on C-2 and C-6 were protected by butyloxycarbonyl (Boc) and carbobenzoxy (Cbz), respectively.

$N_\alpha$-butyloxycarbonyl-$N_\epsilon$-benzyloxycarbonyl-Lysine methylester (Boc-Lys (Cbz)-OMe) was prepared as described in Kobayashi et al., *J. Org. Chem.* 66:6626-6633 (2001), which is hereby incorporated by reference in its entirety). To a 7.5 mL of trimethylsilyldiazomethane containing 1.0 g of Boc-Lys(Cbz)-OH (4) was added 5 mL anhydrous methanol while stirring at room temperature. The mixture was stirred at room temperature for 20 min, and concentrated in vacuo. The residue was subjected to a silica gel column chromatography to yield 1.0 g of Boc-Lys(Cbz)-OMe of formula (5):

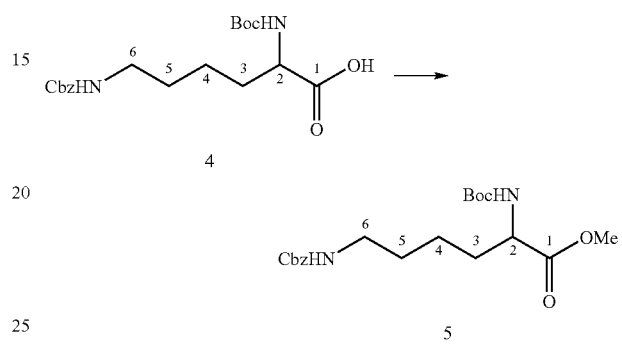

1.0 g of Boc-Lys(Cbz)-OMe (5) was dissolved in 40 mL MeOH:Ethyl acetate. 100 mg of Palladium on active carbon (Pd/C) was added to the solution. The solution was stirred under hydrogen for 2 hrs. The organic solution was filtered through Celite and washed with 10 mL MeOH. The filtrate was evaporated under reduced pressure to yield Boc-Lys-OMe of formula (6)

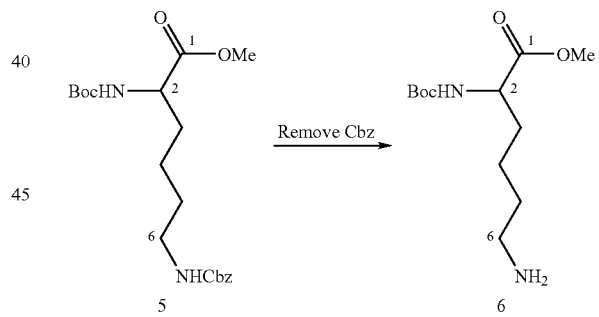

as a white solid, which was used directly for conjugation with betulonic acid (3).

Conjugation of betulonic acid to Boc-Lys-OMe monomer was carried out as described in Zhao et al., *J. Org. Chem.* 69:270-279 (2004), which is hereby incorporated by reference in its entirety. To a 30 mL solution of Boc-Lys-OMe (6) in anhydrous tetrahydrofuran ("THF") in an ice bath while stirring, 940 mg of betulonic acid (3), 350 mg of 1-Hydroxybenzotriazole Hydrate ("HOBt"), 530 mg of 1,3-dicyclohexylcarbodiimide ("DCC"), and 435 μL triethylamine were added. The mixture was stirred at 0° C. for 2 hrs and then at room temperature for 48 hrs. The resulting suspension was filtered through filter paper and the filtrate was concentrated in vacuo. The residue was subjected to silica gel column chromatography to obtain 1.3 g of monomer of formula (7)

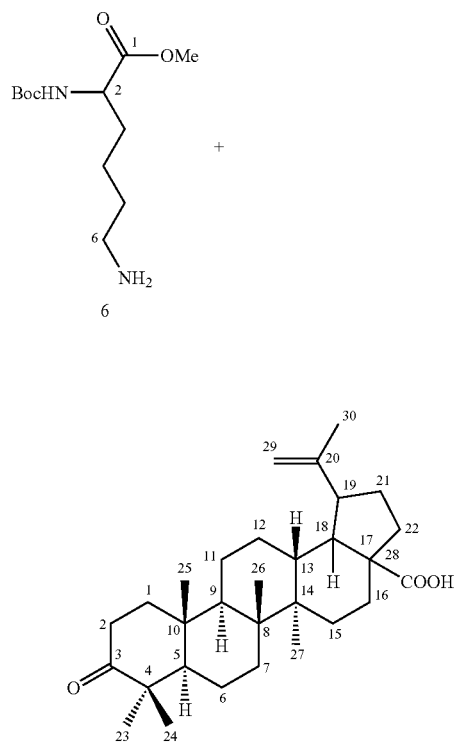

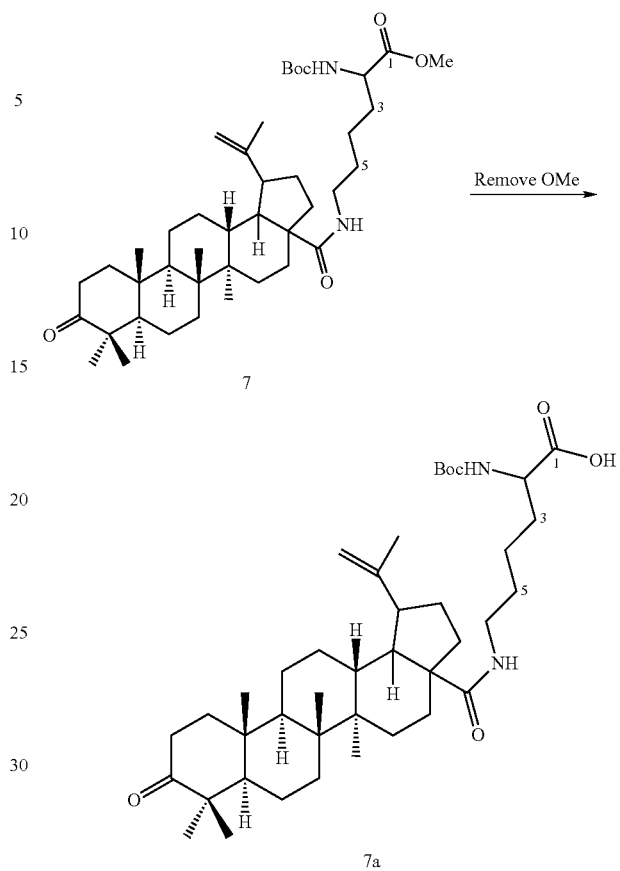

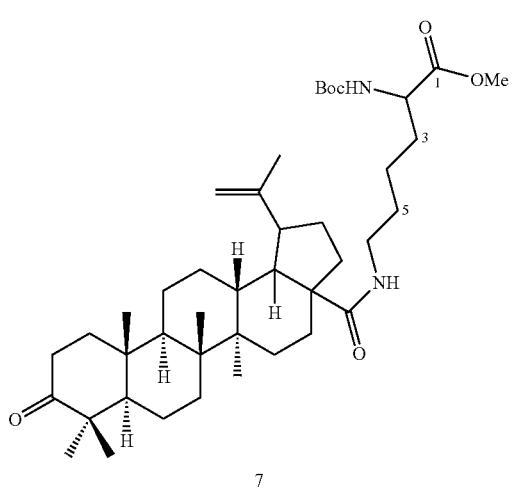

as a white solid.

Example 6

Conjugation of Two Monolysinated Betulonic Acid 150 mg of monomer (7) and 10.9 mg lithium hydroxide monohydrate (LiOH.H$_2$O) was dissolved in 3 μL THF and 100 μL H$_2$O. The resulting solution was stirred at room temperature until (7) was completely used up as monitored by thin layer chromatography ("TLC"). The solution was concentrated in vacuo. The resulting solid was subjected to silica gel column chromatography to obtain 142.6 mg of Monomer-Boc of formula (7a)

as white solid.

Monomer-OMe (N$_\epsilon$-betuloniccarbonyl-Lysine Methyl Ester) was prepared as described in Chun et al., *J. Org. Chem.* 69:7344-7347 (2004), which is hereby incorporated by reference in its entirety. Specifically, 20 mg of monomer (7) was dissolved in anhydrous 1 mL CH$_2$Cl$_2$ at 0° C. A solution of 11 μL trifluoroacetic acid (TFA) in 11 μL CH$_2$Cl$_2$ was added drop wise. The reaction mixture was stirred at room temperature for 12 h. The solvent was evaporated under vacuum. The residue was triturated with petroleum ether. The organic solvent was evaporated under vacuum to obtain crude Monomer-OMe of formula (7b)

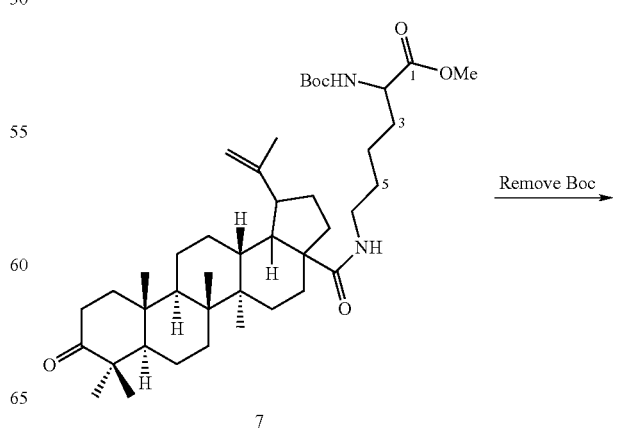

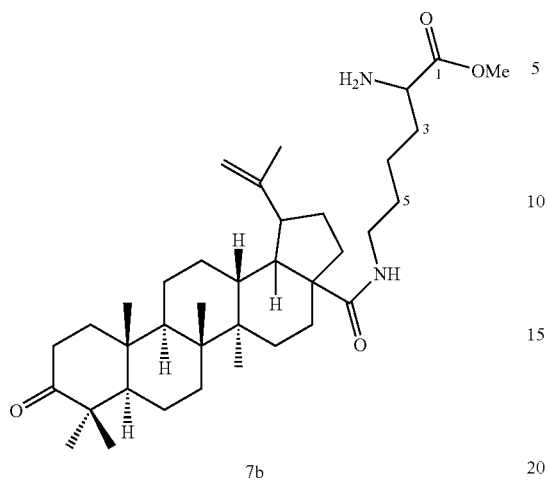

7b

To a solution of 19 mg of Monomer-Boc (7a) and 4.1 mg of HOBt in 0.5 mL dried dimethylformamide (DMF), 6 mg of DCC was added at 0° C. After the mixture was stirred for 30 min, a solution of 11.6 μL triethylamine and (7b) in 0.5 mL dried DMF was added drop wise. Stirring was continued at 0° C. for 4 h and then at room temperature for 3 days. The solvent was evaporated under reduced pressure and the resulting residue was silica gel column chromatographed to obtain 28.3 mg of dimer of formula (8)

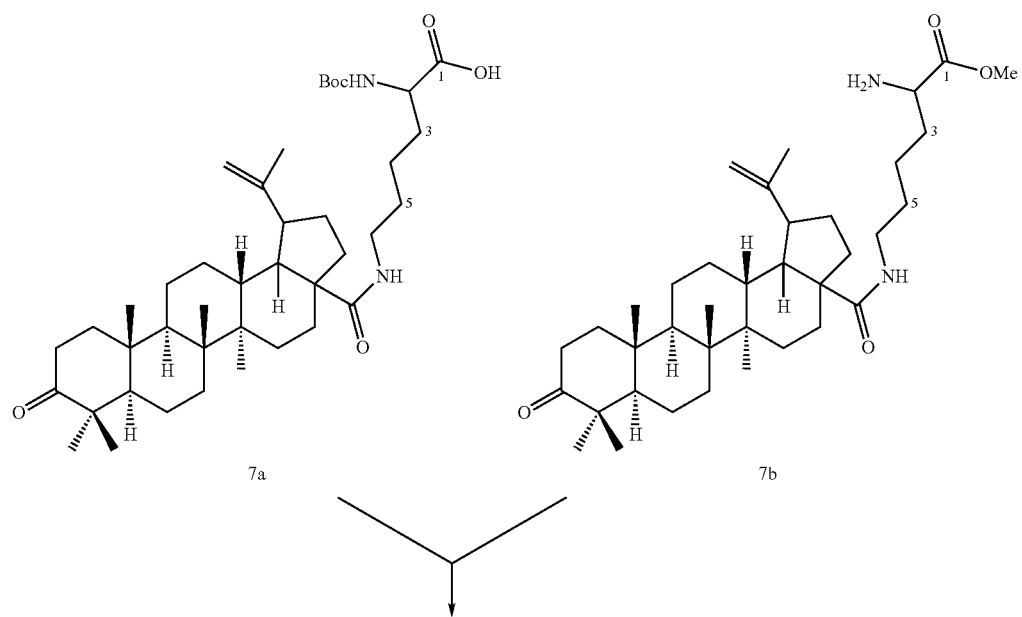

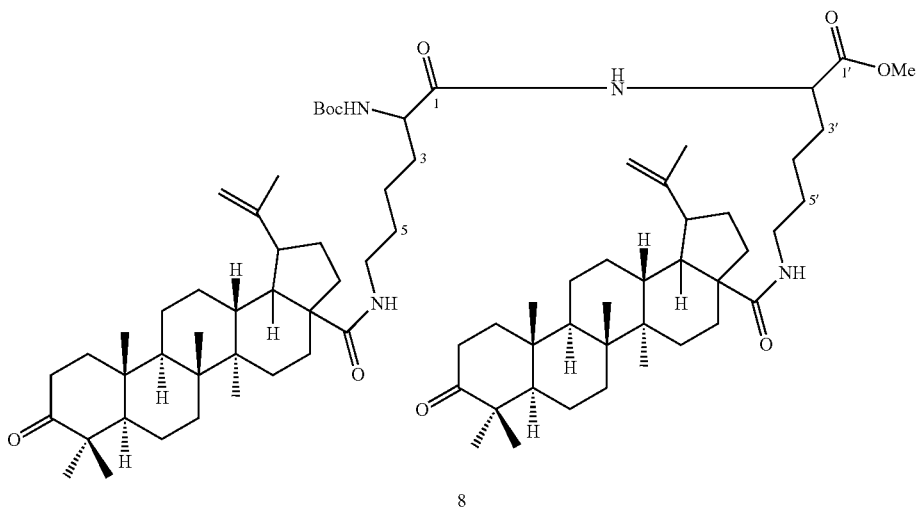

8 as a white solid.

Example 7

Conjugation of Two Dimers 150 mg of dimer (8) and 10.9 mg of LiOH.H$_2$O were dissolved in 3 mL THF and 100 μL H$_2$O. The resulting solution was stirred at room temperature until (8) was completely used up as monitored by TLC. The solution was concentrated in vacuo. The resulting solid was subjected to silica gel column chromatography to obtain 142.6 mg of Dimer-Boc of formula (8a)

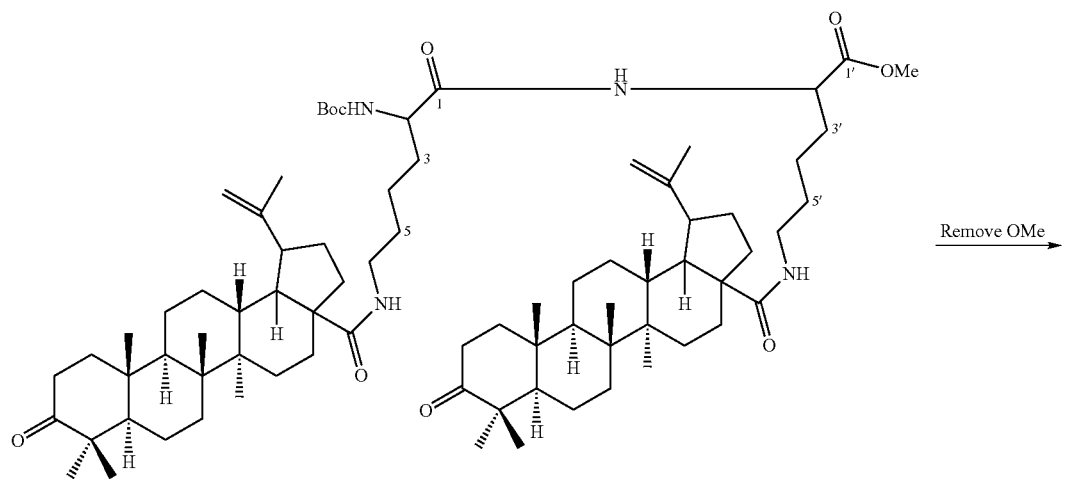

8

Remove OMe →

-continued

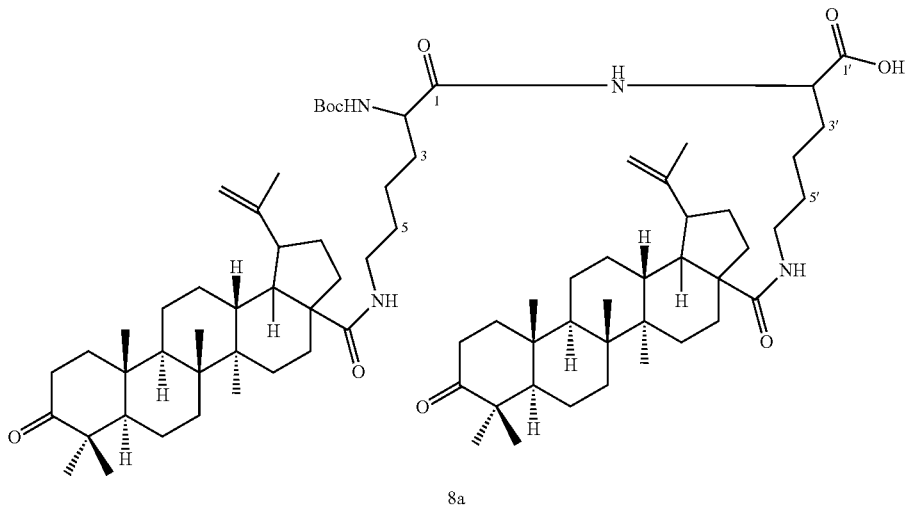

8a as white solid.

100 mg of dimer (8) was dissolved in anhydrous 1 mL CH$_2$Cl$_2$ at 0° C. A solution of 31 μL TFA in 31 μL CH$_2$Cl$_2$ was added drop wise. The reaction mixture was stirred at room temperature for 12 hrs. The solvent was evaporated under vacuum. The residue was triturated with petroleum ether. The organic solvent was evaporated under vacuum to obtain crude Dimer-OMe of formula (8b)

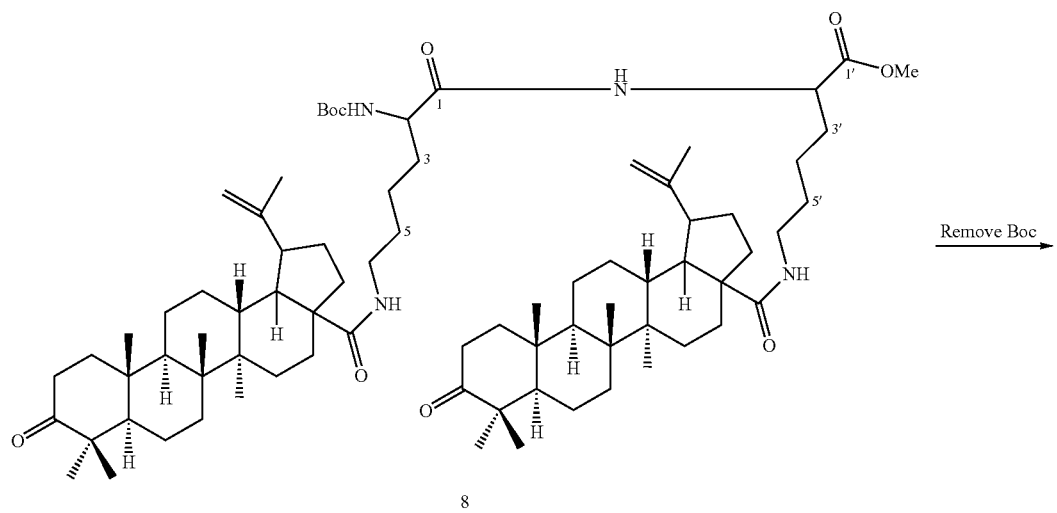

Remove Boc

8

-continued

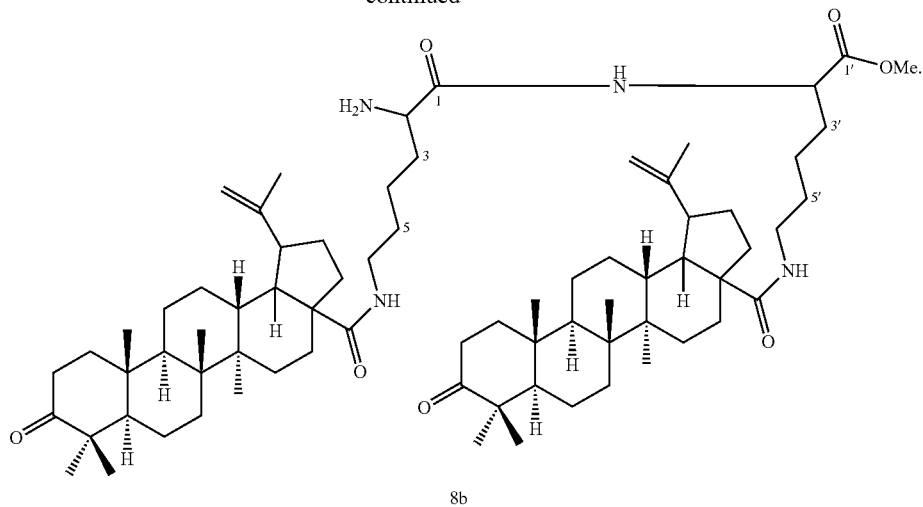

8b

To a solution of 100 mg of Dimer-Boc (8a) and 12 mg HOBt in 2 mL dried DMF, 18 mg of DCC was added at 0° C. After the mixture was stirred for 30 min, a solution of 22 μL triethylamine and (8b) in 1.7 mL dried DMF was added drop wise. Stirring was continued at 0° C. for 4 hrs and then at room temperature for 5 d. The solvent was evaporated under reduced pressure and the resulting residue was silica gel column chromatographed to obtain 20.8 mg of tetramer of formula (9)

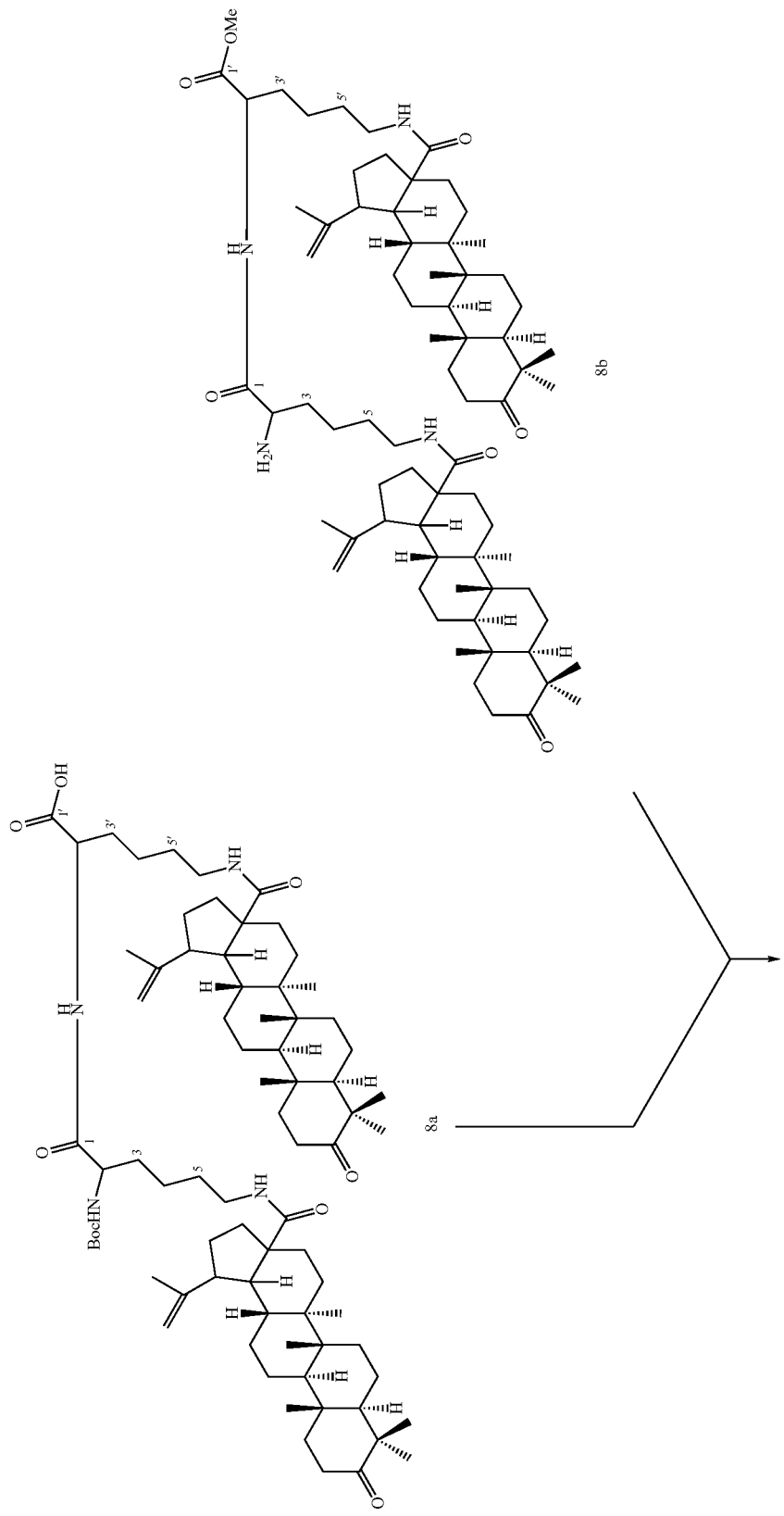

-continued
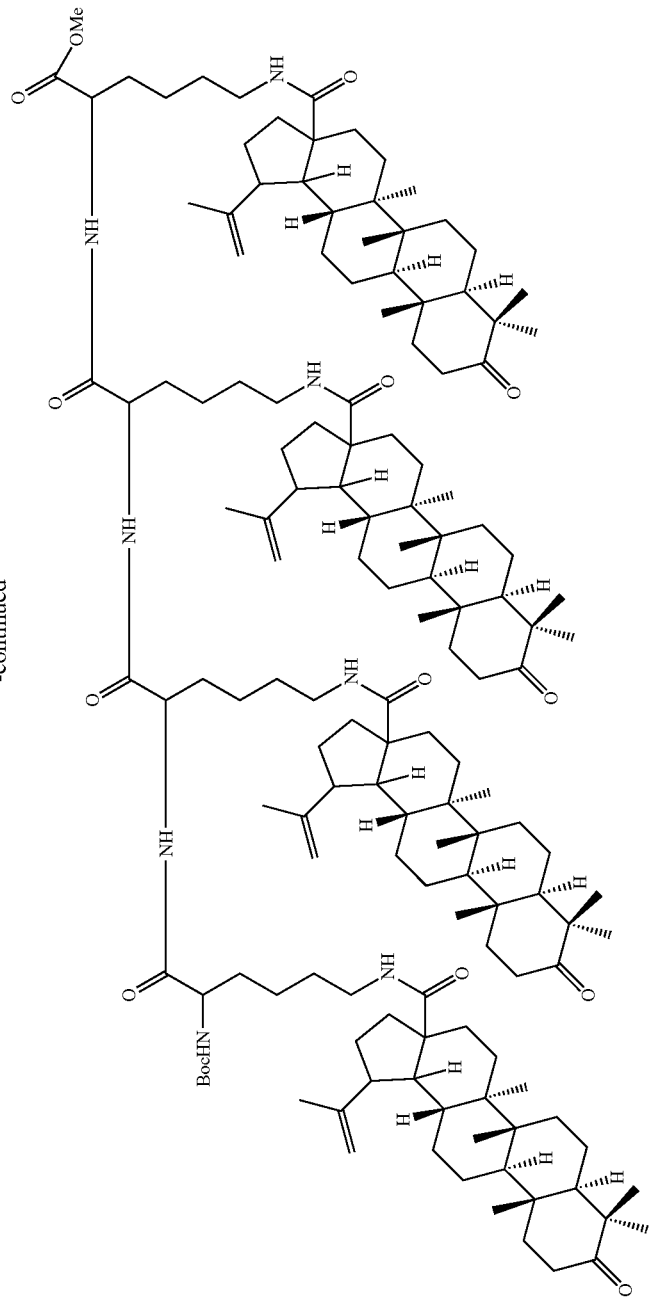
9 as a white solid.
8.3 mg of tetramer (9) and 1 mg of LiOH·H₂O was dissolved in 300 μL MeOH and 50 μL H₂O. The resulting solution was stirred at room temperature until (9) was completely used up as monitored by TLC. The solution was concentrated in vacuo. The resulting solid was subjected to silica gel column chromatography to obtain 3 mg of Tetramer-Boc (10)
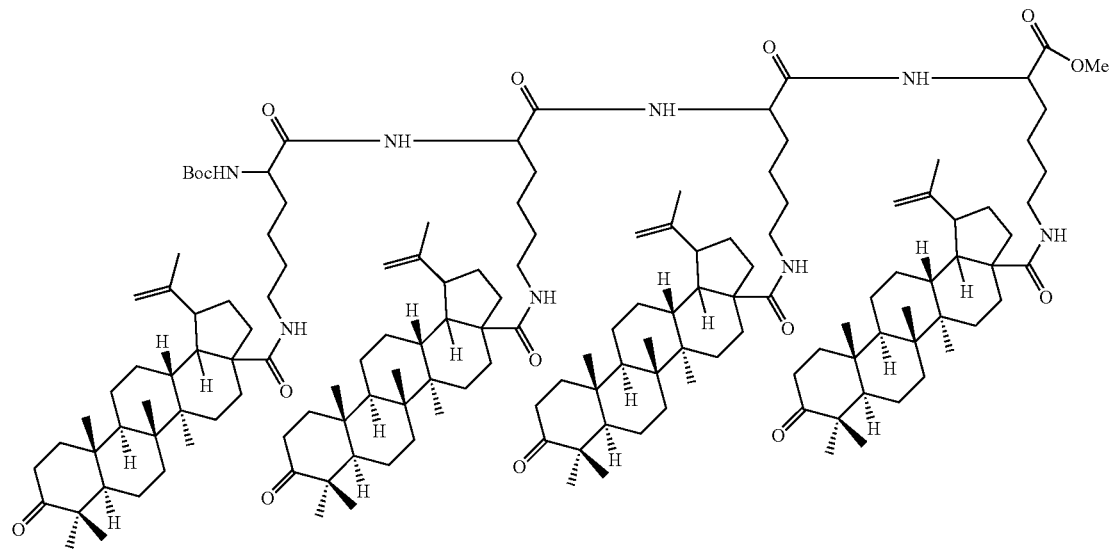
9
Remove OMe
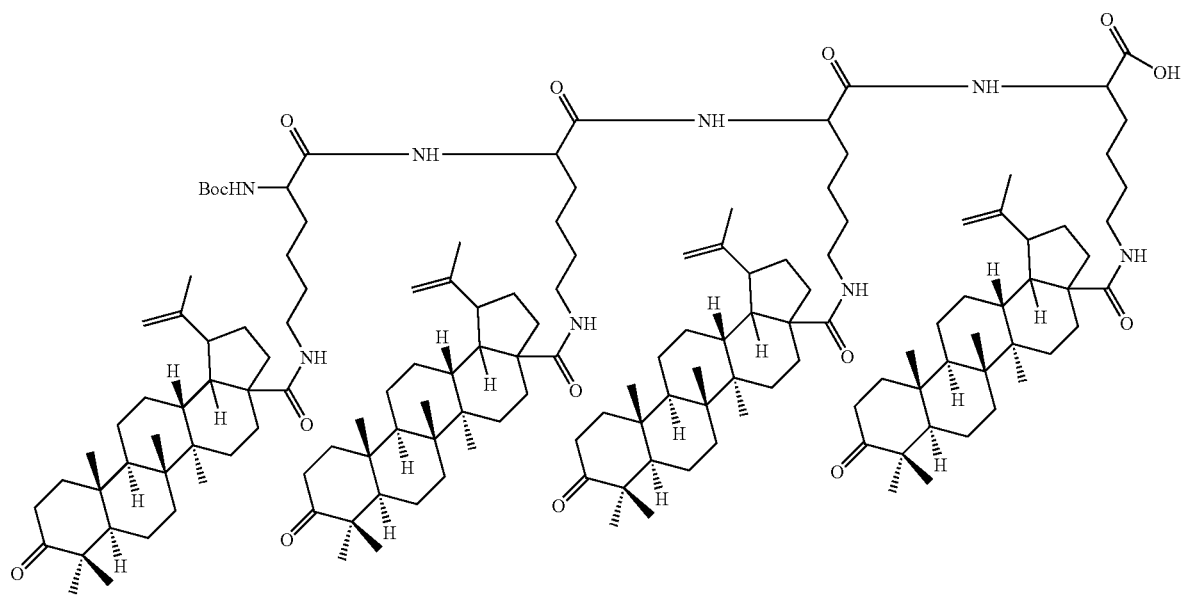
10 as white solid with 3.4 mg of unreacted tetramer (9). Tetramer (9), abbreviated as
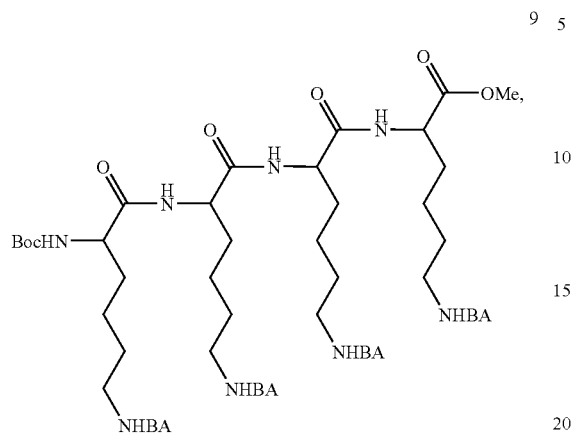
can be used for synthesis of pentamer-BA of formula (15)
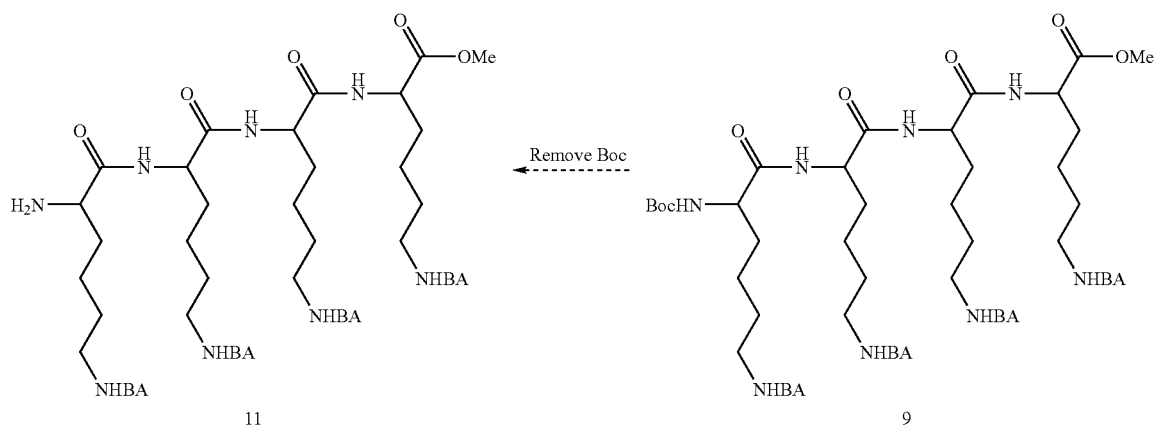
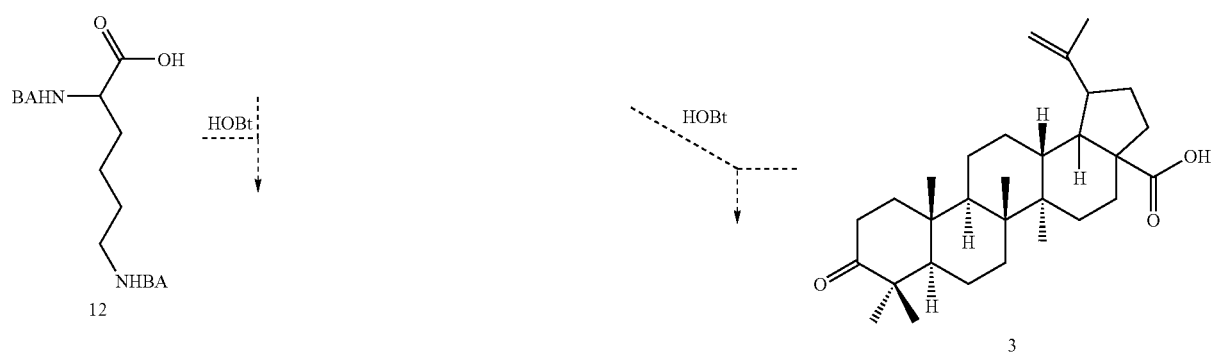

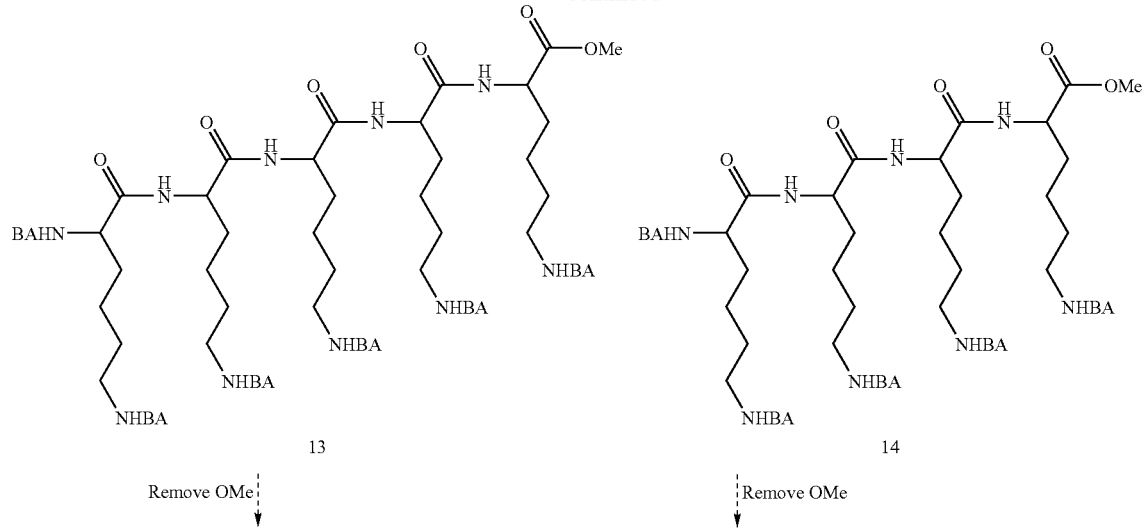

13

Remove OMe ↓

14

Remove OMe ↓

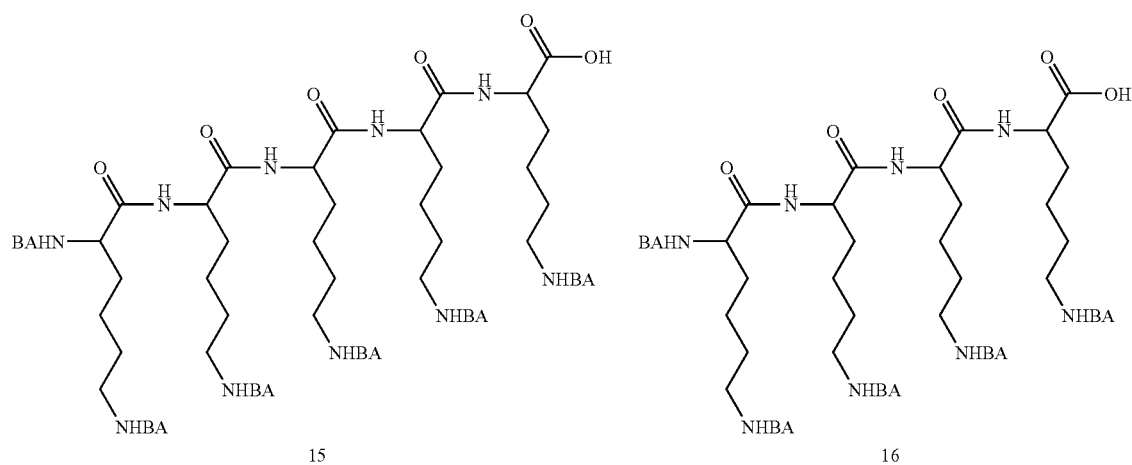

15

16 which contains six molecules of betulonic acid (3). In particular, selective deprotection can be carried out on tetramer (9) to remove Boc group and generate tetramer-OMe of formula (II). Conjugation of (11) with monomer derivative of formula (12) could yield pentamer-OMe of formula (13). Hydrolysis on (13) to selective remove methyl ester could form pentamer (15):

In addition, tetramer-OMe (11) could connect to betulonic acid (3) directly instead of the monomer derivative (12). This will yield tetramer-BA of formula (16), which contains five molecules of betulonic acid (3). Conjugation of (1) with betulonic acid (3) yields tetramer-BA-OMe of formula (14). The same hydrolysis on (14) to remove methyl ester generates tetramer-BA of formula (16).

Example 8

Preparation of Pentamer with Six Molecules of Betulonic Acid

A simple and direct way to prepare pentamer is to conjugate pentalysine with betulonic acid. However, pentalysine itself, without any protecting groups, is unstable, because it is easily polymerized and cyclized. The C-1a carboxyl group of pentalysine can be easily coupled with α-amine on C-2e or primary amines on C-6(a-e) of another molecule to form a polymer. This polymer is composed of different numbers of amino acid groups, yielding different lengths of peptide. In addition, the coupling reaction can happen in the same molecule, which connects the amino and carboxy ends of the pentalysine and cyclizes, which is illustrated as follows:

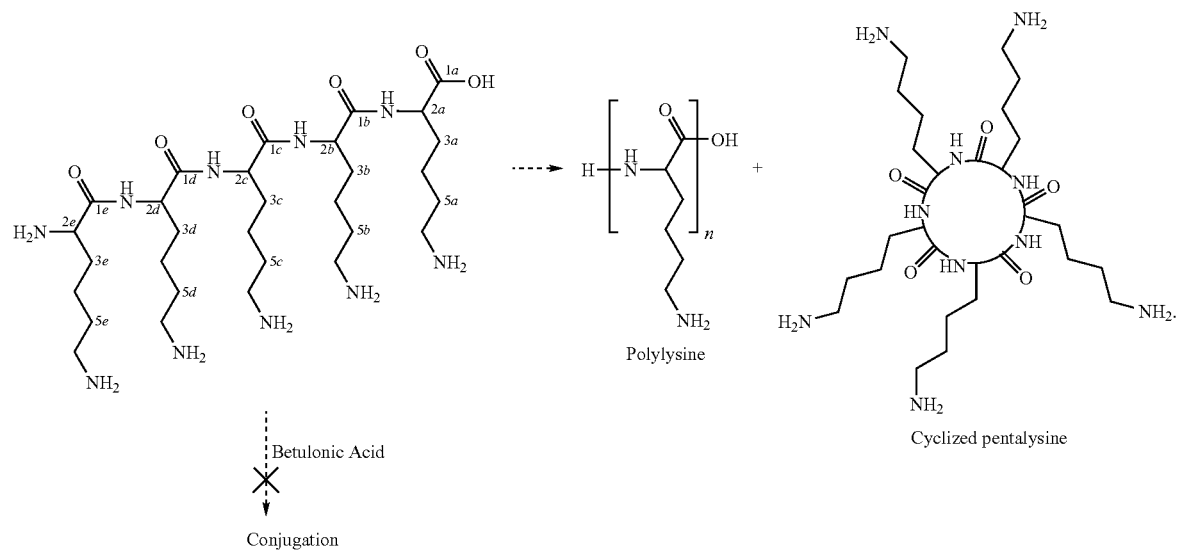
Polylysine
Cyclized pentalysine
Betulonic Acid
Conjugation
A pentalysine derivative is needed to conjugate with betulonic acid. Further, pentalysine methyl ester of formula (17)
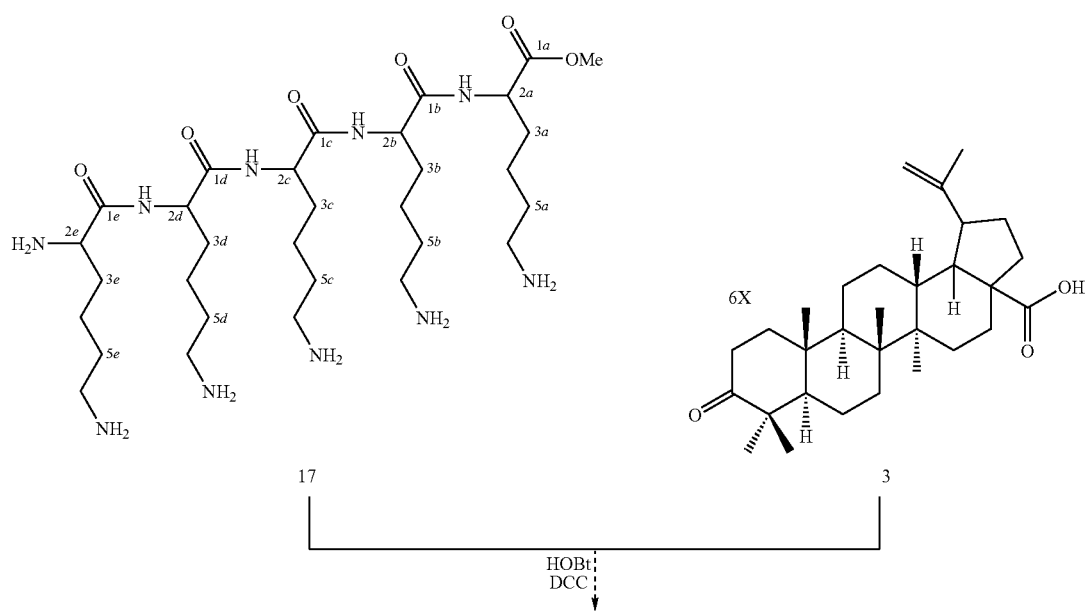
HOBt
DCC -continued

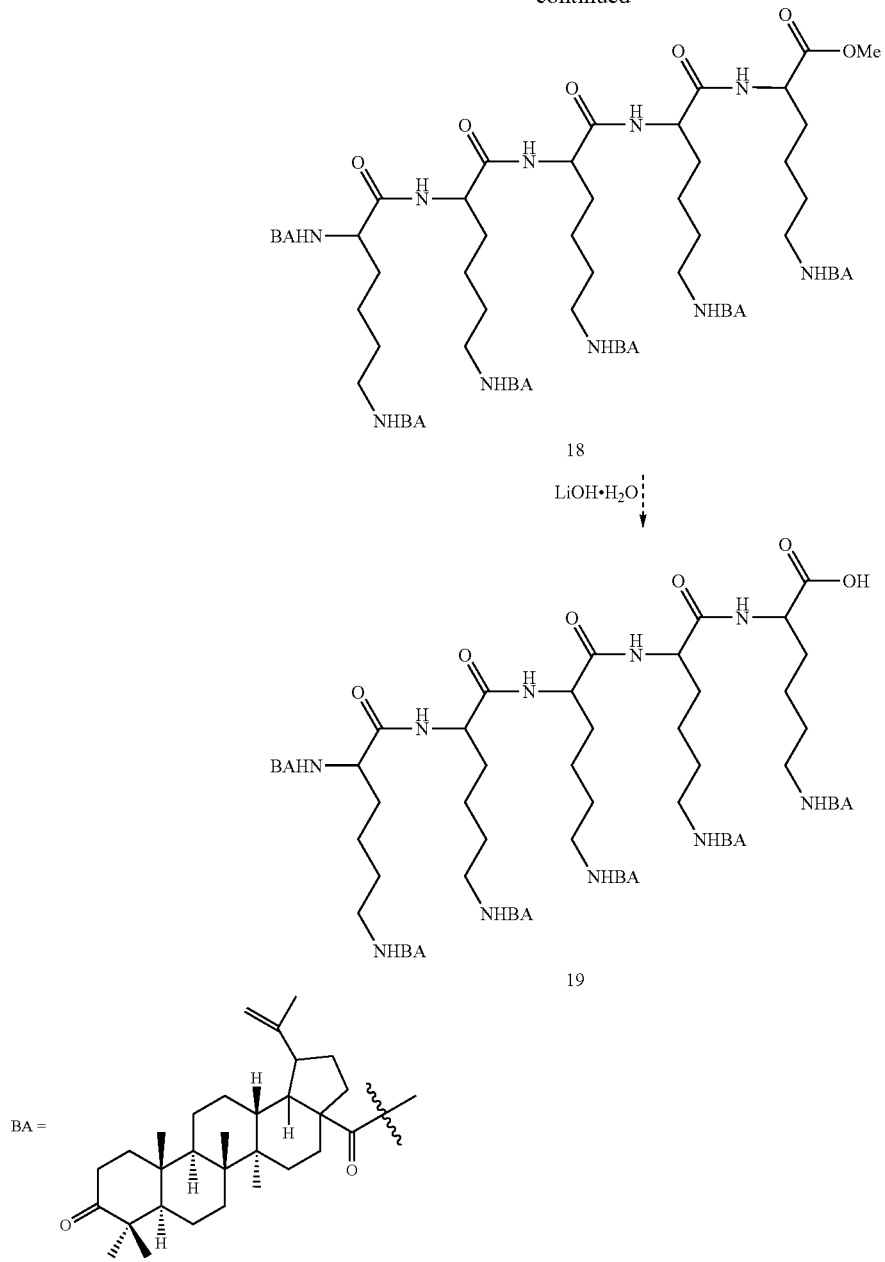

has C-1a carboxyl protected by ester with all other amines free to conjugate. In particular, pentalysine methyl ester (17) could react with six molecules of betulonic acid (3) and is catalyzed by DCC and HOBt to yield pentamer methyl ester of formula (18). Subjecting the ester to hydrolysis removes the methyl protecting group to generate pentamer of formula (19), which contains six molecules of betulonic acid. Pentamer (19) with six molecules of betulonic acid and free carboxyl can be used for immunoconjugation with an antibody.

Example 9

Immunoconjugates

Immunoconjugates of betulin derivatives were made by conjugation of α-globulin with lysinated betulonic acid. The synthetic structural modification strategy described previously is seen as a prelude to create sites for conjugation to a monoclonal antibody. As an exploratory feasibility study, monomer was conjugated with rabbit γ-globulin via an activated carboxyl group (COOH). Carbodiimide method is presently assessed. This bioconjugation reaction made use of different activated intermediates.

According to the carbodiimide method with 1,3-dicyclohexylcarbodiimide ("DCC"), monomers (13 mg, 0.02 mmol) as described above were dissolved in 0.2 mL of dry DMF with N-hydroxysuccinimide (NHS) (3.3 mg, 0.03 mmol) and a 20% molar excess of DCC. After 18 h of stirring at 4° C., the resulting activated ester was added slowly to the protein solution (10 mg of γ-globulin in 2 mL of 0.1 M carbonate buffer of pH 9.6) with vigorous stirring. The reaction mixture was stirred gently at 4° C. for 24 h to complete the conjugation and then dialyzed (Spectra/Por 7, Spectrum Laboratories) exhaustively against 250 mL of 0.01 M sodium phosphate buffer pH 7.2 containing 0.015 M NaCl (PBS) for 72 h with two exchanges of this buffer to give the monomer-antibody conjugate. The mixture was centrifuged (10,500 rpm) for 6 minutes and then supernatant was stored for cell cultures.

According to the carbodiimide method with 1-ethyl-3[3-diethylaminopropyl carbodimide ("EDC"), EDC solution (0.4 mg of EDC in 50 µL of DMF) and NHS solution (0.4 mg of NHS in 25 µL DMF) were freshly prepared and added to a monomer solution (0.2 mg of monomer in 500 µL of DMF). The reaction was kept at room temperature for 30 min and then kept at 4° C. overnight. The mixture was added slowly to 2 mg γ-globulin which was dialyzed against 250 mL of 0.1 M pH 9.4 carbonate buffer 4° C. 18 h. The reaction was carried out at 4° C. for overnight. The reaction mixture was dialyzed against 200 mL of 0.01 M phosphate buffer pH 7.2 containing 0.015 NaCl (PBS) for 72 h with two exchange of this buffer to give the monomer-antibody conjugate. The mixture was centrifuged (10,500 rpm) for 6 minutes and then precipitate was stored for cell culture.

Example 10

General Experimental Procedures

Chromatography

Flash column chromatography ("FCC") was performed using silica gel grade 9385 of 230-400 mesh (E. Merck). A stepwise solvent polarity gradient was employed. TLC was performed on aluminum sheets precoated with silica gel 60 (HE-254, E. Merck) to a thickness of 0.25 mm.

NMR Spectroscopy

Suitably pure products were taken on a Varian Inova AS 500 spectrometer operating at 500 MHz, equipped with a 5 mm triple resonance three axis gradient probe. Temperature calibrations were carried out using 100% methanol, with calibration values provide by Varian Instruments (Palo Alto, Calif.). Proton frequencies were reference to $CDCl_3$. NMR data processing and Varian Instruments carried spectral integration out using the VNMR software supplied. All NMR spectra were taken at NMR Core Facility Department of Chemistry, Hunter College, The City University of New York.

Mass Spectrometry

Accurate mass analysis obtained at the Biopolymer Mass Spectrometry Core Facility (Cornell University) was taken on a Micromass Quattro II triple quadrupole instrument with electrospray ionization in the positive ion mode. Samples were introduced by continuous infusion at a rate of 5 µL/min as a nominal 200 µM concentration solution in a 75:25:2 (v/v) acetonitrile/water/acetic acid solvent. When necessary, product ion spectra were obtained by maintaining argon gas in the collision chamber of the instrument at a pressure of $4 \times 10^{-3}$ mBar.

Gas Chromatography

To circumvent the problem of assessing the purity of betulin derived compounds, a rapid gas chromatographic method was developed. A 30 mm×25 mm×0.25 µm film thickness fused silica capillary column SAC-5 containing 5% phenyl and 95% dimethylpolysiloxane provides reproducible relative retention times for the betulin derivatives. All chromatographic analysis was performed on a Shimadzu Gas Chromatograph-14A with a typical setting:

| | |
|---|---|
| GC column: | SAC-5 Fused Silica Capillary Column containing 5% phenyl and 95% dimethyl polysiloxane; 30 mm × 25 mm × 0.25 µm file thickness; Conditioned overnight prior to all sample run |
| Flow rate: | 60 mL/min |
| Gas pressure: | Air (50 kPa); $H_2$ (55 kPa); p1 (80 kPa); p2 (150 kPa) |
| Temperature: | 300° C. injector/column/detector |
| Injector: | Split |
| Detector: | FID |
| Vol. of sample: | 8 µL in chloroform. |

Example 11

Standard Solubility Curve of Betulonic Acid

In order to determine the solubility of betulonic acid and its derivatives in various solvents, a standard solubility curve of various concentration of betulonic acid in chloroform (Table 5) versus corresponding peak area from gas chromatogram was generated.

TABLE 5

Standard Solubility Curve of Betulonic Acid in Chloroform

| Concentration of BA (mol/L) | Concentration of BA (mg/mL) | Peak Area ($\times 10^{-4}$) |
|---|---|---|
| 0.5 | 227 | 286.5 |
| 0.25 | 113.5 | 78.0 |
| 0.125 | 56.8 | 46.8 |
| 0.0625 | 28.4 | 51.4 |
| 0.01 | 4.5 | 17.4 |
| 0.005 | 2.3 | 5.3 |
| 0.001 | 0.5 | 9.5 |

Figure 5:
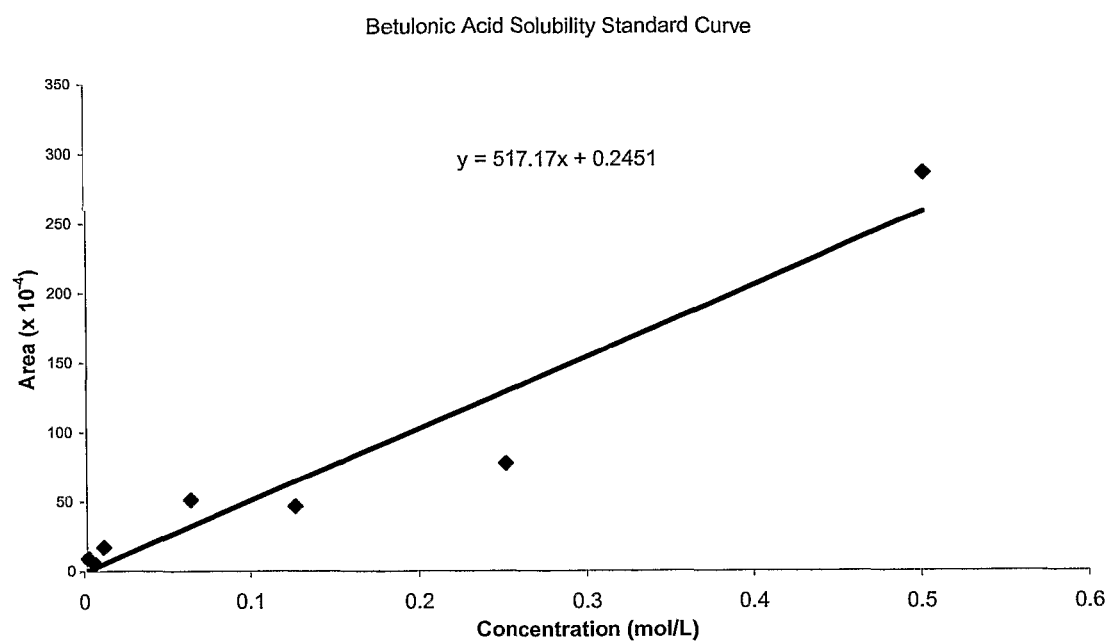
FIG. 5 is a graph showing the standard solubility curve of betulonic acid concentration versus peak area.

8 µL of each known concentration of betulonic acid and solution with unknown concentration were analyzed by gas chromatography ("GC"). The standard solubility curve of betulonic acid concentration versus peak area is shown in FIG. 5. Solvents containing unknown concentration of betulonic acid were evaporated. The residue was dissolved in chloroform analyzed on GC. The concentration of betulonic acid unknown concentration was determined from the standard curve by using the corresponding peaks in the chromatogram.

The standard solutions of betulonic acid were prepared as follows. 45.4 mg of betulonic acid was dissolved in 200 µL neat chloroform to yield 0.5 mol/L concentration of betulonic acid. After three times of double dilution, three different known concentrations (0.25 mol/L, 0.125 mol/L, and 0.0625 mol/L) of betulonic acid were obtained. 2.27 mg of betulonic acid was dissolved in 500 µL neat chloroform to yield 0.01 mol/L concentration of betulonic acid. Double dilution of this solution generated a 0.005 mol/L concentration of betulonic acid. 0.227 mg of betulonic acid was dissolved in 500 μL neat chloroform to yield 0.001 mol/L concentration of betulonic acid.

Example 12

Solubility of Betulonic Acid and its Derivatives in DMSO Diluted with Culture Medium 3 mg of betulonic acid was dissolved in 200 μL of neat DMSO. Betulonic acid solution in neat DMSO was then diluted with culture medium containing 10% Fetal Bovine Serum ("FBS") to yield a 1% concentration of to obtain a $1\times10^{-3}$ mol/L (0.5 mg/mL) concentration of betulonic acid. Since the betulonic acid was not completely dissolved, suspension was centrifuged at 10,500 rpm for 5 min. The concentration of betulonic acid in the precipitate and the supernatant was determined from a standard solubility curve. Only 0.4 mg out of 3 mg of betulonic acid was dissolved. The remaining 2.6 mg of betulonic acid was precipitate. Hence, 13% betulonic acid was completely soluble.

Since 1% DMSO in culture medium was not sufficient to solubilize 3 mg of betulonic acid, the concentration of DMSO in culture medium was increased stepwise to completely dissolve betulonic acid. Results of this stepwise increase of DMSO experiment are set forth in Table 6.

TABLE 6

Results of Stepwise Increase in DMSO Concentration Experiment

|  | 1 | 2 | 3 | 4 |
|---|---|---|---|---|
| BA (mg) | 0.5 | 0.5 | 0.5 | 0.5 |
| Vol. of Neat DMSO to dissolve BA (μL) | 33 | 103 | 153 | 220 |
| Vol. of Culture Medium (mL) | 1.07 | 1.0 | 0.95 | 0.88 |
| Total Vol. After dilution (mL) | 1.1 | 1.1 | 1.1 | 1.1 |
| Con. of BA (mg/mL) | 0.5 | 0.5 | 0.5 | 0.5 |
| Con. of BA (mol/L) | $1 \times 10^{-3}$ | $1 \times 10^{-3}$ | $1 \times 10^{-3}$ | $1 \times 10^{-3}$ |
| % of DMSO in total Vol. | 3% | 9% | 14% | 20% |
| State of solution | Suspension | Suspension | Cloudy | Clear Solution |

It is shown in Table 6, that 220 μL neat DMSO diluted to 20% with the culture medium was able to dissolve 0.5 mg betulonic acid and its derivatives completely to yield a clear solution.

Each solution of betulonic acid and its derivatives was lyophilized and extracted with ethyl ether. Ethyl ether was then evaporated. The residue containing betulonic acid and/or its derivatives were re-dissolved in chloroform and analyzed on GC. Concentration of drug in the above solutions was analyzed by GC and determined from the standard solubility curve. The concentration of betulonic acid and/or its derivatives in 20% DMSO in culture medium was calculated as shown in Table 7.

TABLE 7

Concentration of BA or Derivatives in 20% DMSO

|  | Amount of drug (mg) | Volume of Culture Medium containing 20% DMSO (mL) | Concentration of drug (mg/mL) | Concentration of drug (mol/L) |
|---|---|---|---|---|
| Boc-Monomer | 1.0 | 1.5 | 0.7 | $1 \times 10^{-3}$ |
| Boc-Dimer | 1.0 | 1.6 | 0.6 | $5 \times 10^{-4}$ |
| Boc-Tetramer | 1.0 | 1.7 | 0.6 | $2.5 \times 10^{-4}$ |

The concentrations of betulonic acid determined by GC were close to the calculated values (Table 8), thus confirming that most of betulonic acid and/or its derivatives were completely solubilized.

TABLE 8

Calculated Concentration Values of Betulonic Acid and Derivatives

| | 1 | 2 | 3 | 4 |
|---|---|---|---|---|
| Compound name | Betulonic Acid | Boc-Monomer | Boc-Dimer | Boc-Tetramer |
| Con. in culture medium containing 20% DMSO (mol/L) | $1 \times 10^{-3}$ | $1 \times 10^{-3}$ | $5 \times 10^{-4}$ | $2.5 \times 10^{-4}$ |
| Con. of betulonic acid portion (mol/L) | $1 \times 10^{-3}$ | $1 \times 10^{-3}$ | $1 \times 10^{-3}$ | $1 \times 10^{-3}$ |
| Total Volume (mL) | 1.4 | 0.75 | 0.75 | 0.93 |
| Chloroform (μL) | 100 | 100 | 100 | 100 |
| Area of GC spectrum (×10$^{-4}$) | 6.9 | 4.0 | N/A | 3.7 |
| Cal. Con. of betulonic acid (mol/L) | $0.92 \times 10^{-3}$ | $0.97 \times 10^{-3}$ | N/A | $0.72 \times 10^{-3}$ |

These experiments provided accurate solubility of the compounds in DMSO in culture medium for in vitro cytotoxicity assay.

Example 13

Solubility of Betulonic Acid in Ethanol and Culture Medium

Ethanol was chosen as a biocompatible solvent for use in in vivo studies. Up to 43.3 mg of betulonic acid was completely dissolved in 1 mL of neat (100%) ethanol to yield a saturated solution. This solution can be diluted with culture medium to yield 0.8 mg of betulonic acid completely dissolved in 1.76 mL of culture medium containing 10% human serum with 10% ethanol concentration to generate a concentration of $1 \times 10^{-3}$ mol/mL (0.5 mg/mL) of betulonic acid.

Example 14

Solubilization of Betulonic Acid in Phosphate Buffered Saline (PBS) Containing Human γ-Globulin, Human Albumin and Ethanol Human γ-Globulin and human albumin are two major biocompatible components in human serum. Betulonic acid was dissolved in neat ethanol and diluted with PBS containing various concentrations of γ-globulin and Albumin (Table 9).

TABLE 9

Dilution of BA with PBS at Various Concentrations

| Betulonic Acid (mg) | Ethanol (μL) | Human γ-globulin (27 mg/mL in PBS) (mL)* | Human Albumin (42 mg/mL in PBS) (mL)* | Con. (mol/L) | Observation |
|---|---|---|---|---|---|
| 1.3 | 280 | 2.50 | 0 | $1 \times 10^{-3}$ | Suspension |
| 1.0 | 220 | 1.48 | 0.49 | $1 \times 10^{-3}$ | Cloudy |
| 1.5 | 330 | 1.48 | 1.48 | $1 \times 10^{-3}$ | Little Cloudy |
| 1.4 | 308 | 0.69 | 2.07 | $1 \times 10^{-3}$ | Almost Clear |
| 1.6 | 352 | 0.32 | 2.85 | $1 \times 10^{-3}$ | Clear Solution |
| 1.3 | 280 | 0 | 2.50 | $1 \times 10^{-3}$ | Complete Clear |

*Percentage of human γ-globulin or human albumin in PBS is the same as in human serum.

As shown in Table 9, betulonic acid could be dissolved in PBS with increasing concentration of human albumin. It was completely dissolved in human albumin PBS solution with 10% ethanol to yield a $1 \times 10^{-3}$ mole/L concentration of betulonic acid.

Example 15

Solubility of Betulonic Acid in Human Serum

Betulonic acid dissolved in neat ethanol was diluted with neat human serum to sustain it in solution as shown in Table 10.

TABLE 10

BA Dissolved in Neat Ethanol Diluted with Human Serum

| Betulonic Acid (mg) | Vol. of Ethanol (M.L) | Vol. of Human Serum (μL) | Total volumn (mL) | Con. of Betulonic Acid (mol/L) | Con. of Betulonic Acid (mg/mL) | Observation |
|---|---|---|---|---|---|---|
| 1.34 | 31 | 700 | 731 | $4 \times 10^{-3}$ | 1.8 | Clear Solution |

The results of Table 10 show that 1.34 mg betulonic acid was dissolved in 31 μL neat ethanol and diluted with human serum to yield a 4.2% final concentration of ethanol and a $4 \times 10^{-3}$ mol/L concentration of drug. The compounds remained soluble and are suitable for in vivo studies.

In addition, betulonic acid and its lysinated derivatives may be completely dissolved in neat ethanol and diluted with PBS containing 4% human albumin (similar to the concentration of albumin in human serum) to achieve a final concentration of 10% ethanol to yield a $1 \times 10^{-3}$ mol per liter concentration of betulonic acid. The results of in vitro studies are consistent with previous results. In vivo study, solubilized betulonic acid and monomer-Boc at a final concentration of 22% ethanol and $2 \times 10^{-3}$ mol per liter of betulonic acid are well tolerated by mice with prostate cancer cell xenografts.

Addition of 10% glycerol further facilitated betulonic acid and its derivatives in solution for extended periods of time.

Example 16

Cytotoxicity of Betulonic Acid and Derivatives on Prostate Cancer Cells: Assessment of Cell Viability The human prostate cancer LNCaP, PC-3, and DU-145 cell lines, as well as human fibroblast cell line, were obtained from the American Type Culture Collection ("ATCC") and maintained in RPMI-1640, F-12k, and MEM mediums, respectively, supplemented with 10% FBS. Cell lines were maintained at 37° C. under a humidified atmosphere and 5% $CO_2$ for testing of the cytotoxicity of betulinol derivatives. The cytotoxicity assay was performed using MTT assay according to the instructions of ATCC protocol. Cells $1 \times 10^5$ in 0.1 ml/well were plated in 96-well culture plates (Costar) and incubated with a different dilution of betulinol derivatives for 24, 48, and 72 hours. Ten μl of 3-[4,5-dimethylthiazol-2-yl]-2,5 diphenyl tetrazolium bromide was added into each well at the end of each incubation period. The reaction product, formazan, was dissolved in the detergent, and the absorbance was read at 540 nm (Ref).

Example 17

Anchorage-independence Growth Assay

Anchorage-independence growth assay was performed to determine the ability of cancer cells to form colonies in soft agar. $1.0 \times 10^4$ cancer cells were suspended in 2 ml of DMEM medium containing 0.33% agar in the presence or absence of betulinol derivatives. The compounds were overlaid on a 2 ml matrix made up of 0.6% agar. The cultures were incubated at 37° C. in a humidified environment under 5% $CO_2$ for 14 days without medium change. The cultures were fixed in Cornoy's fixative (acetic acid/100% ethanol 1:3 v/v) and the numbers of anchorage-independent, tridimentional colonies ($\geqq 40$ μm diameter) formed were counted under 10× magnification (Katdare et al., *Cancer Lett.* 111:141-47 (1997), which is hereby incorporated by reference in its entirety).

Example 18

In Vivo Anti-tumor Studies (LNCaP Prostate Cancer Xenografts in Athymic Mice)

All the animal studies were performed according to the guidelines and approval of the Institutional Animal Care and Use Committee and Research Animal Resource Center of Weill Medical College of Cornell University, New York. Twelve mice of 13 weeks of age were purchased from The National Cancer Institute (NCI) and were housed in a pathogen-free environment under controlled conditions of light and humidity and with free access to food and water. LNCaP cells were grown in RPMI-1640 with 10% FBS until 80-90% confluent. Cells were scraped into PBS and collected by centrifugation. The LNCAP cell pellets were suspended in Matrigel (Ref) at $2.5 \times 10^7$ cells/ml. Mice were injected subcutaneously ("s.c.") with 200 μl ($5 \times 10^6$ cells) of the cell suspension at one site on the flank. Visible tumor grew after 7-8 days following implantation and mice were divided into three groups of four mice each.

Betulonic acid was dissolved at 2.5 mg/ml solution in 1% DMSO in PBS. Mice received s.c. injection daily for ten days. The control groups received solvent alone while the other group received betulonic acid in 200 μl of the solvent (20 mg/kg). Tumors were measured daily with calipers, and tumor volumes were calculated by the formula: $\pi/6(l \times w \times h)$. Animals were also weighed daily and monitored for general health status and vital signs of possible toxicity due to treatment. At the end of the treatment period, the animals were sacrificed and tumors were excised, weighed and prepared for immunohistochemical and histological studies.

Another twelve athymic female mice were s.c. injected 10 million LNCaP cells each and divided into four groups of three mice each. Control group was injected solvent alone as control after 24 hours inoculation while mice in treatment group were injected with betulonic acid at 0.5 mL containing $10^{-2}$ and $10^{-3}$ molar of betulonic acid. Mice were sacrificed on day 10 and the tissues were subjected to histological examination.

Example 19

Immunohistochemical Studies of Tumors

All the mice were sacrificed at the end of the treatment and a portion of the tumor from each mouse was immediately frozen in liquid nitrogen. The frozen sections of the tumor tissue were examined immunohistochemically using antibodies against prostate specific antigen (PSA) and prostate specific membrane bound antigen (PSMA) since PSA and PSMBA are the recognized markers for LNCaP prostate cancer cells. This staining provides a means of identifying membrane bound antigen in prostate cancer cells and allows monitoring of changes in the tumor (Liu et al., *Cancer Res.* 57:3629-3634 (1997), which is hereby incorporated by reference in its entirety).

Another portion of the tumor tissue was fixed in 4% formalin, and transferred to 70% ethanol for histological examination for cell types and structure.

Example 20

Cytotoxicity of Betulonic Acid and its Derivatives on Human Prostate Cancer Cells A series of compounds were synthesized chemically by modifying the structure of betulinol as shown in Table 1. Compounds 2, 3, 4, and 5 were tested in vitro for cell toxicity by NCI to determine their cell growth inhibitory properties against different human tumor cell lines including, melanoma, bladder cancer, breast cancer, CNS cancer, lung cancer, ovarian cancer, prostate cancer, and renal cancer. Compound 5 showed the most effective inhibition of cell growth without selective activity. However, these compounds were not tested on prostate cancer LNCaP cell line by NCI. Compounds 1, 2, 3, 4, 5, 6, 7, and 8 were evaluated in human prostate tumor cell LNCaP by MTT assay. The anti-tumor activity of the compounds was determined at three doses and the total growth inhibition kill effect as pertinent of the control at 24, 48, and 72 hours as presented in Table 11. Betulonic acid showed the highest kill effects on LNCAP cell growth compared to the other compounds.

TABLE 11

Growth Inhibition % of Betulonol Derivatives in LNCaP Cell Line

| | 24 hours | | | 48 hours | | |
|---|---|---|---|---|---|---|
| Compound | $2.5 \times 10^{-7}$ (M) | $2.5 \times 10^{-6}$ (M) | $2.5 \times 10^{-5}$ (M) | $2.5 \times 10^{-7}$ (M) | $2.5 \times 10^{-6}$ (M) | $2.5 \times 10^{-5}$ (M) |
| 1 | 8.24 | 11.9 | 47.2 | 10.6 | 13.8 | 31 |
| 2 | 11.72 | 24.6 | 41.0 | 62.8 | 69.4 | 73.3 |
| 3 | 6.34 | 11.0 | 29.5 | 27.6 | 40.9 | 72.3 |
| 4 | 3.01 | 14.7 | 11.4 | 28.3 | 43 | 32.65 |
| 5 | 6.34 | 21.9 | 19 | 29.8 | 47.4 | 40.2 |
| 6 | 0 | 18.7 | 17 | 27.9 | 46.7 | 56.6 |
| 7 | 7.76 | 18.1 | 45 | 27.9 | 44.0 | 50.9 |
| 8 | 0 | 10.4 | 12.4 | 17.4 | 44.7 | 28.3 |

To confirm the specific anti-tumor activity of betulonic acid, betulonic acid was evaluated on fibroblasts as well as different prostate cell lines like DU-145 and PC-3 cells. Results are shown in Table 12.

TABLE 12

Growth Inhibition % of BA on Prostate Tumor Cell Lines

| Cell Lines | 24 hours $1 \times 10^{-5}$ | 48 hours $1 \times 10^{-5}$ |
|---|---|---|
| LNCaP | 38 ± 8 | 75 ± 9 |
| DU-145 | 33 | 51 |
| PC-3 | 9.7 | 41.1 |
| Fibroblasts | 0 | 0 |

As shown in Table 12, betulonic acid did also inhibit growth of all three kinds of prostate cancer cells. However, betulonic acid showed the most effective inhibition of LNCaP cell growth. Betulonic acid has no cytotoxic effect on normal fibroblasts cells. Therefore, LNCaP cells were chosen for further dose-dependent study of betulonic acid.

Betulonic acid also inhibited the growth of LNCaP cells with dose-dependent pattern at 24, 48, and 72 hours of incubation, as shown in Table 13.

TABLE 13

Growth Inhibition % of BA on LNCaP Prostate Tumor Cells

| Time (hours) | $1 \times 10^{-6}$ | $1 \times 10^{-5}$ | $1 \times 10^{-4}$ (M) |
|---|---|---|---|
| 24 | 9.2 ± 6.1 | 24.2 ± 10.8 | 70.4 ± 19.1 |
| 48 | 27.75 ± 11.4 | 69.5 ± 20.2 | 81.0 ± 12.6 |
| 72 | 45.0 ± 12.3 | 88.4 ± 7.96 | 80.8 ± 15.8 |

As shown in Table 13, the cytotoxicological effect of betulonic acid at the concentration of $1 \times 10^{-5}$ and $1 \times 10^{-4}$ M on LNCaP cells for 24 hr incubation was 24.2±10.8% and 70.4±19.1% in the MTT assay. The cytotoxicological effect increased to 69.5±20.2% and 81±12.6% after 48 hrs incubation. Betulonic acid at low concentration $1 \times 10^{-6}$ M showed high inhibition of cell growth after 48 and 72 hours incubation compared to that for 24 hours incubation. Betulonic acid at the same concentration had little cytotoxicological effect on normal fibroblast cells.

Lysinated betulonic acid was also cytotoxic to LNCaP prostate tumor cells. Betulonic acid linked with one lysine (Monomer) (Table 14) could inhibit the LNCaP cell growth by 36.75% at the concentration of $1 \times 10^{-5}$ M after the cells were treated with the compound for 48 hours whereas at the drug concentration to $1 \times 10^{-4}$ M almost 80% cells were killed.

TABLE 14

Growth Inhibition % of Betulonic Acid Conjugated with Lysine on LNCaP Prostate Tumor Cells

| Time (hours) | $1 \times 10^{-6}$ | $1 \times 10^{-5}$ | $1 \times 10^{-4}$ (M) |
|---|---|---|---|
| 24 | 5.5 ± 7.32 | 19.0 ± 14.4 | 76.5 ± 22.6 |
| 48 | 15.0 ± 11.2 | 36.75 ± 19.2 | 82.75 ± 14.3 |
| 72 | 17.25 ± 32.5 | 40.5 ± 33.6 | 79.25 ± 16.5 |

As shown in Table 15, betulonic acids with two lysines (Dimer) showed a higher kill effect on LNCAP cells than Monomer. At the low concentration of $5 \times 10^{-6}$ M, the dimer showed a 34.5% kill effect after 48 hours incubation with cells.

TABLE 15

Growth Inhibition % of Betulonic Acid Conjugated with Two Lysines on LNCaP Prostate Tumor Cells

| Time (hours) | $5 \times 10^{-7}$ | $5 \times 10^{-6}$ | $5 \times 10^{-5}$ (M) |
|---|---|---|---|
| 24 | 13.5 ± 17.4 | 24.0 ± 22.3 | 67.5 ± 22.8 |
| 48 | 14.75 ± 13.9 | 34.5 ± 20.9 | 78.25 ± 18.1 |
| 72 | 20.0 ± 16.3 | 33.75 ± 16.4 | 85.25 ± 7.84 |

Example 21

Effects of Betulonic Acid on the Growth of the Human Prostate Cancer Cell Colonies in Soft Agar: Anchorage Independent Assay The minimum effective dose of betulonic acid was used in the soft agar colony-forming assay to evaluated the effect of betulonic acid on anchorage-independent growth of three prostate cancer cell lines DU145, LNCaP, and PC-3. Cancer cells were suspended in soft agar with $1 \times 10^{-5}$ M betulonic acid. Betulonic acid exhibited a decrease in anchorage-independent colony formation growth during 14 days of continuous exposure to corresponding untreated controls (LNCaP: FIGS. 6A-D; DU145: FIGS. 7A-B; PC3: FIGS. 8A-C). A non-transformed normal fibroblast cell line did not form any colony, either in control group or in the treated group (FIG. 9).

The treated cells exhibited a very significant difference in the size of colonies formed, indicating that betulonic acid arrested the growth of cells, thereby reducing the size of colonies. Interestingly, control cells grew as 3D tubular structures, representing a very high metastatic nature of these cells. Treated cells totally lacked this capability.

PC-3 cells exhibited higher sensitivity to the drug compared to the control (Table 16).

TABLE 16

Inhibition % of BA on Anchorage-independent Growth at $1 \times 10^{-5}$ M

| Cell lines | DU-145 | PC-3 | LNCaP |
|---|---|---|---|
| Betulonic acid | 12.5 | 26.1 | 0 |

The size of the colony formed in the treated group was smaller compared with control, indicating inhibition of growth by betulonic acid.

Example 22

Effects of Betulonic Acid on LNCaP Xenografts Grown in Athymic Mice

Figure 10:
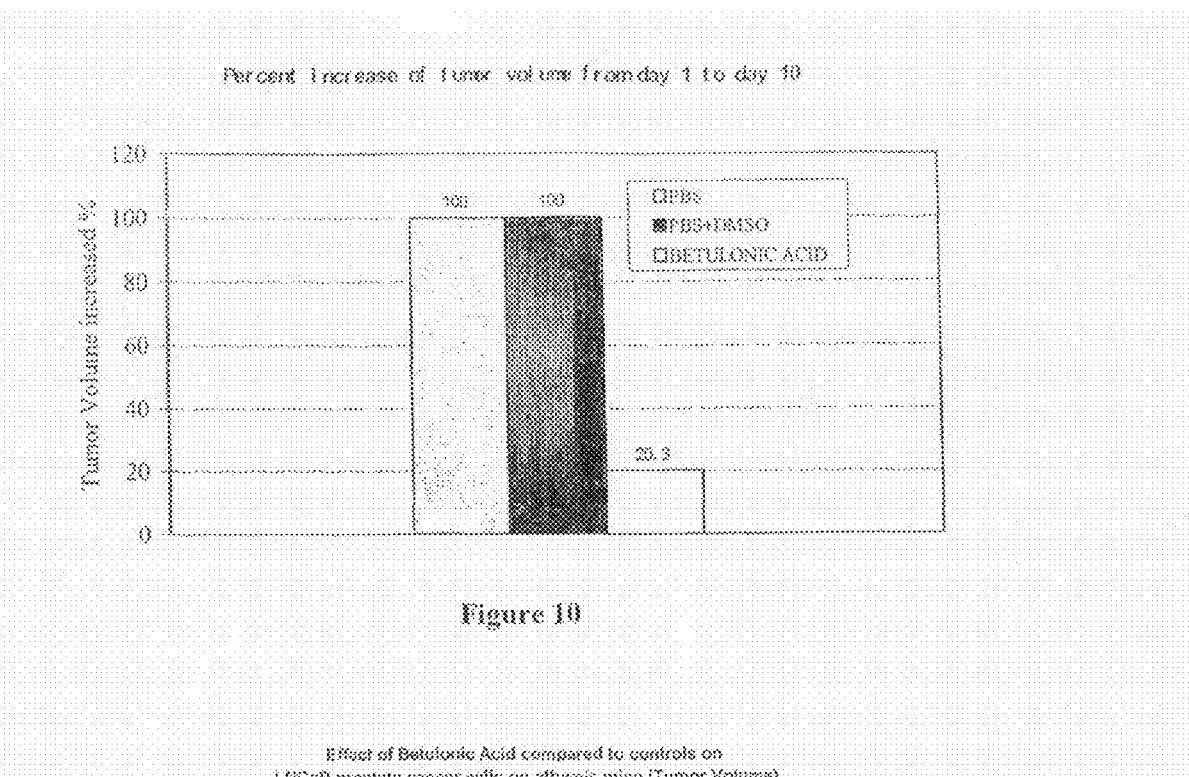
FIG. 10 is a graph showing the effects of betulonic acid on LNCaP xenografts grown in athymic mice. In particular.
Figure 11:
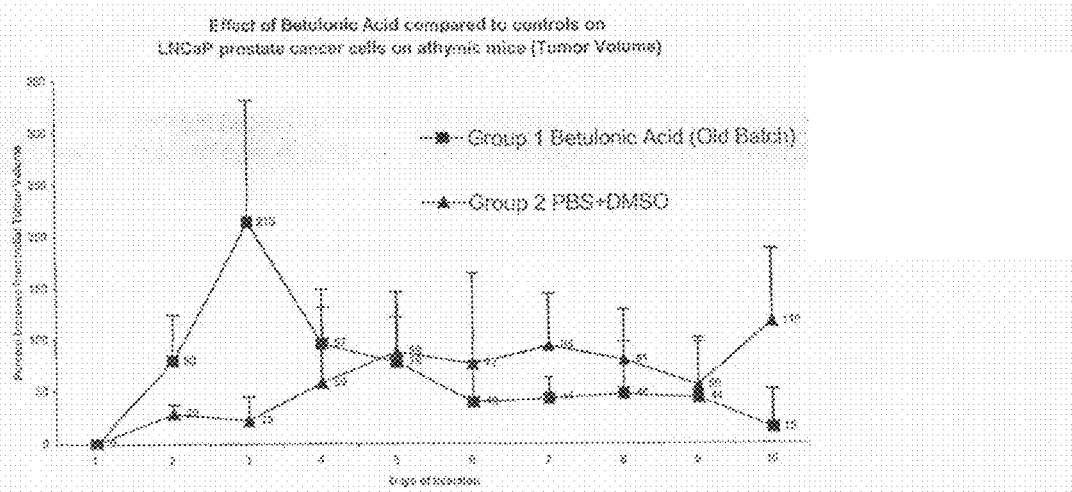
FIG. 11 is a graph showing the effect of betulonic acid compared to controls on LNCaP prostate cancer cells on athymic mice.

Tumors were developed from LNCaP cells implanted inoculated subcutaneously in athymic mice. Betulonic acid was administrated continuously for 10 days. Throughout the entire duration of the experimental procedure, mice appeared healthy, alert, and showed no adverse effects on vital signs. The tumor volume of control groups after 10 days treatment almost doubled compared to the tumor volume on the first day of injection. The tumor volume in betulonic acid group on day 10 increased only 20.3% compared to that on day 1 (FIG. 10). The percent change of tumor volume are presented from day 1 to 10 (FIG. 11). Tumor volume in the control group increased consistently until day 10. However, the treatment group showed consistent decreased tumor volume after the third day administration of betulonic acid till day 10.

Example 23

Immunohistochemical Studies of Tumors Section

Frozen sections of the tumors were checked by immunocytochemical staining with antibodies against prostate specific antigen ("PSA") and prostate specific membrane bound antigen ("PSMA") as described earlier (Liu et al., *Cancer Res.* 57:3629-3634 (1997), which is hereby incorporated by reference in its entirety). At the low dose of the drug, the cells showed the presence of the antigen, but the viability of these cells in cell culture was not tested. However, no PSA and PSMA antigen was detected in the tumor of the mice injected with high dose of the drug indicating that most of the cells were not viable and presumably destroyed.

Example 24

Histochemical Examination of Hematoxylin-Eosin Stain of Tumor Sections

There was more invasion of histolytic macrophages and necrotizing inflammation due to foreign body reactions. Inflammation and necrosis also did not allow accurate measurement of the tumor volume from day 10 onwards until day 21.

Example 25

Alternative Synthesis Method of Betulonic Acid Pentamer Conjugated with IgG/Fab

Derivation of Betulonic Acid from Betulin Via Jones Reagent

Starting off with Betulin (10 g) in acetone (300 mL), add freshly prepared Jones Reagent added dropwise at 0° C. Stir for 5 hours, quench with methanol (100 mL), then stir for 5 minutes and add $H_2O$ (200 mL). Remove organic solvent under vacuum, and then separate the precipitate by filtration. Wash precipitate on the filter with cooled water, and dry to obtain crude material. This dry material is to be dissolved in 30 mL benzene. The solution is then filtered through a layer of aluminum oxide and the eluate is treated with an aqueous 10% KOH solution until complete precipitation. The precipitate is then separated by filtration, washed with 10 mL cooled benzene, and dried to obtain white solid. The salt is dissolved in 30 mL methanol and the solution is poured into 100 mL 15% aqueous HCL solution. The betulonic acid (2.7 g) is obtained after the precipitate is filtered, washed with water, and dried.

Preparation of Jones' Reagent: To pink solid $CrO_3$ (11.2 g) add 10 mL $H_2SO_4$. Slowly pour water (44 mL) into this suspension at 0° C. After the solid is completely dissolved, the red solution is ready to use.

Alternate Derivation of Betulonic Acid via Hydrogen Peroxide

To a suspension of freshly activated powdered 4A molecular sieves (1.2 g), celite (1.2 g), florisil (1.2 g), sodium acetate (500 mg) and pyridinium chlorochromate (1.2 g) in $CH_2Cl_2$ (25 mL) add betulin (500 mg). The mixture is to be stirred for 2 hrs, and then filtered through a short column of silica gel. The filtrate is evaporated in vacuo. The residue is then subjected to column chromatography to afford betulone aldehyde (370 mg) as white solid.

The betulone aldehyde prepared from the last step is dissolved in a mixture of $NaH_2PO_4 \cdot H_2O$ (877 mg) and $CH_3CN-H_2O$ (17 mL) and the suspension cooled to 0-5° C. 30% aqueous $H_2O_2$ (220 µL) and a solution of $NaClO_2$ (200 mg) in water (16 mL) are then successively added, the mixture warmed to room temperature and stirred at this temperature for 1 h. The reaction is quenched by addition of $Na_2S_2O_5$ (380 mg), and extracted with ethyl acetate. The organic extract is washed with water and brine, dried ($Na_2SO_4$), filtered, and concentrated. The residue is then subjected to column chromatography to afford betulonic acid (550 mg) as white solid.

Conjugation of Betulonic Acid to Pentalysine

Prophetic Example

Next, starting off with blocked pentalysine triglycine (blocked with a T-butyl ester on the C-Terminus) add betulonic acid. Add HATU coupling reagent, and DIEA. Add DMF until completely dissolved. Stir until TLC shows complete production of Pentamer. Separate final product via column chromatography, wash and dry product.

Deprotection of Pentamer

Prophetic Example

Add to 5 mmol solution of protected pentamer with acetonitrile some montmorillonite KSF clay (mass of clay=1 g per 10 mL solution) stir at reflux temperature until TLC indicates completed reaction (<5 hours).

Conjugation of Pentalysine to Antibody/Antibody Fragment

Prophetic Example

Using the Woodward's Reagent K Method as illustrated below:

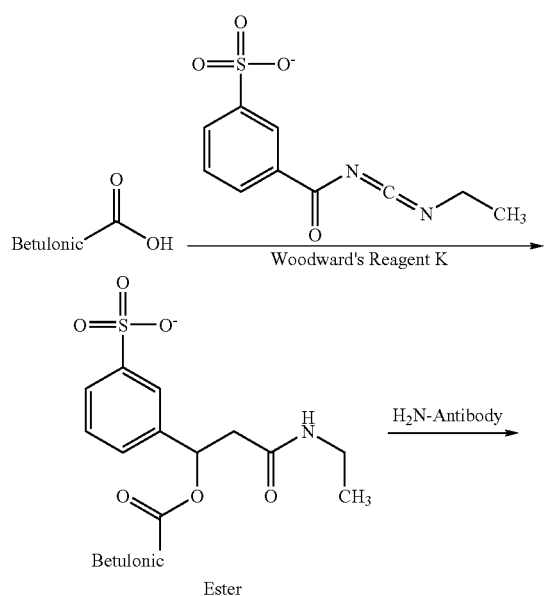

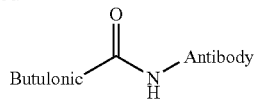

Add the deprotected Pentamer to a solution containing Woodward's Reagent K, stir and after TLC Analysis shows completion of reaction, add Antibody and stir until completion.

Example 26

Mice Study

Figure 12:
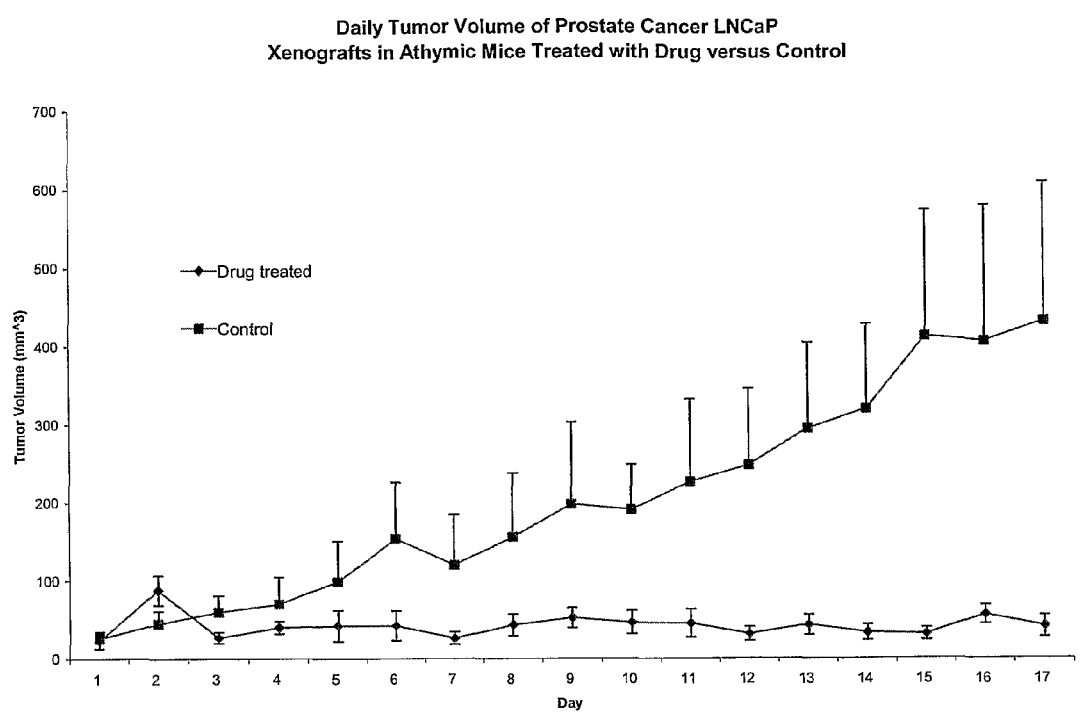
FIG. 12 is a graph showing daily tumor volume of prostate cancer LNCaP xenografts in athymic mice treated with drug versus control.
Figure 13:
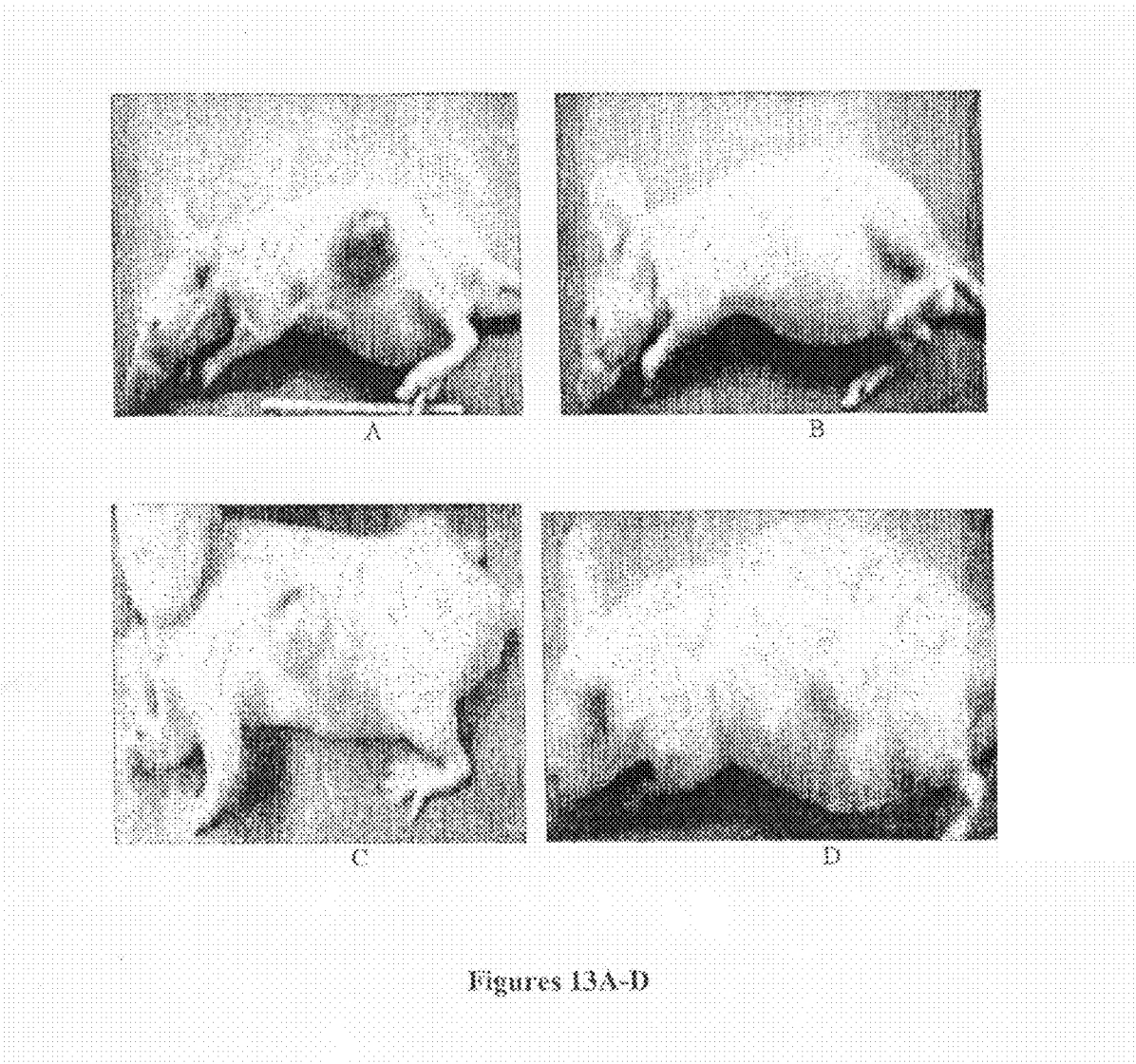
FIGS. 13A-D are photographs showing the effect of lysinated betulonic acid (monomer) on the growth of LNCaP prostate cancer tumors (xenografts) in male athymic mice. The mice shown in FIG. 13A and FIG. 13C are control (untreated) and the mice shown in FIG. 13B and FIG. 13D are treated.
Figure 14:
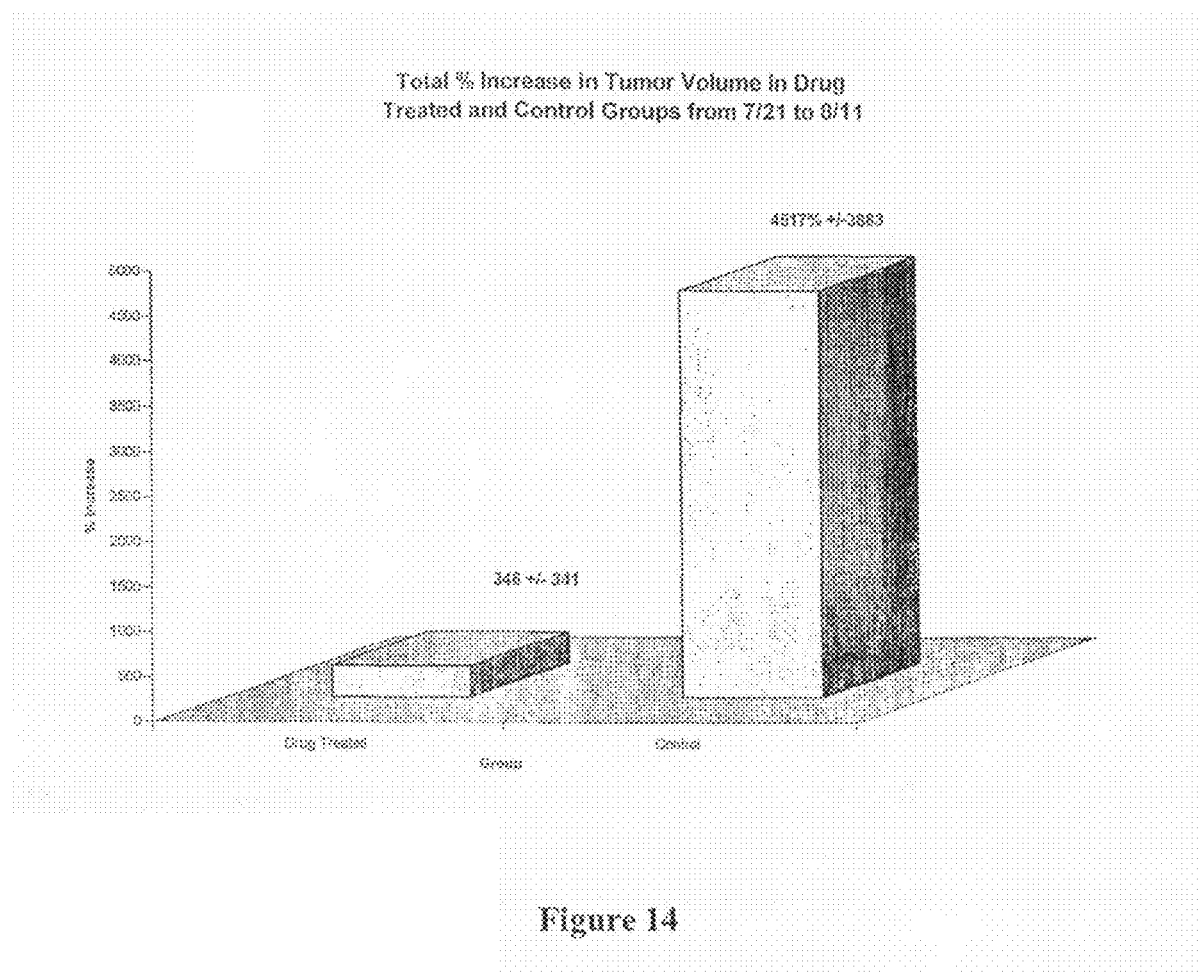
FIG. 14 is a graph showing total percent increase in tumor volume in drug treated and control groups of prostate cancer LNCaP xenografts in athymic mice.

In the present experiment, twelve male athymic mice were utilized. Seven to ten million cells, from a prostate cancer LNCaP cell line culture, were suspended homogenously in a Matrigel basement membrane matrix and transplanted in mice as xenografts. Tumors were visible within a week. Mice were injected daily with a lysinated betulonic acid. Control groups of mice were also injected daily with a solution containing 22% ethanol in phosphate buffer solution (PBS) containing 4% albumin for a duration of 24 days. The mice were weighed daily to the tenth of a gram and mice were observed for any abnormal vital signs or adverse behavior. The volume of the tumors was determined daily using a caliper in order to observe any change in the tumor volume (FIG. 12), calculated according to the formula $\pi/6$ (l×w×h). Mice were sacrificed by $CO_2$ asphyxiation on day 24 after the first injection (FIGS. 13A-D). Total percent increase in tumor volume in drug treated and control groups was assessed (FIG. 14).

The tumors were dissected out. A portion of the tumors was frozen immediately in optimal cutting temperature gel (OCT gel) at −80° C. Frozen sections of the tumor were cut and placed onto slides and stained. The tumor sections were examined immunohistochemically for the presence or absence of prostate specific antigen (PSA) and prostate specific membrane bound antigen (PSMBA) using specific antibodies to determine the viability of the cells. These antigens (PSA and PSMBA) are the markers for LNCaP prostate cancer cells.

Another portion of the tumor tissue was fixed in 4% formalin, and transferred to 70% ethanol. After 24 hours, sections of the fixed tissue were cut and stained with hematoxylin eosin for histological examination for cell types and structure.

Ex vivo growth of tumors was assessed using a three-dimensional culture system (matrigel). A third section of the tumor was cut into very small pieces placed in a culture plate immersed in a solution containing a one to one ratio of matrigel basement membrane matrix and RPMI culture medium. Culture medium was added in to the wells after the matrigel solution solidified. Tumor pieces were cultured for 12 days and pictures were taken every day using Olympus IX 70 inverted microscope and DP11 image analyzer. On day 5 of culture, the drug was added to the experimental tumor group. Apoptosis was evaluated with both Western blot (cleaved caspase-3) and yo-pro-1 in immunofluorescence (FIGS. 15A-N and FIGS. 16A-N).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A method of treating a cancer selected from the group consisting of prostate cancer, renal cancer, breast cancer, ovarian cancer, CNS cancer, melanoma, lung cancer, and bladder cancer, said method comprising:

administering to a subject having the cancer a compound of Formula I

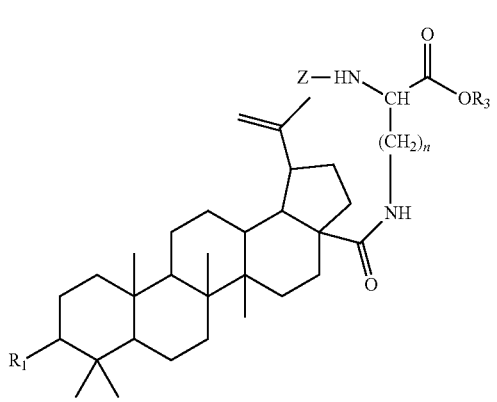

or a pharmaceutically acceptable salt thereof, wherein $R_1$ is selected from the group consisting of —$CH_3$, =O, —OH, —$OCH_3$, —OC(O)$CH_3$, —NHNH-2,4-Dinitrophenyl, and =S;

$R_3$ is selected from the group consisting of H and $C_1$-$C_5$ alkyl;

n is an integer from 1 to 12; and

Z is H or a protective group.

2. The method according to claim 1, wherein the subject is a mammal.

3. The method according to claim 1, wherein the compound is administered as a tablet in a dosage range of 1 mg-500 mg.

4. The method according to claim 1, wherein Z is selected from the group consisting of butyloxycarbonyl and carbobenzoxy.

5. The method according to claim 1, wherein $R_1$ is =O, $R_3$ is methyl, and n is 4.

6. The method according to claim 1, wherein $R_1$ is =O, $R_3$ is H, Z is —C(=O)—O-t-butyl, and n is 4.

7. The method according to claim 1, wherein $R_1$ is —OH, $R_3$ is H, Z is —C(=O)—O-t-butyl, and n is 4.

8. The method according to claim 1, wherein n is 2-8.

* * * * *